United States Patent [19]
Goodman

[11] Patent Number: 6,087,398
[45] Date of Patent: Jul. 11, 2000

[54] SICKLE CELL ANEMIA TREATMENT

[75] Inventor: Steven R. Goodman, Mobile, Ala.

[73] Assignee: South Alabama Medical Science Foundation, Mobile, Ala.

[21] Appl. No.: 08/609,236

[22] Filed: Mar. 1, 1996

Related U.S. Application Data

[60] Provisional application No. 60/002,288, Aug. 14, 1995, abandoned.

[51] Int. Cl.$^7$ .................................................. A61K 31/195
[52] U.S. Cl. ........................................... 514/562; 514/815
[58] Field of Search ...................................... 514/562, 815

[56] References Cited

U.S. PATENT DOCUMENTS 3,847,545  11/1974  Shanbrom et al. ........................ 436/66

FOREIGN PATENT DOCUMENTS

WO 94/03169  2/1994  WIPO .

OTHER PUBLICATIONS

Rice–Evans, Catherine and Vidyavathi Udupi. *Thiol Compounds As Protective Agents In Erythrocytes Under Oxidative Stress. Free Rad. Comms.*, vol. 16, No. 5, pp. 315–323, UK: Harwood Academic Publishers GmbH, 1992.

*Primary Examiner*—Kevin E. Weddington
*Attorney, Agent, or Firm*—Benjamin Aaron Adler

[57] ABSTRACT

The present invention provides a method of treating sickle cell anemia comprising the step of administering to an individual in need of said treatment a therapeutically acceptable dose of reducing agent. In yet another embodiment of the present invention, there is provided a method of pharmacologically correcting a post-translational modification of the β-actin protein in sickled erythrocytes, comprising the step of contacting said sickled erythrocytes with a pharmacologically effective dose of a reducing agent. In still yet another embodiment of the present invention, there is provided a method of identifying a drug for use in treating sickle cell anemia. Any drug which hastens the HDSS Core Skeleton dissociation rate is tested by the in vitro ternary complex dissociation assay to test whether its effect is on HDSS beta-actin. Furthermore, drugs can be tested by the oxygenation-deoxygenation cycling assay for its ability to block ISC formation in vitro. Finally, drugs can be tested for ability to cause the conversion of preformed ISCs back to the biconcave shape.

3 Claims, 31 Drawing Sheets

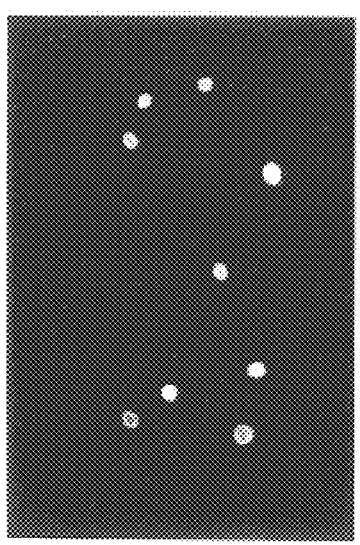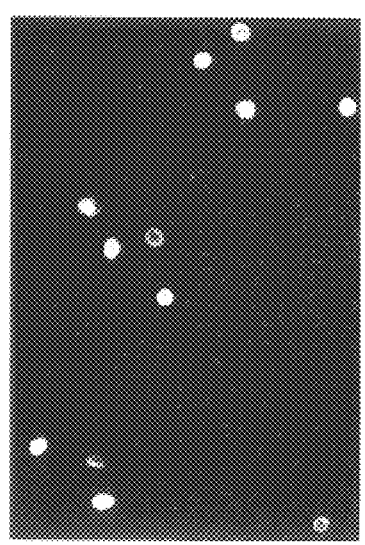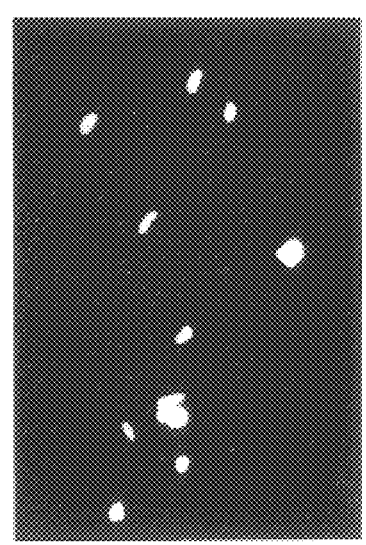

α/β Sp
4.1
Act a b c d e f g h

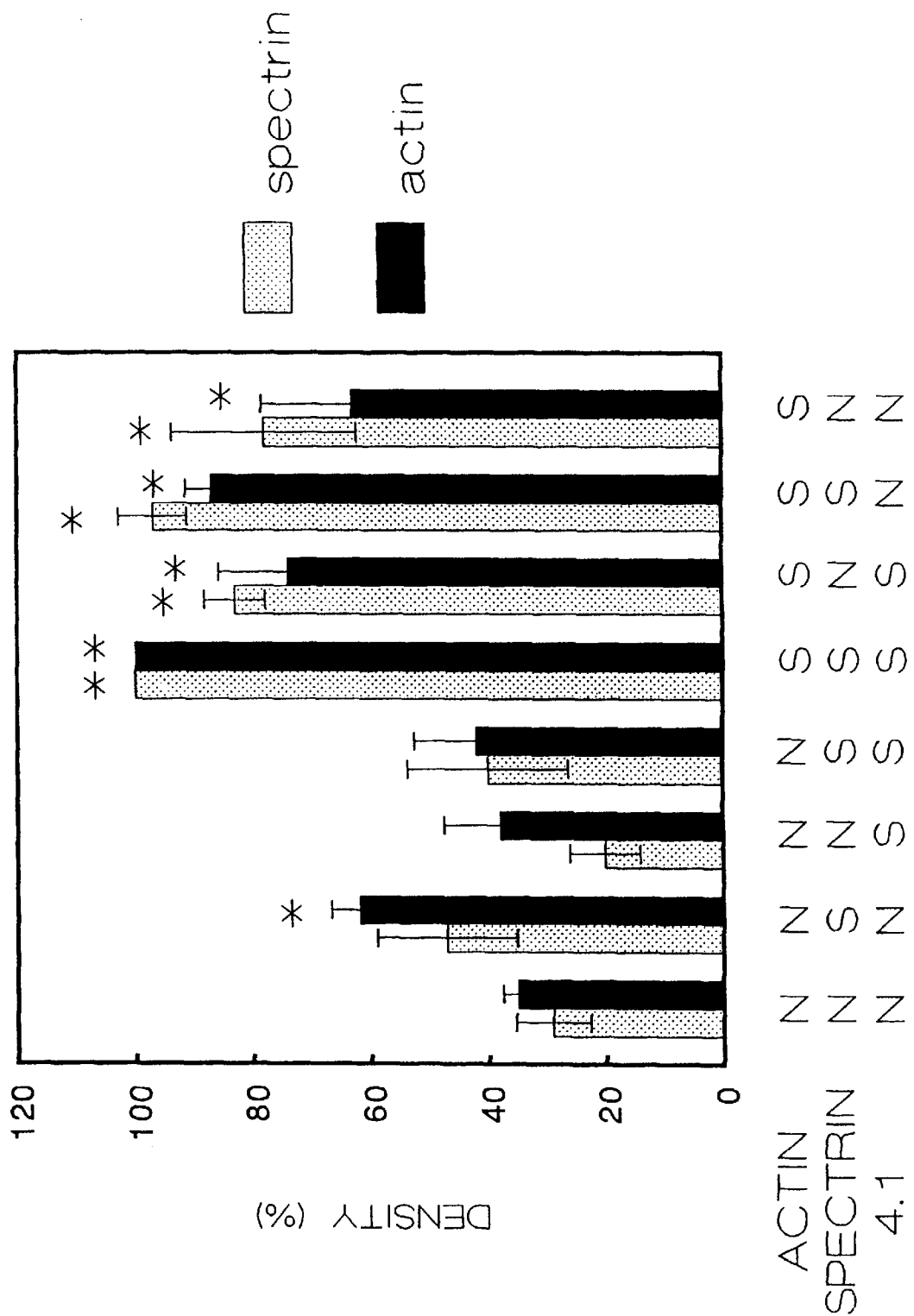

S—(2,4—DINITROPHENYLTHIO) $^{35}$S—CYSTEINE
($^{35}$S—DNPTC)

```
  1 DDDIAALVVD NGSGMCK AG FAGDDAPRAV FPSNGRPRH QGVMVGMGQKD
 51 SYVGDEAQS KRGILTLKYP IEHGIVTNWD DMEKIWHHTF YNELRVAPEEH
101 PVLLTEAPL NPKANREKMT QIMFETFNTP AMYVAIQAVL SLYASGRTTGI
151 VMDSGDGVT HTVPIYEGYA LPHAILRLDL AGRDLTDYLM KILTERGYSFT
201 TTAEREMVR DIKEK LCYVA LDFEQEMATA ASSSSLEK SY ELPDGQVITIG
251 NERFR CPEA LFQPSFLGME SCGIHETTFN SIMK CDVDIR KDLYANTVLSG
301 GTTMYPGIA DRMQKEITAL APSTMKIKII APPERKYSVW IGGSILASLST
351 FQQMWISKQ EYDESGPSIV HR KCF (SEQ ID No. 6)
```

FIG. 5B

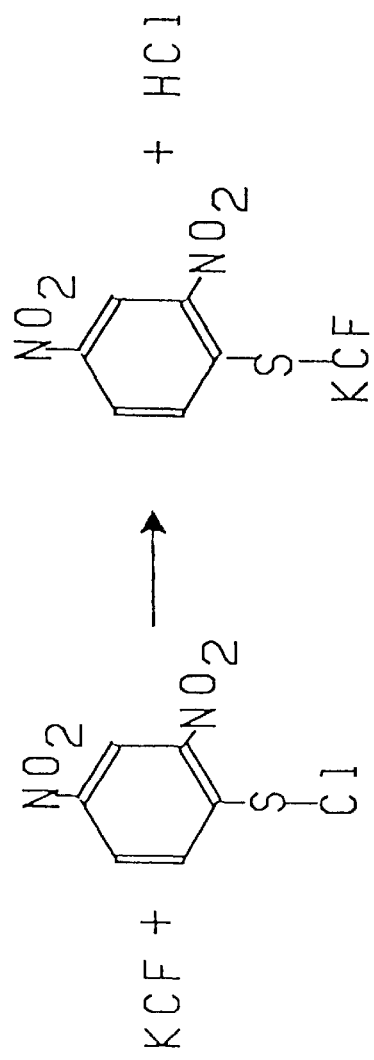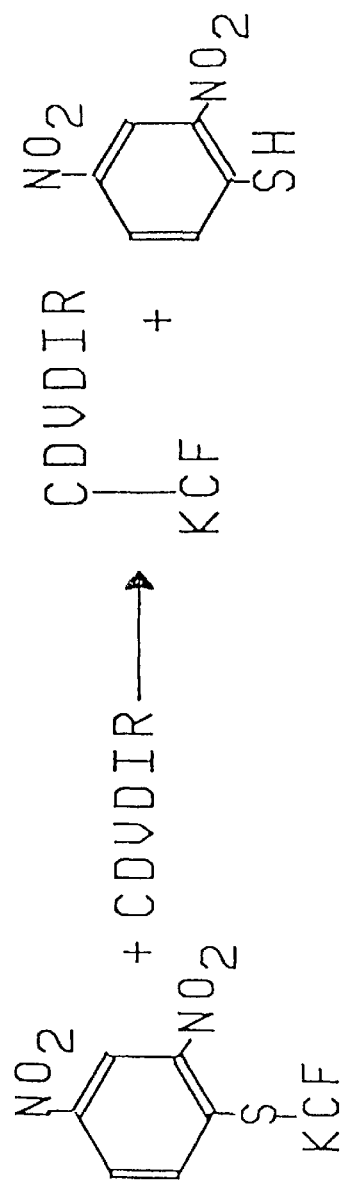
FIG. 9

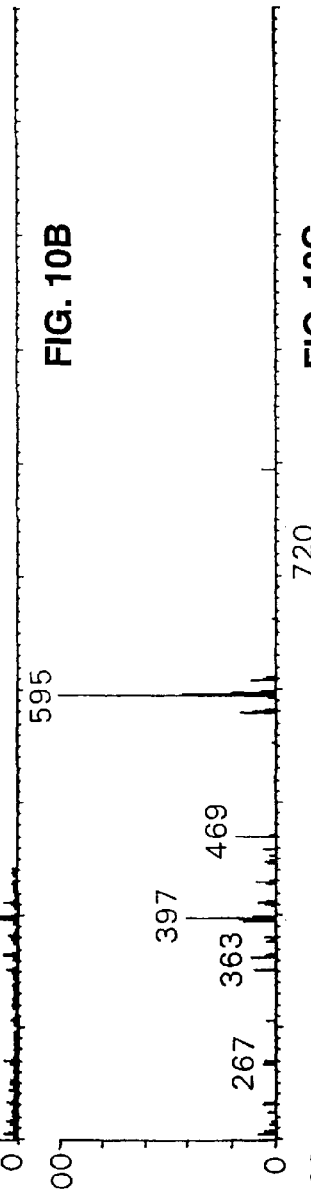
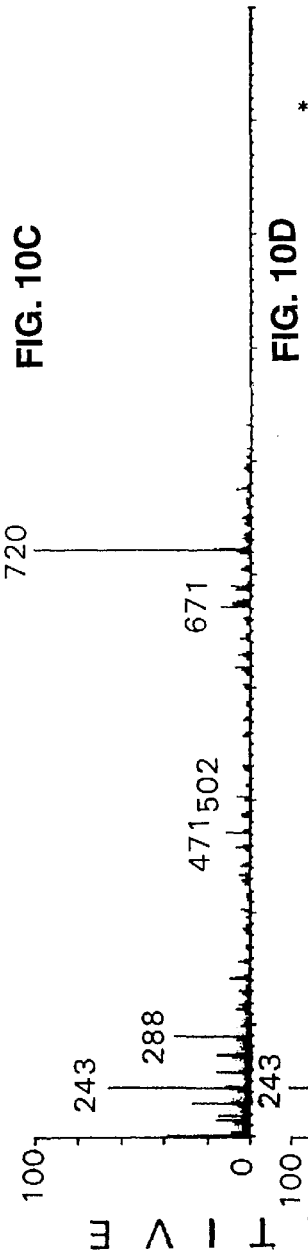
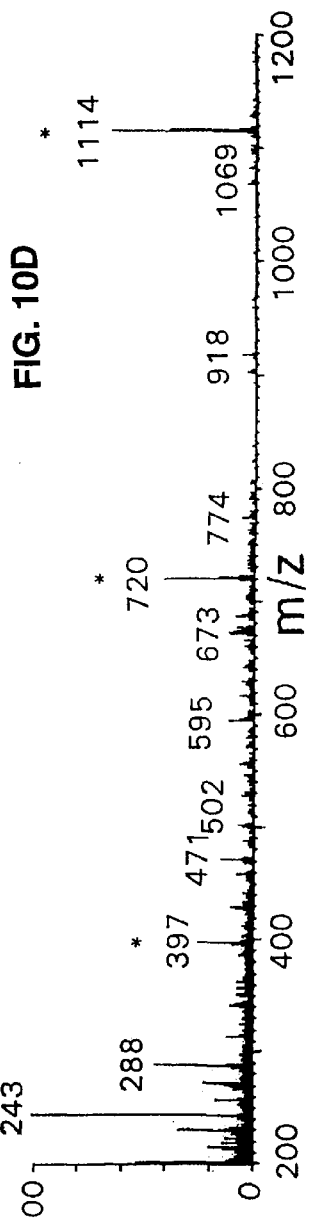
FIG. 10A
FIG. 10B
FIG. 10C
FIG. 10D

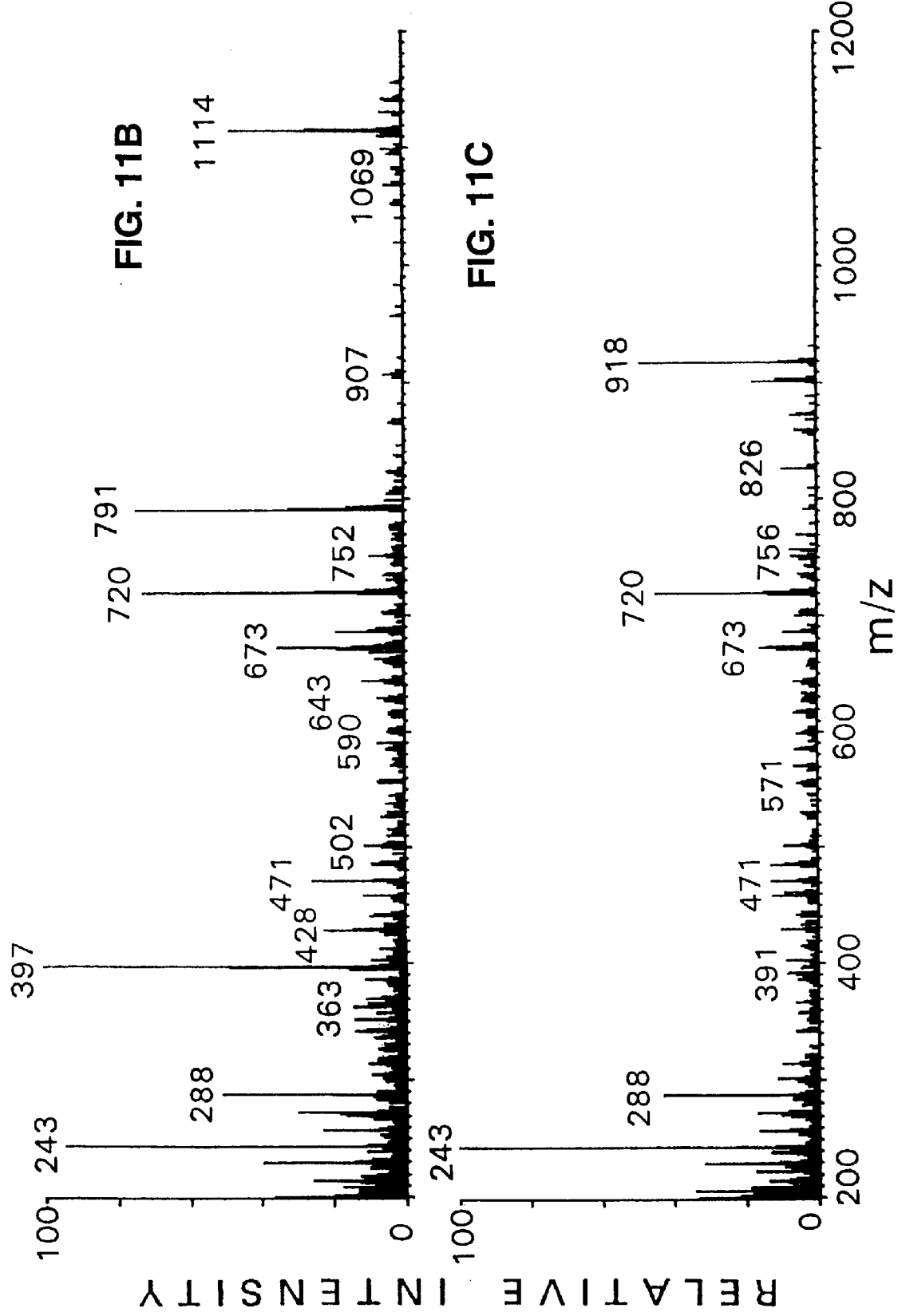

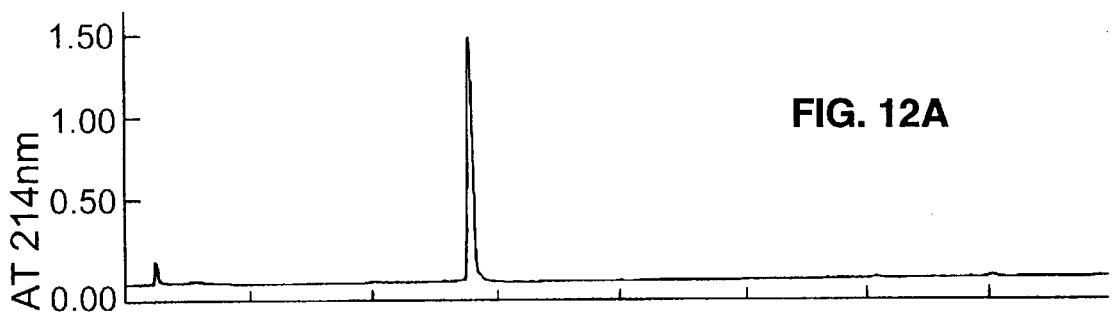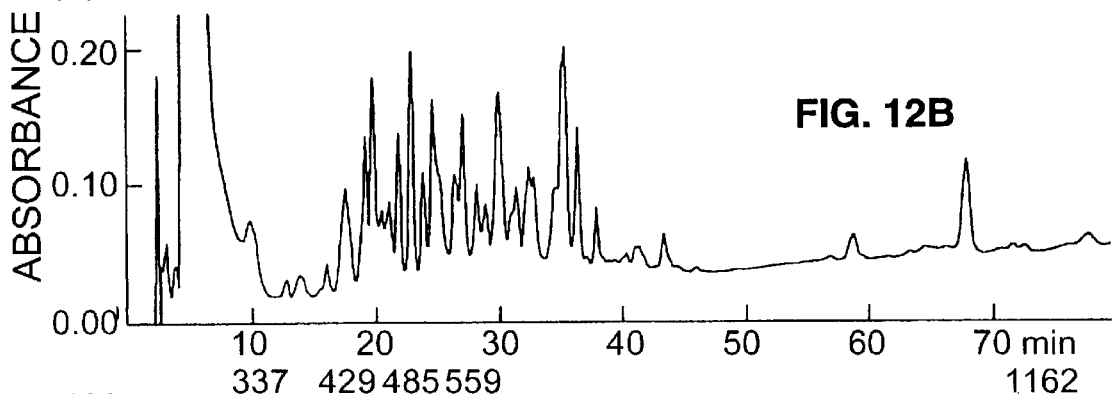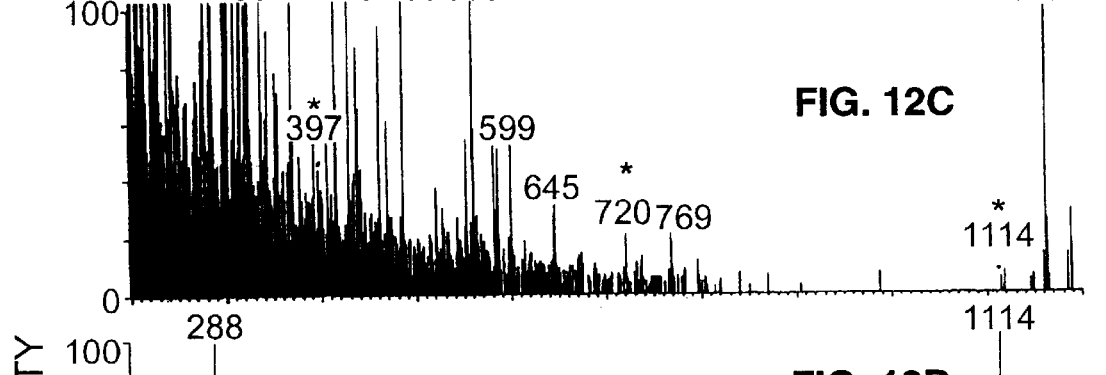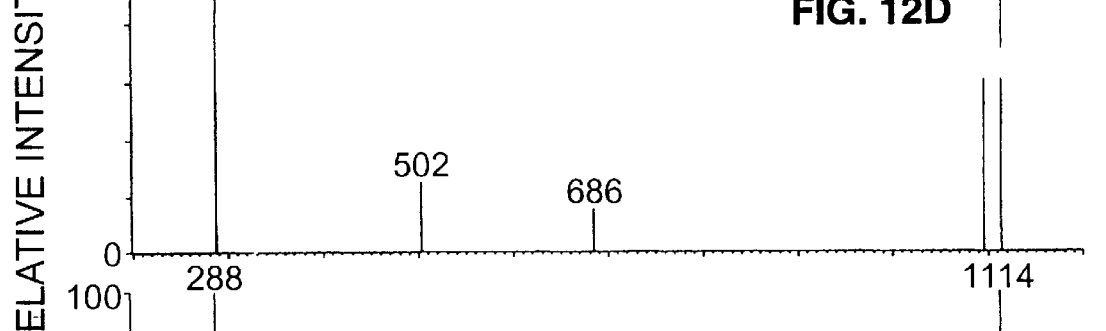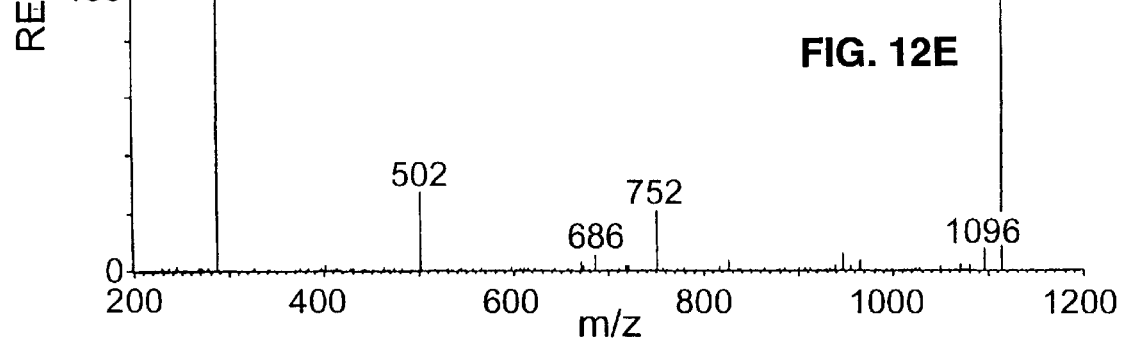

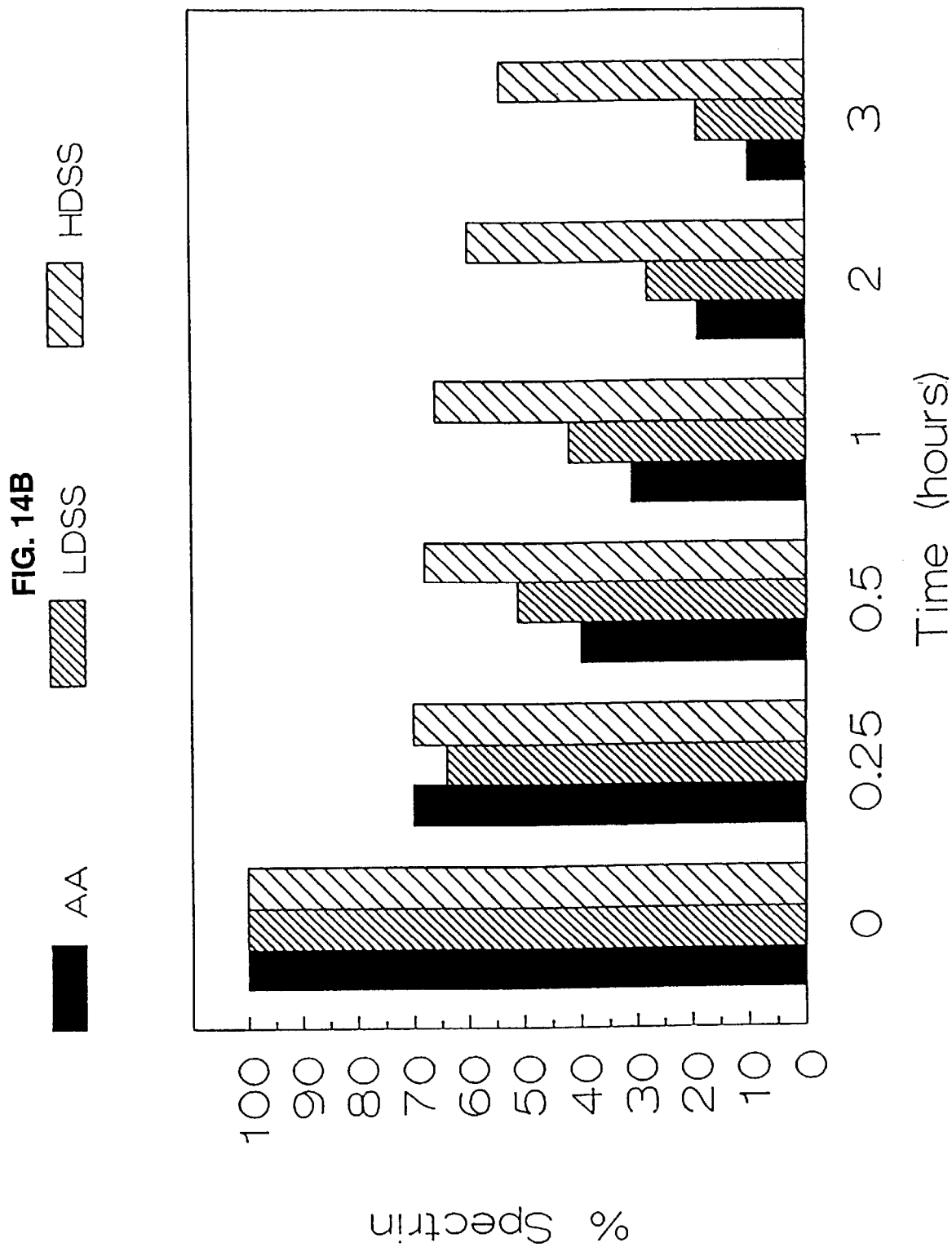

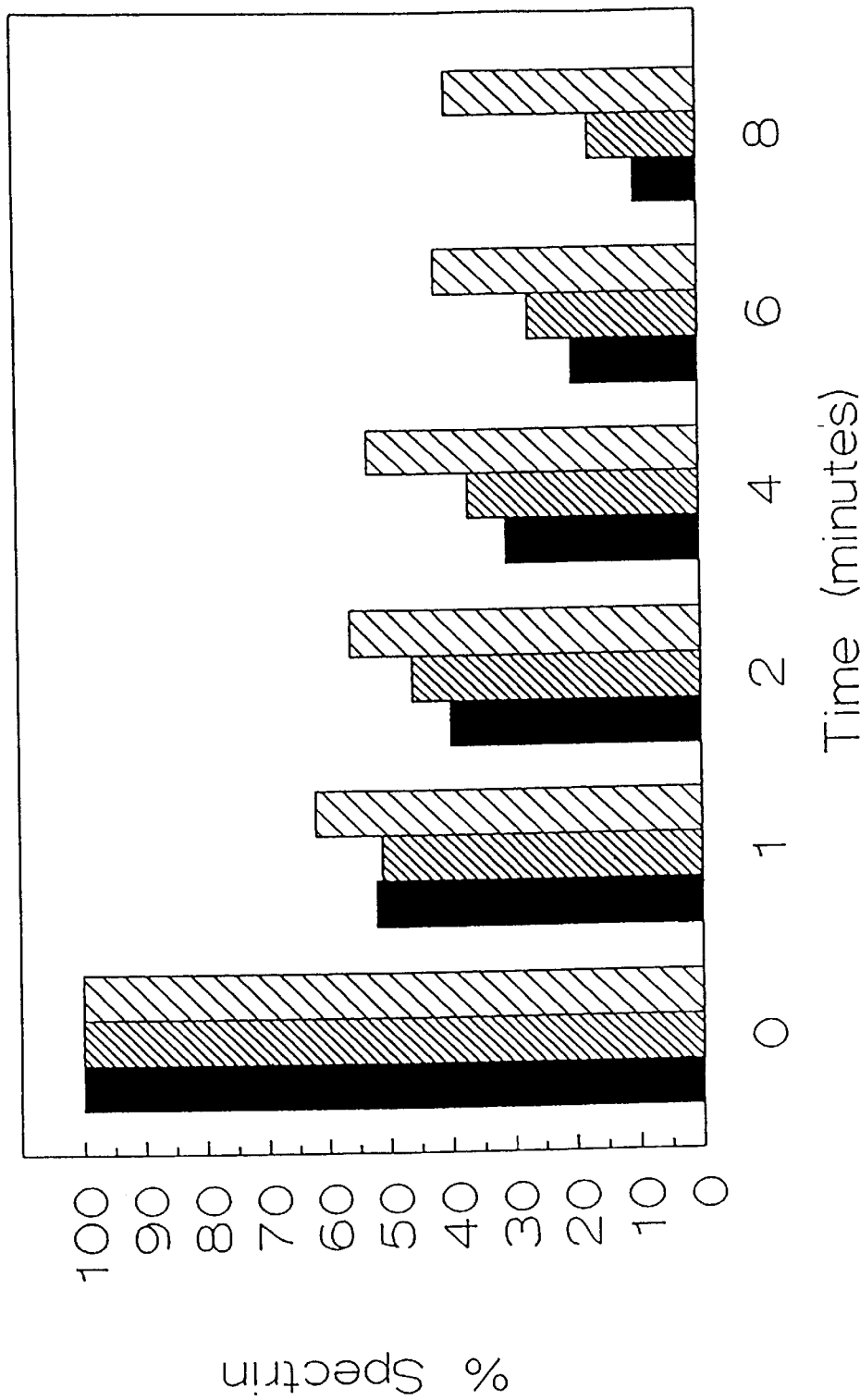

```
                           SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
         (A) LENGTH: 6
         (B) TYPE: Amino acid
         (C) STRANDEDNESS:
         (D) TOPOLOGY: Linear (ii) MOLECULE TYPE:
         (A) DESCRIPTION: Peptide (iii) HYPOTHETICAL: No (iv) ANTI-SENSE: No (v) FRAGMENT TYPE:

(vi) ORIGINAL SOURCE:
         (B) STRAIN:
         (C) INDIVIDUAL ISOLATE:
         (D) DEVELOPMENTAL STAGE:
         (F) TISSUE TYPE:
         (G) CELL TYPE:
         (H) CELL LINE:

(xi) SEQUENCE DESCRIPTION: SEQ ID NO: 1:

Cys Asp Val Asp Ile Arg
                5

(2) INFORMATION FOR SEQ ID NO: 2:

(i) SEQUENCE CHARACTERISTICS:
         (A) LENGTH: 17
         (B) TYPE: Amino acid
         (C) STRANDEDNESS:
         (D) TOPOLOGY: Linear (ii) MOLECULE TYPE:
         (A) DESCRIPTION: Peptide (iii) HYPOTHETICAL: No (iv) ANTI-SENSE: No (v) FRAGMENT TYPE:

(vi) ORIGINAL SOURCE:
         (B) STRAIN:
         (C) INDIVIDUAL ISOLATE:
         (D) DEVELOPMENTAL STAGE:
         (F) TISSUE TYPE:
         (G) CELL TYPE:
         (H) CELL LINE:

(xi) SEQUENCE DESCRIPTION: SEQ ID NO: 2:

Asp Asp Asp Ile Ala Ala Leu Val Val Asp Asn Gly Ser Gly Met
```

```
               5                  10                  15
Cys Lys (2) INFORMATION FOR SEQ ID NO: 3:

(i) SEQUENCE CHARACTERISTICS:
        (A) LENGTH: 23
        (B) TYPE: Amino acid
        (C) STRANDEDNESS:
        (D) TOPOLOGY: Linear (ii) MOLECULE TYPE:
        (A) DESCRIPTION: Peptide (iii) HYPOTHETICAL: No (iv) ANTI-SENSE: No (v) FRAGMENT TYPE:

(vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO: 3:

Leu Cys Tyr Val Ala Leu Asp Phe Glu Gln Glu Met Ala Thr Ala
               5                  10                  15

Ala Ser Ser Ser Ser Leu Glu Lys
               20

(2) INFORMATION FOR SEQ ID NO: 4:

(i) SEQUENCE CHARACTERISTICS:
        (A) LENGTH: 28
        (B) TYPE: Amino acid
        (C) STRANDEDNESS:
        (D) TOPOLOGY: Linear (ii) MOLECULE TYPE:
        (A) DESCRIPTION: Peptide (iii) HYPOTHETICAL: No (iv) ANTI-SENSE: No (v) FRAGMENT TYPE:

(vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO: 4:

Cys Pro Glu Ala Leu Phe Gln Pro Ser Phe Leu Gly Met Glu Ser
               5                  10                  15

Cys Gly Ile His Glu Thr Thr Phe Asn Ser Ile Met Lys
               20                  25

(2) INFORMATION FOR SEQ ID NO: 5:

(i) SEQUENCE CHARACTERISTICS:
        (A) LENGTH: 11
        (B) TYPE: Amino acid
        (C) STRANDEDNESS:
```

(D) TOPOLOGY: Linear (ii) MOLECULE TYPE:
              (A) DESCRIPTION: Peptide (iii) HYPOTHETICAL: No (iv) ANTI-SENSE: No (v) FRAGMENT TYPE:

(vi) ORIGINAL SOURCE:
              (B) STRAIN:
              (C) INDIVIDUAL ISOLATE:
              (D) DEVELOPMENTAL STAGE:
              (F) TISSUE TYPE:
              (G) CELL TYPE:
              (H) CELL LINE:

(xi) SEQUENCE DESCRIPTION: SEQ ID NO: 5:

Glu Ile Thr Ala Leu Ala Pro Ser Thr Met Lys
                  5                  10

(2) INFORMATION FOR SEQ ID NO:6:

(i) SEQUENCE CHARACTERISTICS:
              (A) LENGTH: 374
              (B) TYPE: Amino acid
              (C) STRANDEDNESS:
              (D) TOPOLOGY: Linear (ii) MOLECULE TYPE:
              (A) DESCRIPTION: Protein (iii) HYPOTHETICAL: No (iv) ANTI-SENSE: No (v) FRAGMENT TYPE:

(vi) ORIGINAL SOURCE:
              (B) STRAIN:
              (C) INDIVIDUAL ISOLATE:
              (D) DEVELOPMENTAL STAGE:
              (F) TISSUE TYPE:
              (G) CELL TYPE:
              (H) CELL LINE:

(xi) SEQUENCE DESCRIPTION: SEQ ID NO: 6:

Asp Asp Asp Ile Ala Ala Leu Val Val Asp Asn Gly Ser Gly Met
                  5                  10                  15

Cys Lys Ala Gly Phe Ala Gly Asp Asp Ala Pro Arg Ala Val Phe
                 20                  25                  30

Pro Ser Ile Val Gly Arg Pro Arg His Gln Gly Val Met Val Gly
                 35                  40                  45

Met Gly Gln Lys Asp Ser Tyr Val Gly Asp Glu Ala Gln Ser Lys
                 50                  55                  60

Arg Gly Ile Leu Thr Leu Lys Tyr Pro Ile Glu His Gly Ile Val
                 65                  70                  75

Thr Asn Trp Asp Asp Met Glu Lys Ile Trp His His Thr Phe Tyr
                 80                  85                  90

Asn Glu Leu Arg Val Ala Pro Glu Glu His Pro Val Leu Leu Thr
                 95                 100                 105

Glu Ala Pro Leu Asn Pro Lys Ala Asn Arg Glu Lys Met Thr Gln
                110                 105                 120

Ile Met Phe Glu Thr Phe Asn Thr Pro Ala Met Tyr Val Ala Ile
                125                 130                 135

```
Gln Ala Val Leu Ser Leu Tyr Ala Ser Gly Arg Thr Thr Gly Ile
                140                 145                 150

Val Met Asp Ser Gly Asp Gly Val Thr His Thr Val Pro Ile Tyr
                155                 160                 165

Glu Gly Thr Ala Leu Pro His Ala Ile Leu Arg Leu Asp Leu Ala
                170                 175                 180

Gly Arg Asp Leu Thr Asp Tyr Leu Met Lys Ile Leu Thr Glu Arg
                185                 190                 195

Gly Tyr Ser Phe Thr Thr Thr Ala Glu Arg Glu Ile Val Arg Asp
                200                 205                 210

Ile Lys Glu Lys Leu Cys Tyr Val Ala Leu Asp Phe Glu Gln Glu
                215                 220                 225

Met Ala Thr Ala Ala Ser Ser Ser Ser Leu Glu Lys Ser Tyr Glu
                230                 235                 240

Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser
                260                 265                 270

Cys Gly Ile His Glu Thr Thr Phe Asn Ser Ile Met Lys Cys Asp
                275                 280                 285

Val Asp Ile Arg Lys Asp Leu Tyr Ala Asn Thr Val Leu Ser Gly
                290                 295                 300

Gly Thr Thr Met Tyr Pro Gly Ile Ala Asp Arg Met Gln Lys Glu
                305                 310                 315

Ile Thr Ala Leu Ala Pro Ser Thr Met Lys Ile Lys Ile Ile Ala
                320                 325                 330

Pro Pro Glu Arg Lys Tyr Ser Val Trp Ile Gly Gly Ser Ile Leu
                335                 340                 345

Ala Ser Leu Ser Thr Phe Gln Gln Met Trp Ile Ser Lys Gln Glu
                350                 355                 360

Tyr Asp Glu Ser Gly Pro Ser Ile Val His Arg Lys Cys Phe
                365                 370
```

SICKLE CELL ANEMIA TREATMENT

CROSS-REFERENCE TO RELATED APPLICATION

This patent claims benefit of provisional patent application Ser. No. 60/002,288, filed Aug. 14, 1995, now abandoned.

FEDERAL FUNDING LEGEND

This invention was funded in part by NIH grants P60-HL38639. The federal government has, therefore certain rights in this invention.

BACKGROUND OF THE INVENTION

1. Field of the Invention

The present invention relates generally to the fields of molecular hematology and protein chemistry. More specifically, the present invention relates to a novel treatment for sickle cell anemia.

2. Description of the Related Art

Hemoglobinopathies encompass a number of anemias of genetic origin in which there is decreased production and/or increased destruction (hemolysis) of red blood cells. The blood of normal adult humans contains hemoglobin (designated as HbA) which contains two pairs of polypeptide chains designated alpha and beta. Fetal hemoglobin (HbF), which produces normal red blood cells, is present at birth, but the proportion of HbF decreases during the first months of life and the blood of a normal adult contains only about 2% HbF. There are genetic defects which result in the production by the body of abnormal hemoglobins with a concomitant impaired ability to maintain oxygen concentration. Among these genetically derived anemias are included thalassemia, Cooley's Disease and, most importantly, sickle-cell anemia (HbS disease).

Sickle-cell anemia is an inherited chronic hemolytic anemia characterized by sickle-shaped red blood cells present in part of the offspring of parents who are both heterozygotes to the abnormal gene which causes the sickling disease. This disease is recessive, and heterozygotes carrying this gene show no blatant anemia or similar abnormality. Thus, only about 25% of the children of parents who are both heterozygous are expected to be homozygotic to this abnormal gene and will develop sickle cell anemia and eventually sickling crisis (aplastic crisis). Few homozygotes live past 40 years of age and many show abnormal body growth patterns. The gene which characterizes sickling trait causes valine to be substituted for glutamic acid in the sixth position of the beta chain, thus producing HbS rather than HbA. Deoxygenated HbS is much less soluble than deoxy HbA and it forms a semisolid gel of rodlike tactoids, thus causing the red blood cells produced from HbS to assume a sickle shape. These abnormally shaped red blood cells form a sort of sludge. In addition, these HbS red blood cells are more fragile than normal red blood cells and hemolyze more easily, thus leading eventually to anemia. The clinical manifestations of an aplastic crisis in sickle-cell homozygotes include arthralgia with fever, jaundice, aseptic necrosis of the femoral head, chronic punched-out ulcers about the ankles plus episodes of severe abdominal pain with vomiting. Thrombosis and/or infarction may also be present. Laboratory findings include a monocytic anemia with an RBC count in the range 2–3 times. Early death, usually before 40, is caused by intercurrent infections (especially tuberculosis), multiple pulmonary emboli or thrombosis of a vessel supplying a vital area. In the past, treatment of sickle-cell anemia was symptomatic only.

Recently, however, it has been found that drugs which can increase production of the normal fetal hemoglobin HbF (since clearly, drugs cannot alter the HbS/HbA ratio in homozygotes since it is genetically determined), can tide a homozygote over the aplastic crisis, and thus potentially prolong their life. It has been known for some time that drugs such as 5-azacytidine, cytarabine and hydroxyurea could augment HbF production in anemic monkeys—see Levine et al, New Eng. J. Med. 310:869 (1984). Recent limited clinical studies have shown that these drugs do indeed increase HbF production in patients with sickle-cell disease—see Goldberg et al, New Eng. J. Med. 323:366 (1990) for hydroxyurea; Characheet al., Blood 69:109 (1988); 6th Annual Conf. on Hemoglobin Switching, Sep. 2, 1988 for 5-azacytidine and hydroxyurea; Veith et al, New Eng. J. Med. 313:1571 (1985) for cytarabine and hydroxyurea. In addition to the previously cited experiments in anemic monkeys (Levin et al loc. cit.), more recently Constantoulakis et al, Blood 77:1326 (1991) have developed a new model system for studying the induction of fetal hemoglobin (HbF) by various drugs, using adult transgenic mice carrying the human A (gamma) globin gene linked to the locus control region regulatory sequences and expressing heterocellularly HbF. Erythropoietin, 5-azacytidine, hydroxyurea and butyric acid esters (butyrate), all known in vivo HbF inducers in adult humans, also induced HbF in this model. Further, large scale human trials with hydroxyurea have been conducted. (Chavache et al., *N. Engl. J. Med.,* 332:1317–1322 (1995).

The molecular events which occur within red blood cells from homozygous sickle cell (SS) patients and to their extracellular environment leading to the painful sickle cell crisis, organ damage, and mortality are of great interest to the clinical and scientific community (reviews Hebbel, 1990, 1991, Powers, 1990, Francis, Jr. and Johnson, 1991, Joiner, 1993). Blood from SS patients can be separated on density gradients into morphologically and physiologically distinct red blood cell classes (Fabry et al, 1984). During the course of vaso-occlusion the highest density class of red blood cells are selectively trapped in the microvasculature (Kaul et al, 1986, 1989). This high density class of red blood cells include irreversibly sickled cells (ISCs) (60–85%) that retain a sickled shape in well oxygenated blood, and unsickleable SS dense discocytes (USDs) (Kaul et al, 1983). These observations explain why ISCs and USDs are reduced in the peripheral blood during a sickle cell crisis (Fabry et al, 1984, Ballas et al, 1988, Lande et al, 1988, Ballas and Smith, 1992). The ISCs appear to block the narrowed lumen of vessels lined primarily with the more adherent lower density reversibly sickled cells (RSCs), and sometimes by direct capillary occlusion (Kaul et al, 1989, Fabry et al, 1992).

Twenty years ago, Lux and coworkers made the observation that most red blood cell membranes (ghosts) isolated from ISCs remain sickled, and triton skeletons prepared from ISC ghosts all remain sickled (Lux et al, 1976). These observations demonstrated that after removal of all of the hemoglobin (HbS) from the ISC RBC, and most of the membrane phospholipids and integral membrane proteins, the remaining skeleton retained the sickled shape. When sickled RSC's were triton-extracted the resulting skeletons did not retain their sickled shape. In order for the released skeletons to remodel their shape, protein associations between spectrin, protein 4.1, and actin protofilaments (and other accessory proteins) must be dissociated, and then new interactions formed.

The red blood cell contains a two dimensional latticework of fibrous proteins which covers the cytoplasmic surface of its plasma membrane. This supramolecular structure, termed the membrane skeleton, maintains the biconcave shape of the erythrocyte, gives it essential properties of elasticity and flexibility for its circulatory travels, controls the lateral mobility of integral membrane proteins, and serves as a structural support for the bilayer (review, Goodman et al, 1988). The essential core components of this two dimensional meshwork are spectrin, f-actin, and protein 4.1 (Yu et al, 1973, Sheetz, 1979), although triton membrane skeletons isolated at moderate ionic strength conditions (such as those utilized by Lux et al (1976)) contain other more minor components.

Erythrocyte spectrin is primarily an $(\alpha\beta)_2$ tetrameric flexible rod of 200 nm extended contour length, formed by head-to-head linkage of two $\alpha\beta$ heterodimers (Shotton et al, 1979). Cloning and cDNA sequencing of both the $\alpha$ subunit (Sahr et al, 1990) and $\beta$ subunit (Winkelmann et al, 1990) have indicated molecular weights of 280 kD ($\alpha$) and 246 kD ($\beta$) for the spectrin subunits. Essential to the formation of the two dimensional membrane skeleton is the ability of spectrin tetramers to bind actin filaments at both ends, thereby crosslinking f-actin (Brenner and Korn, 1979, Cohen et al, 1980, Shen et al, 1986). The actin binding domain of human RBC spectrin has been localized to a stretch of 140 amino acids at the N terminus of $\beta$ spectrin from alanine$^{47}$ through lysine$^{186}$ (Karinch et al, 1990). Erythrocyte actin protofilaments observed on electron microscopy of negatively stained intact membrane skeletons fall within a narrow range of lengths, with a mean length of 33 to 37 nm in control (AA) red blood cells, equivalent to a double-stranded helix with 14 actin monomers (Shen et al, 1986, Byers and Branton, 1985). The extended skeleton appears to be primarily a hexagonal lattice (Liu et al, 1987) with actin protofilaments (and associated proteins) at the center and six corners of the hexagons, interconnected by spectrin tetramers (~85%) and three armed hexamers (~10%). The spectrin-actin interaction is strengthened by a peripheral membrane protein, protein 4.1, which also binds to the ends of the spectrin tetramers (Tyler et al, 1979, Ungewickell et al, 1979, Fowler and Taylor, 1980). Therefore spectrin, actin protofilaments, and protein 4.1 constitute the core RBC skeleton.

Other accessory proteins to the skeleton include protein 4.9 which bundles f-actin in vitro (Siegel and Branton 1985), tropomyosin which lines the grooves of actin protofilaments (Fowler and Bennett, 1984), and adducin a $Ca^{2+}$-calmodulin binding protein which stimulates the addition of spectrin to f-actin in a protein 4.1-independent manner (Gardner and Bennett, 1987, Mische et al, 1987). The spectrin membrane skeleton is attached to the membrane by at least two types of interactions. Ankyrin binds to $\beta$ spectrin 20 nm from the junction of the heterodimers and also binds to the integral membrane protein band 3 (Bennett and Stenbuck 1979, 1980, Yu and Goodman, 1979, Hargreaves et al, 1980, Wallin et al, 1984). The second membrane linkage is based on the ability of protein 4.1 to bind to an integral membrane protein (Shiffer and Goodman, 1984) which appears to be glycophorin C (Mueller and Morrison, 1981).

Previous attempts to look at membrane skeletal defects within the sickle cell have focussed on the membrane linkage proteins. Platt et al (1985) demonstrated that SS spectrin depleted inside-out vesicles (IOVs) bound ~50% less spectrin in vitro than did control AA IOV. While this suggested a potential ankyrin defect, purified ISC ankyrin bound spectrin normally in vitro. Schwartz et al (1987) demonstrated that SS protein 4.1 was more aggregated upon isolation than AA protein 4.1, and bound protein 4.1-depleted IOVs less effectively than AA IOV's. While both of these studies point to potentially important alterations in the linkage between the core skeleton and the SS bilayer, neither could explain the persistently sickled membrane skeleton observed on triton X-100 extraction of ISC ghosts (Lux et al, 1976). In the triton extracted skeletons the bilayer has been removed, yet the ISC skeleton remained sickled.

Hebbel et al (1982) have demonstrated that sickle cells generate about twice the amount of activated oxygen species found in normal red blood cells. The basis for this increase in oxygen radicals is the combined result of accelerated autoxidation of HbS to methemoglobin, a conversion which causes a release of heme (Hebbel et al, 1988). Heme is increased in content on the cytoplasmic surface of sickle cell membranes, and this increase correlates with the amount of membrane protein thiol modification (Kuross et al, 1988). It is therefore not surprising that spectrin, band 3, ankyrin, and protein 4.1 all have some degree of thiol modification (Rank et al, 1985, Schwartz et al, 1987). While the thiol modifications of spectrin and ankyrin are reversible with DTT (Rank et al, 1985), the oxidation of thiols in protein 4.1 is not reversible (Schwartz et al, 1987). Schwartz et al (1987) have reported that SS protein 4.1 contains 1–2 mole % fewer cysteine than control protein 4.1, and 1 mole % cysteic acid not found in control protein 4.1.

The prior art is deficient in the lack of effective means of treating sickle cell anemia. The present invention fulfills this longstanding need and desire in the art.

SUMMARY OF THE INVENTION

The current invention utilizes an in vitro spectrin-4.1-f-actin ternary complex dissociation assay to demonstrate that ISC $\beta$-actin is the major cause of the slow dissociation of the persistently sickled ISC core skeleton. Utilizing a combined protein chemistry, thiol labelling, and sophisticated mass spectrometry approach it was demonstrated that ISC $\beta$-actin has a unique modification when compared to RSC or AA $\beta$-actin. This posttranslational modification in ISC $\beta$-actin appears to be the formation of a disulfide bridge between cysteine$^{284}$ and cysteine$^{373}$. Therefore reversible thiol modification of $\beta$-actin leads to slow dissociation of the ISC membrane skeleton, which offers a reasonable explanation for the inability of the ISC skeleton to rapidly remodel when it is released from the bilayer. Additional protein components not present in the core skeletons, may participate in the slow remodelling of the ISC membrane skeleton in vivo. The present invention also directly demonstrates the existence of the disulfide bridge between cysteine$^{284}$ and cysteine$^{373}$ in ISC $\beta$-actin. The associated ISC $\beta$-actin tryptic cysteine-peptide (KCF-CDVDIR) was synthesized, characterized by HPLC, MS, MSMS, and identified in the tryptic digest of the ISC $\beta$-actin. A novel methodology was utilized to synthesize the relevant cysteine containing peptides and mass spectrometry to identify the peptide KCFCDVDIR in the tryptic digest of ISC $\beta$-actin. Since the KCF peptide contains cysteine$^{373}$ and CDVDIR (SEQ ID NO:1) contains cysteine$^{284}$ these results conclusively demonstrated the formation of a cysteine$^{284}$-cysteine$^{373}$ disulfide bridge in ISC $\beta$-actin.

In one embodiment of the present invention, there is provided a composition of matter comprising an cell permeable non-toxic reducing agent and a pharmaceutically acceptable carrier.

In another embodiment of the present invention, there is provided a method of treating sickle cell anemia comprising the step of administering to an individual in need of said treatment a therapeutically acceptable dose of reducing agent.

In yet another embodiment of the present invention, there is provided a method of pharmacologically correcting a post-translational modification of the β-actin protein in sickled erythrocytes, comprising the step of contacting said sickled erythrocytes with a pharmacologically effective dose of a reducing agent.

In still yet another embodiment of the present invention, there is provided a method of identifying a drug for use in treating sickle cell anemia. Any drug which hastens the HDSS Core Skeleton dissociation rate is tested by the in vitro ternary complex dissociation assay to test whether its effect is on HDSS beta-actin. The same drug is tested for its ability to block ISC formation in vitro, utilizing the oxygenation-deoxygenation procedure described herein to convert RSCs to ISCs. The same drug is also tested for its ability to convert ISCs back to the biconcave shape.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the indirect immunofluorescence of red blood cell core skeletons. Core skeletons prepared were applied to polylysine coated glass slides, fixed, and stained with rabbit anti-human red blood cell spectrin (FIGS. 1A, 1B, and 1C) and rabbit anti-chicken skeletal muscle actin (FIGS. 1D, 1E, and 1F) at 1:100 dilution. Fluorescein-conjugated goat anti rabbit IgG was utilized in a 1:100 dilution. FIGS. 1A and 1D are control core skeletons from AA erythrocytes isolated from the 45% Percoll layer. FIGS. 1B and 1E are core skeletons from the LDSS erythrocytes isolated from the 45% Percoll layer. FIGS. 1C and 1F are core skeletons from the HDSS erythrocytes isolated from the 65%/70% Percoll layer. The space bar equals 10 μm.

FIG. 3 shows the isolation of core skeleton proteins and in vitro ternary complex dissociation assay. FIG. 3B—Densitometric analysis of the amount of spectrin and actin which resist dissociation at 37° C. (30 minutes) in high ionic strength triton X-100 buffer, when spectrin-4.1-actin ternary complexes formed in vitro are shifted to these conditions. Under each set of bars is given the initial composition of normal AA (N) or HDSS (S) Actin, Spectrin and Protein 4.1 in the incubation mixture. The data is expressed as Density % which indicates the density of spectrin or actin remaining in any complex÷density of spectrin or actin remaining in the complex formed by the incubation of HDSS spectrin+HDSS actin+HDSS protein 4.1×100%. Data is presented as mean±standard error, with asterisks indicating a statistically significant difference (p<0.05) as compared to the N-Actin/N-Spectrin/N-4.1 sample. Note that HDSS actin forms a ternary complex that is resistant to dissociation even when it has been combined with AA normal spectrin and AA normal protein 4.1.

FIG. 4 shows the determination of the number of available thiols in HDSS, LDSS, and AA β-Actin. Reduced and nonreduced G-actin ($1.5 \times 10^{-5}$ M) from control (AA), HDSS, and LDSS erythrocytes was incubated with a 10 fold molar excess of DTNB. The reference cuvette contained the actin buffer (2 mM Tris, 0.2 mM ATP, 0.5 mM $NaN_3$, pH 7.8) plus $1.5 \times 10^{-4}$ M DTNB. The color reaction was monitored at 412 nm at 22° C.

FIG. 5 shows the structure of $^{35}$S-DNPTC and β-Actin. FIG. 5B—The primary structure of β actin is presented using the single letter code for amino acids (SEQ ID NO:6). The arrows indicate sites of trypsin cleavage. Stretches of amino acids in red indicate tryptic peptides which contain cysteine residues. $K^{372}$ is in red because under our conditions cleavage after $K^{372}$ occurs less frequently than cleavage after $R^{371}$, therefore KCF is generated.

FIG. 9 shows the reaction schematics: preparation of disulfide linked peptides from the linear cysteine containing peptides KCF and CDVDIR (SEQ ID NO:1). Activating agent for the coupling reaction: 2,4-dinitrosulfenyl chloride.

FIG. 10 shows the positive fast atom bombardment ionization mass spectra of the linear peptide starting compounds and their reaction products. Note the dominant molecular ion (MH$^+$) present in each spectrum: FIG. 10A. KCF, (MH$^+$ at m/z 397), FIG. 10B. activated (DNPT-) KCF (m/z 595), FIG. 10C. CDVDIR (m/z 720), FIG. 10D. disulfide linked KCF-CDVDIR (m/z 1114). The intense fragments m/z 397 abd 720 (molecular ions of the component peptides), are marked by * as diagnostic ions for this cysteine-peptide.

FIG. 11B. Mass spectrum of the first eluting compound KCF-CDVDIR; FIG. 11C. mass spectrum of the second eluting compound DNPT-CDVDIR. (The third eluting compound is activated KCF, i.e., excess agent). The sample was stored at pH 8.0, 4° C. for two weeks before chromatography.

FIG. 12A shows an HPLC trace of synthetic KCF-CDVDIR; FIG. 12B shows a β-Actin peptide map: HPLC trace of a tryptic digest from 250 ng protein. FIG. 12C shows a FAB mass spectrum of fraction #29 from the tryptic digest: the diagnostic ions for KCF-CDVDIR are marked by *. FIG. 12D shows a MSMS product ion spectrum of m/z 1114 generated from the tryptic digest fr #29. FIG. 12E shows a MSMS product ion spectrum of m/z 1114 generated from synthetic KCF-CDVDIR.

FIG. 13 shows the core membrane skeleton dissociation at 0° C.

FIG. 14 shows the core membrane skeleton dissociation at 24° C. FIG. 14B—Densitometric analysis of the amount of spectrin remaining in the core skeletons at various times of extraction at 24° C. The amount of spectrin in the original ghosts (time zero) was set at 100%.

FIG. 15 shows the core membrane skeleton dissociation at 30° C.

FIG. 16 shows the core membrane skeleton dissociation at 34° C. FIG. 16B—Densitometric analysis of the amount of spectrin remaining in the core skeletons at various times of extraction at 34° C. The amount of spectrin in the original ghosts (time zero) was set at 100%.

DETAILED DESCRIPTION OF THE INVENTION

Figure 1A:
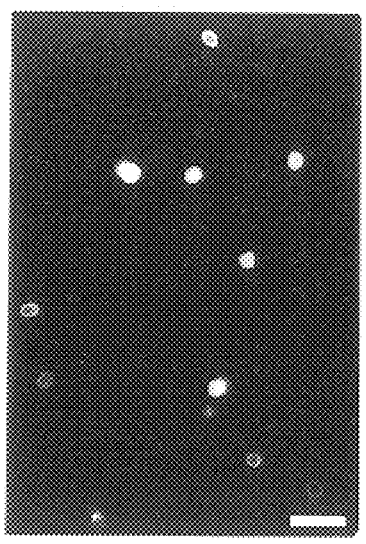

In the present invention, the following abbreviations may be used: ISC, irreversibly sickled cell; RSC, reversibly sickled cell; DDT, dithiothreitol; MS, mass spectrometry; MSMS, tandem mass spectrometry; RBC, red blood cell; DNPS-CL, 2,4-dinitrophenyl sulfenyl chloride; FMOC, fluorenyl methoxycarbonyl; DTNB, 5,5'- dithiobis(2-nitrobenzoic acid); TFA, trifluoracetic acid; FAB, fast atom bombardment ionization; CF-FAB, continuous-flow FAB; DNPT-, 2,4-dinitrophenylthio-.

The present invention is directed to a pharmaceutical composition of matter for the treatment of sickle cell anemia, comprising: a cell permeable non-toxic reducing agent and a pharmaceutically acceptable carrier. Although it is contemplated that any cell permeable non-toxic reducing agent would be effective in treating sickle cell anemia, the composition preferably contains a reducing agent selected from the group consisting of N-acetyl cysteine, dithiothreitol, cysteamine, dimercaprol, and succimer.

The present invention is directed to a method of treating sickle cell anemia in an individual in need of said treatment, comprising the step of: administering to said individual a therapeutically effective dose of a reducing agent. The preferred reducing agents are specified above. In this method of the present invention, the reducing agent is preferably administered in a dose of from about 70 mg/kg to about 140 mg/kg for n-acetyl cysteine. Within the clinical context of treating sickle cell anemia, the term "therapeutically effective" means blocking ISC formation, decreasing painful crises, reducing damage to tissues and organs, and increasing the length and quality of life.

The present invention is also directed to a method of pharmacologically correcting a post-translational modification of the β-actin protein in sickled erythrocytes in an individual in need of such treatment, comprising the step of: contacting said sickled erythrocytes with a pharmacologically effective dose of a reducing agent. Preferable reducing agents include N-acetyl cysteine, dithiothreitol, cysteamine, dimercaprol, and succimer. It is contemplated that an individual in need of such pharmacological correction would have sickle cell anemia or be at risk for developing this disease. Within the clinical context of a post-translational modification of the β-actin protein in sickled erythrocytes, the term "pharmacologically correcting" means blocking ISC formation, decreasing painful crises, reducing damage to tissues and organs, and increasing the length and quality of life. In one embodiment of this method, the sickled erythrocytes are contacted in vitro.

The present invention is also directed to a method of screening a pharmaceutical for use in treating sickle cell anemia, comprising the step of measuring said pharmaceutical's ability to hasten the core skeleton dissociation rate in high density sickle cells. After establishing that a drug hastens the core skeleton dissociation rate, then the drug's effect upon ISC actin is demonstrated by an in vitro ternary complex dissociation assay. The in vitro ternary complex dissociation assay comprises the steps of:

isolating normal spectrin, normal 4.1 and actin from the patient with sickle cell anemia;

incubating a selected drug with a purified spectrin protein 4.1 in a polymerization buffer;

sedimenting resulting ternary complexes and resuspending said sedimented complexes in high ionic strength triton buffer allowing said ternary complexes to dissociate;

centrifuging said complexes and analyzing resulting pellets to determine whether the presence of the drug reduces the amount of sedimented spectrin-4.1-actin complex.

Preferably, the polymerization buffer comprises 4 mM Tris, 0.2 mM ATP, 0.5 mM NaN$_3$ and 2 mM MgCl$_2$ and the ternary complexes are analyzed by SDS PAGE and laser densitometry.

The present invention also provides a novel core skeleton dissociation assay. The efficacy of various drugs of interest to hasten the dissociation rates of high density sickle cell (HDSS) core skeletons is examined. Briefly, freshly prepared AA, HDSS and LDSS membranes (50 µl) are incubated in 9 volumes of high ionic strength Triton X-100 buffer (10 mM NaPO$_4$, 600 mM KCl, 1 mM ATP, 1 mM DFP, 1% Triton X-100, pH 7.6) in the presence of varying drug concentrations for 0, 0.25, 0.5, 1, 2, and 3 hours at 24° C. Upon completion of extraction the samples are transferred to ice and centrifuged at 35,000×g for 45 minutes at 4° C. The pellets are resuspended to 50 µl in lysis buffer and analyzed by SDS PAGE and scanning densitometry. First order rate status are calculated as described below.

The present invention further provides a method of identifying a drug for use in treating sickle cell anemia. Any drug which hastens the HDSS Core Skeleton dissociation rate is tested by the in vitro ternary complex dissociation assay to test whether its effect is on HDSS beta-actin. Briefly, purified AA spectrin (400 µg/ml), AA 4.1 (80 µg/ml) and HDSS beta-actin (160 µg/ml) (which has been pretreated with varying concentrations of the drug to be tested) are incubated in 190 µl of polymerization buffer (4 mM Tris, 0.2 mM ATP, 0.5 mM naN$_3$, 2 mM MgCl$_2$, ph 7.4) for 1 hour at 22° C. The resulting ternary complexes are sedimented at 100,000×g for 30 minutes at 4° C. and resuspended in 190 µl of high ionic strength triton buffer. The ternary complexes are allowed to dissociate in this buffer at 37° C. for 30 minutes followed by centrifugation at 100,000×g for 30 minutes. The resulting pellets are analyzed by SDS PAGE and laser densitometry.

It is specifically contemplated that pharmaceutical compositions may be prepared for use in the novel methods of the present invention. In such a case, the pharmaceutical composition comprises a reducing of the present invention and a pharmaceutically acceptable carrier. A person having ordinary skill in this art would readily be able to determine, without undue experimentation, the appropriate dosages and routes of administration of the various reducing agents useful in practicing the present invention.

Generally, representative reducing agents or antioxidants useful in the methods of the present invention include dithiothreitol, Beta-mercaptoethanol, N-acetyl cysteine, Dimercaprol (BAL), succimer, and cysteamine. The pharmaceutical compositions comprising reducing agents are suitable for use in a variety of drug delivery systems. For a brief review of present methods for drug delivery, see Langer, *Science,* 249:1527–1533 (1990). Methods for preparing administrable compounds are known or apparent to those skilled in the art and are described in more detail, for example, in Remington's *Pharmaceutical Science,* 17th ed., Mack Publishing Company, Easton, Pa. (1988).

Administration of the compositions of the present invention may be by parenteral, oral, intranasal, intravenous, intramuscular, subcutaneous, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as capsules, tablets, liquid solutions, suspensions, or elixirs, for oral administration, or sterile liquid forms such as solutions, suspensions or emulsions. Any inert carrier is preferably used, such as saline, or phosphate-buffered saline, or any such carrier in which the novel compounds used in the method of the present invention have suitable solubility properties.

The following examples are given for the purpose of illustrating various embodiments of the invention and are not meant to limit the present invention in any fashion.

EXAMPLE 1

Preparation of Density Separated Red Blood Cells, Ghosts, and Core Skeletons

Blood (20–30 ml) was obtained by venipuncture from homozygous SS subjects, sickle cell trait subjects, and AA control subjects in vacutainer tubes containing 143 USP units of lithium heparin. Fresh blood (5 ml/gradient tube) was placed over a six layer step gradient (5 ml/layer) composed of 45%, 50%, 55%, 60%, 65%, and 70% Percoll in 18% Renografin M-60, 20 mM HEPES, 1 mM MgCl$_2$, 1 mM glucose (pH 7.4). Sedimentation was performed by centrifugation at 1500×g for 45 minutes. Each cell fraction within the Percoll layers was removed without cross-contamination and then washed two times in 10 mM $NaPO_4$, 150 mM NaCl, pH 7.6.

Packed red blood cells were lysed in 30 ml of ice cold lysis buffer (5 mM $NaPO_4$, 1 mM EDTA, pH 7.6) and ghosts sedimented at 31,000×g for 15 minutes at 4° C. This procedure was repeated until the pellet became white or light pink. Freshly prepared ghosts (1 volume) were incubated on ice for 15–30 minutes in 9 volumes of 10 mM $NaPO_4$, 0.6 M KCl, 1 mM ATP, 1 mM DFP, 1% Triton X-100, pH 7.6. In some cases skeletons were sedimented at 35,000×g for 45 minutes at 4° C., but not for immunofluorescence.

EXAMPLE 2
Immunofluorescent Images of Core Skeletons

Poly-L-lysine (0.1% in $dH_2O$) was applied to precleaned glass slides which were left to dry at room temperature. To one volume of RBC core skeletons was added one volume of 4% formaldehyde, 1.25% glutaraldehyde in PBS (150 mM NaCl, 10 mM $NaPO_4$, pH 7.6) and the mixture was incubated for 5 minutes at 22° C. Fixed skeletons were allowed to settle on poly-L-lysine glass slides for 5 minutes, and nonadherent skeletons were removed by 3 washes with PBS+1% BSA. Primary antibodies prepared in rabbits against chicken muscle actin (Sigma Immunochemical) and human red blood cell spectrin (characterized in Goodman et al, 1981) were diluted 1:100 in PBS+1% BSA and applied to skeletons for 15 minutes at 22° C. After 3 washes for 5 minutes each in PBS+1% BSA, FITC—conjugated goat anti-rabbit IgG (1:100 in PBS+1% BSA) was applied to the skeletons for 15 minutes. Nonbound secondary antibody was removed by three washes in PBS+1% BSA. The fluorescent skeletons were mounted and observed with a Leitz Dialux Fluorescent Microscope.

EXAMPLE 3
Isolation of Spectrin, Actin, and Protein 4.1

RBC core skeleton pellets were dissociated by incubation in 5 volumes of 2 M Tris pH 7.2 at 37° C. for 30 minutes followed by sedimentation of undissociated material at 32,000×g for 30 minutes (4° C.). The supernatant was layered onto a Sepharose 4B gel filtration column (1.5×170 cm) which had been equilibrated with 2 M Tris, 0.2 mM ATP pH 7.2. The spectrin, protein 4.1 and actin were eluted with this same buffer and collected in 2 ml fractions. Every fraction following the void volume (50 ml) was analyzed by SDS PAGE. Spectrin and protein 4.1 were dialyzed against 5 mM Tris, 0.5 mM $NaN_3$ pH 7.8. Actin was dialyzed against 2 mM Tris, 0.4 mM ATP, 0.5 mM $NaN_3$, 0.2 mM DTT (pH 7.8). Proteins were dialyzed with 3 changes every 12 h of 2 liters dialysis buffer and concentrated to 1 mg/ml spectrin, 400 µg/ml actin, 500 µg/ml protein 4.1. Skeletal proteins were stored at 4° C. and used within 48 h of isolation.

EXAMPLE 4
SDS PAGE

SDS PAGE was performed utilizing the discontinuous buffer system of Laemmli (1970) and a 9% polyacrylamide separating gel. Protein was detected with coomassie brilliant blue and densitometry performed with a Zeineh laser densitometer (Biomed Instruments, Inc.).

EXAMPLE 5
In Vitro Ternary Complex Dissociation Assay

This procedure is a modification of published ternary complex assays (Ungewickell et al, 1979, Cohen et al, 1980). Purified spectrin (400 µg/ml), protein 4.1 (80 µg/ml), and g-actin (160 µg/ml) were incubated in 190 µl of polymerization buffer (4 mM Tris, 0.2 mM ATP, 0.5 mM $NaN_3$, 2 mM $MgCl_2$, pH 7.4) for 1 h at 22° C. The resulting ternary complexes were sedimented at 100,000×g for 30 minutes (4° C.) and resuspended in 190 µl of high ionic strength triton buffer (10 mM $NaPO_4$, 0.6 M KCl, 1 mM ATP, 0.1 mM DFP, 1% Triton X-100 pH 7.6). The ternary complexes were allowed to dissociate in this buffer at 37° C. for 30 minutes followed by centrifugation at 100,000×g for 30 minutes. The resulting pellets were analyzed by SDS PAGE and laser densitometry. Purified spectrin, protein 4.1, and nonpolymerized g-actin (not complexed) demonstrate minimal (<10%) sedimentation at 100,000×g (30 minutes) with no difference between control and sickle cell proteins.

The statistical analysis was done using a commercially available statistical software package, SAS (Statistical Analysis System). The descriptive statistics like mean, range, and standard errors were compiled for each of the eight combinations of actin, spectrin, and 4.1. The one-way analysis of variance was performed to compare the means of these combinations. Once the difference among means was established, the Duncan's multiple range test was performed to test for pairwise differences. The statistical discussion on these techniques can be found in Montgomery (1991).

EXAMPLE 6
Determination of Exposed Thiols with DTNB

The number of exposed thiol groups were measured with DTNB (Ellman, 1958). The reaction was monitored by spectrometry at 412 nm using the extinction coefficient of the thiobenzoate ion (13,600 $M^{-1}$ $cm^{-1}$). The reaction was started by adding a 10-fold excess of DTNB to actin ($1.5×10^{-5}$ M) and a reference cuvette in 2 mM Tris, 0.2 mM ATP, 0.5 mM $NaN_3$ pH 7.8. The reaction at 22° C. was recorded over time on an LKB spectrophotometer. In some instances, the actin was reduced by dialyzing against 2 mM Tris, 0.2 mM ATP, 0.2 mM DTT, 0.5 mM $NaN_3$, pH 7.8 for 12 hours and then twice for 12 hours against the same buffer without DTT.

EXAMPLE 7
Reverse Phase HPLC of Actin Digests

AA, HDSS, and LDSS β-actin were dialyzed against 75 mM $NH_4$ $HCO_3$, 0.1 mM $CaCl_2$ pH 7.8. β-actins (400 µg/ml) were incubated with trypsin at 50/1 (mol/mol) for 20 hours at 37° C. Digested actin was dried to a powder in a Savant Speed-Vac, and then resuspended in half the original volume with Buffer A (0.1% trifluoroacetic acid (TFA) in HPLC quality $H_2O$). The actin digest (200 µg) was loaded onto a ODS 5 µm $C_{18}$ reverse phase column (4.6 mm×15 cm) with precolumn and eluted utilizing a Beckman System Gold HPLC. The column was washed 5 minutes with Buffer A, followed by a gradient of 0–100% buffer B (0.1% TFA, 80% acetonitrile) over 90 minutes. The flow rate was 1 ml/minutes and $OD_{215}$ was monitored. Fractions (1 ml) were collected and dried in a Savant Speed-Vac prior to Mass Spectrometry.

Each of the dried HPLC fractions were dissolved in 15 µl supporting fluid (methanol/glycerol/water 1:1:8) that contained 0.1% TFA. The injector for FAB-MS was loaded using 2.5 µl sample volumes, and injections were made in 10 scan intervals. The injector was carefully flushed with supporting fluid between samples (2×4 µl before loading, 2×4 µl after injection).

EXAMPLE 8

Mass Spectrometry-FAB-MS

A VG 70-250 SEQ hybrid tandem instrument equipped with a saddle-field FAB gun and a continuous flow FAB (CF-FAB) probe was used for the MS analyses. The probe was modified by attaching a micro-sampler injector (Rheodyne model 7520, Alltech) to it on a mounting plate fastened to the handle. The original 0.5 μl sample volume of the injector was increased to about 1.8 μl by enlarging the bore of the sample-channel to 0.0225". This injection volume ensured a chromatographic peak-width at half-height of about 45 seconds, adequate for acquiring 3 spectra under the flow and scanning conditions used. A fused silica capillary (3 ft long, 50 μm ID, 400 μm OD, RESTEC) led the CF-FAB supporting fluid (10% glycerol+10% methanol+80% $dH_2O$) from the injector to the probe-tip. The outstanding length of the capillary above the stainless steel probe tip surface was adjusted (0.1–0.3 mm) until stable ion-peaks were observed on the oscilloscope. A 2.5 cm long 3 mm wide filter paper strip coiled around the probe tip greatly increased the spectral stability. The supporting fluid to the injector was supplied by a syringe-pump (ISCO model 100D), through a PEEK tubing (1/16" OD, 0.010" ID) with a rate of 4 μl/minutes that required a pump pressure of ~200 psi, and resulted in a source pressure of $3\times10^{-4}$ mbar ($2.5\times10^{-1}$ mbar at the source fore-pump).

The MS source temperature was kept at 45° C., and the source potential (the ion accelerating voltage) at 6 kV. Xenon was used for the generation of the fast atom beam of 6 kV energy and 1 mA intensity. Positive ion mass spectra were recorded in the mass range of 240–3500 daltons and with a scan rate of 10 s/decade (20 s/scan).

EXAMPLE 9

Tandem MS/MS Spectrometry

For obtaining MS/MS spectra, the first (sector) MS was focused to transmit the precursor (parent) ion selected from the primary mass spectrum. The ICP (Instrument Control Parameters) program module of the data system was used in this process, and it required one injection of the sample. After focusing the sector MS, the ion signals from the second (dual quadrupole) MS were observed: the transmission of the parent ion and the occurrence of the product ions were checked on the oscilloscope. The resolution, analyzer-energy (pole-bias) and collision-energy dials were slightly adjusted when finer tuning seemed to be necessary; the double quad unit was basically optimized before the continuous flow experiments, under static FAB-MS conditions. Argon was used as a collision gas, and its flow was adjusted to decrease the original intensity of the precursor ion by one half. The pressure reading at the ion gauge of the associated diffusion pump was $1\times10^{-6}$ mbar. The collision energy was between 38 and 48 V. The protonated molecular ion of Leu-Enkephalin (m/z 556) was used for instrument tuning under static FAB-MS conditions, and injections of a 100 ng/μl Leu-Enkephalin solution were used to verify the optimal settings for the CF-FAB experiments.

The analyzer quadrupole was scanning with a speed of 5 s/spectrum in the mass range of 100–900 dalton, and the MS/MS spectra were recorded in MCA (multiple channel analyzer) format: 8–10 continuum spectra at the elution-maximum of the sample were summed, then the resulting spectrum processed (smoothed, peak-detected and mass converted) into a mass vs relative abundance, bar diagram format.

EXAMPLE 10

MALDI Mass Spectrometry Analysis

Control AA and HDSS β-actin were subjected to mass spectrometric analysis using a matrix-assisted laser desorption time-of-flight mass spectrometer constructed at Rockefeller University and described elsewhere (Beavis and Chait, 1989, Beavis and Chait, 1990). The mass spectra shown in FIG. 8 were obtained by adding the individual spectra obtained from 200 laser shots. Actin samples were prepared for laser desorption mass analysis as follows. The laser desorption matrix material (4-hydroxy-__-cyano-cinnamic acid) was dissolved in formic acid/water/isopropanol 1:3:2 (vol/vol/vol) to a concentration of 50 mM. A 75 mM ammonium bicarbonate solution (pH 7.8) containing the actin sample was then added to the matrix solution to give a final concentration of the actin of 0.5–1 μM. A small aliquot (0.5 μl) of this mixture was applied to the metal tip of the mass spectrometer sample probe and dried at room temperature. The sample was then inserted into the mass spectrometer and analyzed. Bovine carbonic anhydrase II (mol. wt 29022 daltons) was used as an internal calibrant to calibrate the mass spectra.

EXAMPLE 11

Synthesis of $^{35}$S-DNPTC

S-2,4 dinitrophenylthio-$^{35}$S-cysteine ($^{35}$S-DNPTC) was prepared by a modification of previously described protocols (Fontana et al, 1968, Drews and Faulstich, 1990). One mCi (12.5 μmoles) of $^{35}$S-cystine (Amersham) with a specific activity of 79.1 mCi/mmole and 62.5 μmoles of unlabelled L-cysteine (Aldrich Chemicals) were dissolved in 10 ml of nitrogenated double distilled deionized $H_2O$ and the solution adjusted to pH 8.6 with 0.8 M $NH_4OH$. After all crystals had dissolved the solution was stirred under $N_2$ for 2 hours at 22° C. followed by lyophilization under $N_2$ vapor. Lyophilized crystals were resuspended in 2 ml concentrated formic acid (Sigma Chemicals), mixed with 40.1 mg of 2,4-dinitrobenzenesulfenyl chloride (Aldrich Chemicals) freshly dissolved in 2 ml formic acid, and the solution was stirred under $N_2$ for 1.5 hours at 22° C. $^{35}$S-DNPTC was purified by crystallization from the reaction above by slowly pouring the mixture on 50 ml of dry peroxide free diethyl ether (Aldrich Chemicals) with gentle stirring at 22° C. for 10 minutes. Crystals were harvested by centrifugation at 10,300×g for 15 minutes, washed 3× in 50 ml of dry ether, and dried under vacuum. Finally, crystals were resuspended in 20 ml of 10 mM $NH_4HCO_3$ and recrystallized overnight at 4° C. Crystals were harvested by centrifugation and dried as described above. The specific activity of the final reagent was 28 mCi/mmol.

EXAMPLE 12

$^{35}$S-DNPTC Labelling of β-actin

β-actin (11.6 μM) was labelled with $^{35}$S-DNPTC (140 μM) in 2 mM Tris, 0.2 mM ATP, 0.5 mM $NaN_3$ pH 7.8. After incubation (80 minutes, 22° C.) the absorbance at 408 nm was measured versus a blank containing no actin, and the number of free thiols per mol AA β-actin was 1.9. In experiments on HDSS β-actin the number of thiols/mole actin was 0. Labelled actin was applied to a Sephadex G-50 column (50 cm×1.2 cm) and separated from unbound reagent. The column was eluted with 75 mM $NH_4 HCO_3$, 0.1 mM $CaCl_2$ pH 7.8, 0.5 ml fractions were collected, and $OD_{280}$ measured. The first peak of $OD_{280}$ contained S-($^{35}$S-cysteinyl)-β-actin and was concentrated using a centriprep-30 concentrator to 2.3 μM. The S-($^{35}$S-cysteinyl)-β-actin was incubated with 700 μM NEM for 30 minutes at 22° C., digested with 50/1 trypsin, concentrated and dried, and applied to reverse phase HPLC as described above.

EXAMPLE 13
Peptide Synthesis and $^{35}$S-DNPTC Labelling

Peptides representing fragments of actin generated by digestion with trypsin which contain cysteine residues were synthesized on solid phase using FMOC chemistry. Defined sequence of amino acids were assembled on a 431A peptide synthesizer (Applied Biosystems). TFA cleavage was used in conjunction with the appropriate chemical scavengers. Following synthesis, 100 μg of each peptide was purified by reverse phase HPLC (Beckman Instruments, System Gold), using a standard 0.1% TFA and 80% acetonitrile in 0.1% TFA gradient. After purification peptides were labelled with 10 fold excess S-2,4 dinitrophenylthio $^{35}$S-cysteine ($^{35}$S-DNPTC) by a modification of previously described protocols (Fontana et al, 1968, Drewes and Faulstich, 1990). The reaction of $^{35}$S-DNPTC with free reactive thiols could be followed spectrophotometrically since equivalent amounts of yellow 2,4-dinitrothiophenolate was released. Labelled peptides were again separated by reverse phase HPLC as above. After separation 50 μl of each fraction was mixed with 5 ml of liquid scintillation fluid and radioactivity measured (LKB). Fractions containing the highest counts were dried (Speed-Vac, Savant Instruments) and processed for mass spectroscopy.

EXAMPLE 14
Molecular Modeling of Cysteine$^{284}$-Cysteine$^{373}$Disulfide Bond Formation in ISC β Actin In order to model the disulfide bond formation between residues 373 and 284 of ISC beta-actin, the chaperon portion of the crystal structure profillin-beta-actin (Schutt et al, 1993) was removed, hydrogen atoms were added to the remaining structure and bond orders were assigned. This full-atom protein model served as the initial structure for constrained molecular dynamics (MD) simulations. Utilizing a physically relevant set of parameters to represent the potential and kinetic energy of the actin protein model (CFF91, Class II force field (Maple et al, 1990)), molecular dynamics affords conformational exploration across many local minima and maxima in an effort to obtain a globally realistic protein conformation as the CYS-373, CYS-284 distance was closed from 21 to 3 angstroms. The simulated temperature of the MD simulations was 300° K.

EXAMPLE 15
ISC Core Skeletons Retain the Sickled Shape and Dissociate at a Slower Rate at 37° C. than do RSC or Control Core Skeletons The present invention determined why the membrane skeleton released from an ISC, by triton X-100 extraction, appears unable to remodel to a round or biconcave shape. In their classic studies, Lux and colleagues demonstrated that ISCs extracted in 0.5% triton X-100 in 56 mM Na Borate pH 8.0 (30 minutes, 0° C.) yielded skeletons that remained sickled. At the ionic strength utilized by Lux et al (1976), spectrin, actin and protein 4.1 accounted for 85% of the coomassie blue stained protein observed in the skeletons; the remaining proteins being ankyrin, band 3, band 4.2 and the other accessory proteins discussed in the introduction. By repeating these experiments under the high ionic strength buffer conditions (10 mM NaPO$_4$, 0.6 M KCl, 1 mM ATP, 1 mM DFP pH 7.6+1% triton X-100) of Sheetz (1979) ISC, RSC, and control core skeletons were analyzed which maintain the physiological skeletal protein contacts with 95% of lipid extracted (Byers and Branton 1985, Shen et al, 1986, Liu et al, 1987) and contain almost exclusively spectrin, protein 4.1, and actin.

Figure 1B:
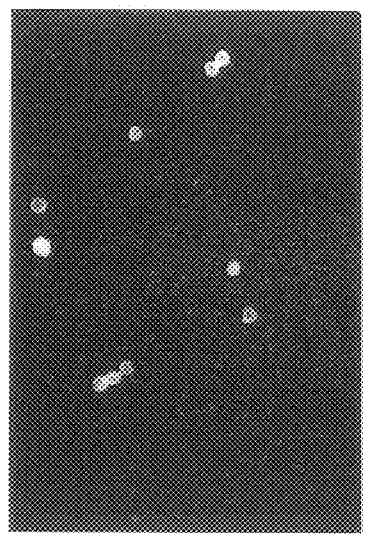
Figure 1C:
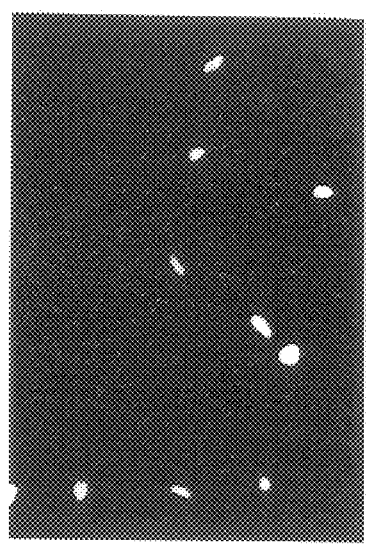

Red blood cells from control (AA) subjects and homozygous sickle cell subjects (SS) were separated by a percoll density step gradient. AA core skeletons, low density SS (LDSS) core skeletons, and high density SS (HDSS) core skeletons were prepared by extraction of ghosts in the high ionic strength triton buffer, and their shape analyzed by indirect immunofluorescence with spectrin antibodies (FIGS. 1A–1C) and actin antibodies (FIGS. 1D–1F). The control AA core skeleton all appeared biconcave or rounded (FIGS. 1A and 1D), as did the low density SS core skeletons derived primarily from RSCs (FIGS. 1B AND 1E). HDSS core skeletons remained almost exclusively sickled in shape because of the high percentage of ISCs in the 65/70% percoll fractions utilized (FIGS. 1C and 1F). The small number of rounded high density SS core skeletons (15–30%) were probably generated from the USDs. Thus, the defect leading to the persistently sickled ISC membrane skeleton is found within the core skeleton proteins: spectrin, protein 4.1, or actin, and that RSC core skeletons are capable of remodelling to a biconcave or rounded shape.

SDS PAGE analysis of ghost protein from AA erythrocytes isolated from 45% and 50% Percoll layers (FIG. 2 Left Panel A lanes a,b) and SS erythrocytes from 45%, 50%, 55%, 60%, 65%, 70% Percoll layers (FIG. 2A, lanes c–h) indicated no differences in membrane protein composition. Core skeletons prepared by a 15 minutes extraction at 4° C. in high ionic strength triton buffer demonstrated the presence of spectrin, protein 4.1 and actin in the control of SS core skeleton samples (FIG. 2B). All other proteins, including protein 4.9, were present at very low substoichiometric levels. Densitometry of the core skeletons prepared at 4° C. indicated that the composition of spectrin, protein 4.1 and actin were nearly identical in AA and SS core skeletons independent of the density of the AA and SS erythrocytes from which they were extracted (FIG. 2D).

Major differences in the stability of AA and SS core skeletons were observed when the extraction was conducted at 37° C. for 15 minutes in a water jacketed air/CO$_2$ incubator. As can be clearly seen in FIG. 2C (lanes a and b) and FIG. 2E at 37° C. (15 minutes) the control AA core skeletons are greater than 80% dissociated in agreement with the previous results of Yu et al (1973). Nearly identical results were obtained in separate experiments where the control erythrocytes were obtained from a 35 yr old African American male or a 40 yr old Caucasian male. However the highest density SS cells (65%, 70% Percoll, enriched in ISCs) produced core skeletons where greater than 60% of the spectrin, protein 4.1, and actin remained associated after 15 minutes at 37° C. (FIG. 2C lanes g and h). Lower density SS core skeletons dissociated at a similar rate to AA core skeletons (compare FIG. 2 Left Panel C lanes c and a). The resistance of SS core skeletons to dissociation at 37° C. increased with increasing density of the isolated erythrocytes (FIG. 2E). Only small density dependent increases in resistance to dissociation was observed for control erythrocytes (FIG. 2C compare lanes a and b) and sickle cell trait erythrocytes (data not shown).

Figure 2A:
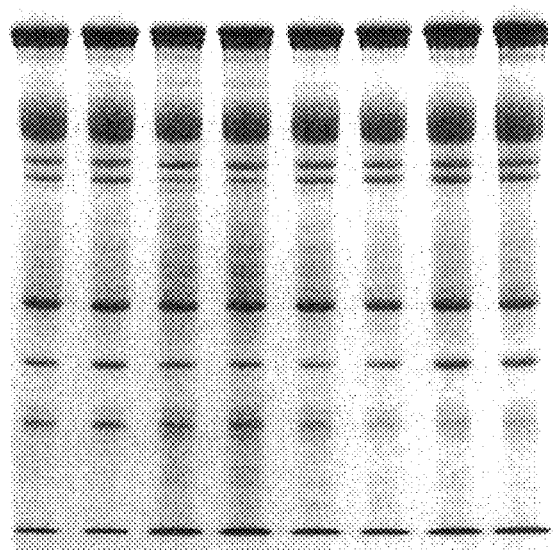
FIG. 2 shows in SDS PAGE of Density Separated AA and SS Erythrocyte Ghosts and Core Skeletons Prepared at 4° C. and 37° C. Coomassie blue stained SDS PAGE of 20 μl packed red blood cell ghosts (FIG. 2A), core skeletons prepared from 40 μl of packed red blood cell ghosts by high ionic strength triton X-100 extraction at 4° C. (15 minutes) (FIG. 2B), or 37° C. (15 minutes) (FIG. 2C). The source of the material in each lane is AA erythrocytes 45% percoll (a) and 50% percoll (b), and SS erythrocytes 45% (c), 50% (d), 55% (e), 60% (f), 65% (g), 70% (h) percoll.
FIG. 2D—Densitometric analysis of the protein content of core skeletons prepared at 4° C. from the SDS PAGE shown in FIG. 2B. The content of spectrin, actin, and protein 4.1 is given as % original skeletal protein remaining from the initial ghost protein. N=AA Normal Core Skeletons and S=SS Core Skeletons. X axis is percentage percoll gradient.
FIG. 2E—Densitometric analysis of the protein content of core skeleton prepared at 37° from the SDS PAGE shown in FIG. 2C.
Figure 2B:
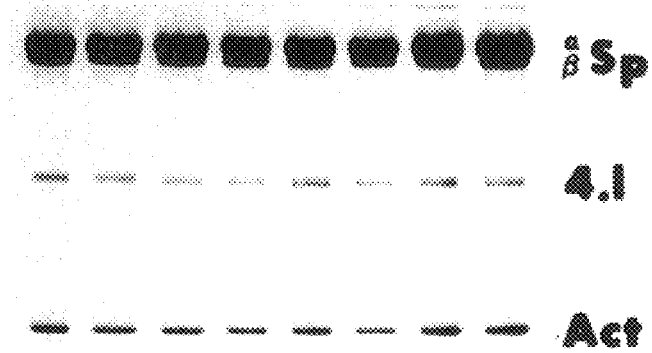
Figure 2C:
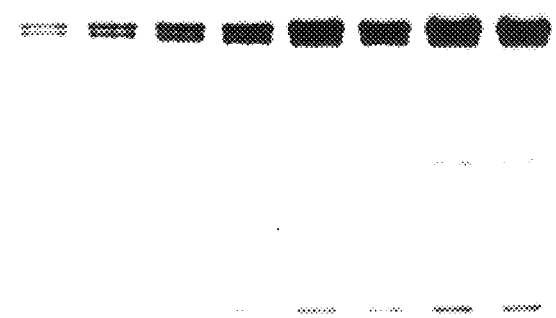
Figure 2D:
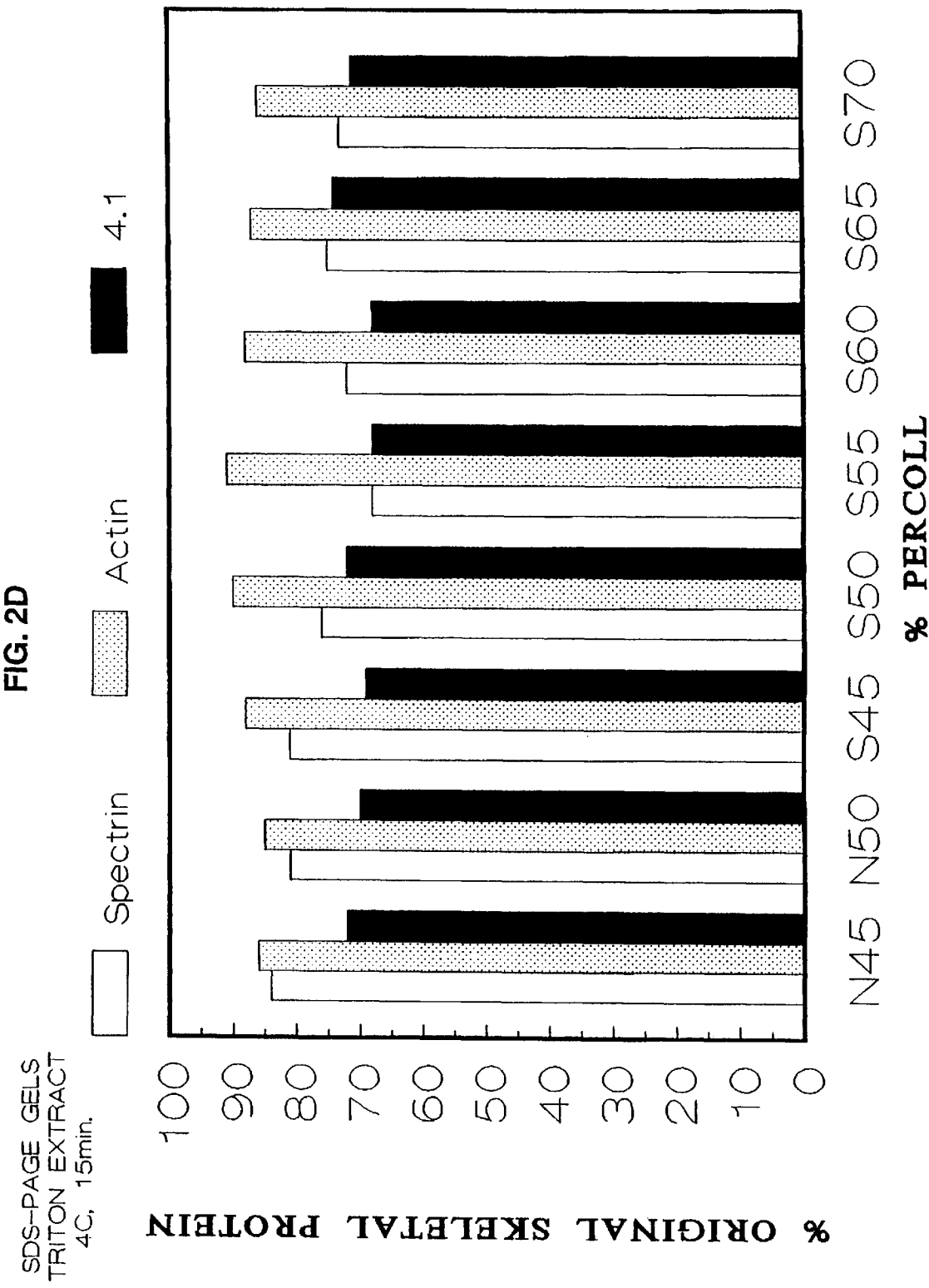
Figure 2E:
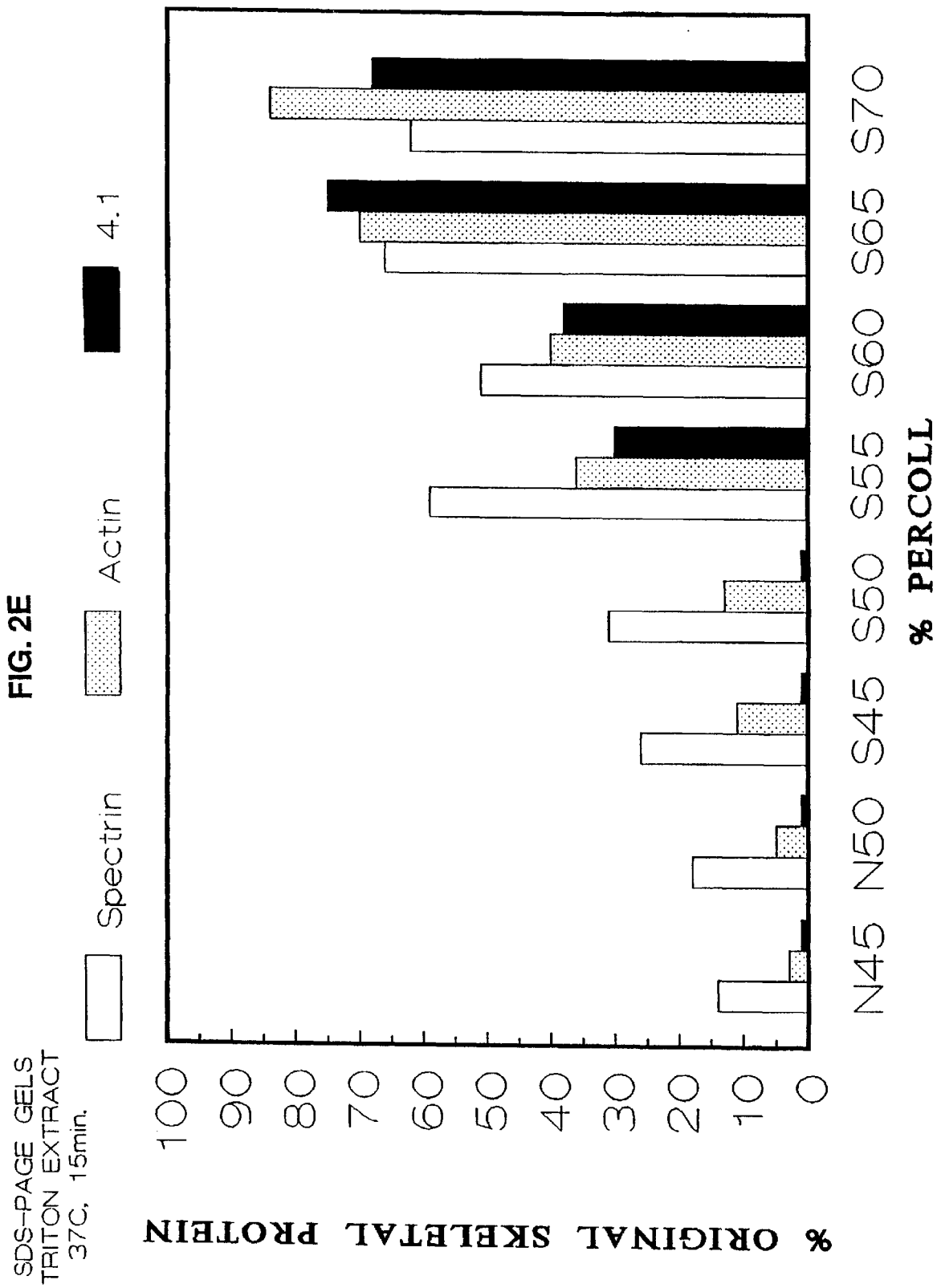

This slow dissociation of spectrin, protein 4.1 and actin within the ISC core skeleton was not based on a covalent bond because (1) given sufficient time (>30 minutes) the high density SS core skeletons will also disassociate at 37° C. and (2) the interactions of spectrin, protein 4.1, and actin within the "locked" ISC skeleton are broken by SDS (FIGS. 2A–2C lanes g and h). The term "locked" implies that the components of the ISC core skeleton dissassemble slowly at 37° C. (and therefore the skeleton is less capable of remodelling from its persistently sickled shape). Thus, a modification in spectrin, protein 4.1, or actin caused the slower dissociation of the ISC core skeleton, based on a noncovalent locking mechanism. Furthermore, this locking mechanism could be studied in vitro based on the rate of dissociation of ISC versus control core skeletons at 37° C. While the dissociation experiment under the precise conditions described (37° C., water jacketed air/$CO_2$ incubator) and presented in FIG. 2C was performed on two independent sickle cell patients, similar experiments were performed at 24° C. up to 37° C. (water bath regulated) on ten additional SS subjects (described below). All twelve SS subjects studied, at all temperatures studied (24° C.–37° C.), that HDSS core skeletons (enriched in ISCs) dissociate more slowly than do LDSS core skeleton (enriched in RSCs), and both have a slower rate of dissociation than AA core skeletons (data not shown).

Figure 3A:
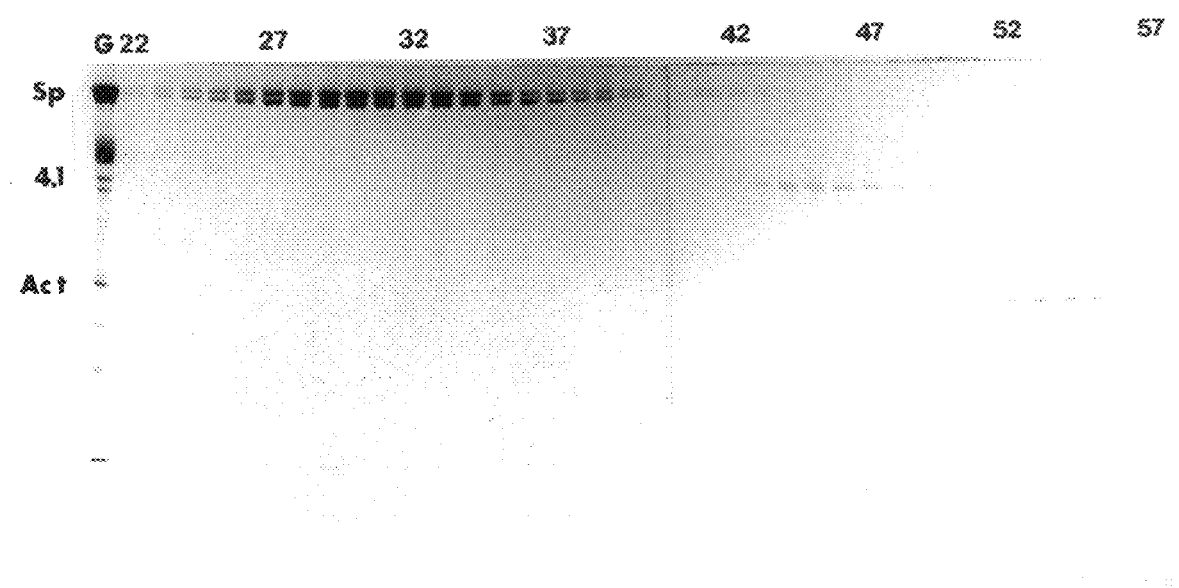
FIG. 3A—SDS PAGE of purified spectrin, protein 4.1, and actin isolated by 2 M Tris pH 7.2 extraction of core skeletons followed by gel filtration on Sepharose 4B. Fraction numbers are given above the gel.

EXAMPLE 16
The In Vitro Ternary Complex Dissociation Assay Allows the Identification of β-Actin and Spectrin as the Functionally Altered Proteins Leading to the Slow Dissociating ISC Ternary Complex Based on the observation that ISC core skeletons were more resistant to dissociation at 37° C., than control AA or RSC skeletons, an in vitro assay was created to determine the protein(s) leading to the slow dissociation of the ISC skeleton. Spectrin, protein 4.1, and actin were isolated by extraction of core skeletons from AA and high density SS red blood cells in 2 M Tris pH 7.2 at 37° C. The extract was then placed on a Sepharose 4B gel filtration column, which led to the isolation of pure spectrin, protein 4.1, and actin as demonstrated on a typical SDS PAGE shown in FIG. 3A. To obtain enough spectrin, protein 4.1, and actin from high density SS erythrocytes for the in vitro ternary complex dissociation assay, the ghosts from two SS patients (20 ml blood each) were combined in each experiment.

Spectrin, protein 4.1, and actin isolated from high density SS and control AA core skeletons (prepared at 4° C.) were recombined at final concentrations of 400 μg/ml, 80 μg/ml, and 160 μg/ml respectively in polymerizing buffer (4 mM Tris, 0.2 mM ATP, 0.5 mM $NaNa_3$, 2 mM $MgCl_2$, pH 7.4). (only spectrin, protein 4.1 and actin were included in the assay because these were the components of the released core skeletons from ISCs which retained a sickled shape (FIG. 1) and demonstrated resistance to dissociation at 37° C. (FIG. 2). It is possible that other accessory proteins may also play a role in the slow remodelling of the ISC membrane skeleton in vivo). Under these conditions, and ratio of protein components, spectrin, actin, and protein 4.1 are known to form ternary complexes that resemble their physiological molecular contacts (Cohen et al, 1980); although the supramolecular structures formed appear quite different from negatively stained membrane skeletons. The differences in appearance may be due to the role the accessory proteins may play in skeleton assembly and the nature of the spectrin-4.1-actin interaction is basically the same as in the intact skeleton. After incubation (22° C., 1 hr) the resulting spectrin-4.1-actin complex was sedimented and then shifted to the high ionic strength Triton X-100 buffer and incubated at 37° C. for 30 minutes to allow dissociation to occur. The remaining ternary complex harvested by 100,000×g centrifugation (30 minutes) was analyzed by SDS PAGE and laser densitometry (FIG. 3B). Although the initial ternary complexes formed by HDSS and AA spectrin, protein 4.1, and actin were identical (because a 1 hour incubation was utilized which is sufficient time for AA and SS spectrin-4.1-actin ternary complex formation to reach steady state), after shifting the ternary complexes to the high ionic strength triton X-100 buffer at 37° C., the expected differences in disassociation at 37° C. were again seen. The data presented in FIG. 3B are the mean plus/minus standard error of three independent experiments which all gave very similar results. When the control spectrin-4.1-actin ternary complex was shifted to 37° C., only 28.7±6.4% of the spectrin and 35.0±2.5% of the actin resisted dissociation when compared to the HDSS ternary complex (FIG. 3B). This allowed the critical mixing-matching experiments to be performed where the initial ternary complexes were formed from comixtures of HDSS and AA skeletal proteins. Utilizing this technique, it was demonstrated that a comixture of AA spectrin, AA actin, and HDSS protein 4.1 formed a ternary complex where only 20.0±6.0% of the spectrin and 28.0±4.6% of the actin resisted dissociation at 37° C. These values are not statistically distinct from that obtained with the control ternary complex and therefore protein 4.1 does not play a role in the slow dissociation of the HDSS ternary complex. It is important to note that although HDSS protein 4.1 is known to contain oxidative damage including conversion of cysteines to cysteic acid (Schwartz et al, 1987), these 4.1 modifications do not contribute to the slow dissociation of the HDSS ternary complex. On the other hand, the comixture of AA spectrin, AA protein 4.1, and HDSS actin formed a ternary complex were 78.3±15.7% of the spectrin and 63.3±15.4% of the actin resisted dissociation at 37° C. as compared to the HDSS ternary complex (FIG. 3B). Both of these values are statistically distinct (p<0.05) from the control ternary complex values (28.7±6.4% and 35.0±2.5%) and therefore β-actin was the major culprit in the slow dissociation of the HDSS ternary complex. The comixture of HDSS spectrin, AA protein 4.1, and AA actin yielded a ternary complex where 46.7±11.9% of the spectrin and 61.7±4.8% of the actin resisted dissociation at 37° C. For this complex, where only spectrin came from the high density SS erythrocytes, the difference from the control ternary complex was only significantly different for actin dissociation (FIG. 3B). Thus, a defect in ISC β-actin was the key determinant of the slowly dissociating ISC skeleton, spectrin also appears to play some role, while protein 4.1 is not responsible for the locking mechanism. Since β-actin was the major determinant of the slow dissociation of the ternary complex under the conditions of the assay, and a much smaller protein than spectrin, the ISC β-actin modification was determined first.

EXAMPLE 17
Search for the ISC β-Actin Defect Leads to Modified Cysteines

To determine the posttranslational modifications of ISC β-actin, β-actin was first isolated from AA, HDSS (65%, 70% percoll layers, enriched in ISCs) and LDSS (45, 50% percoll layers, enriched in RSCs) erythrocytes. The isolated β-actin samples were reduced in a buffer containing DTT (0.2 mM), digested with trypsin (50/1, mol/mol) for 20 hours at 37° C., and actin peptides were separated by reverse phase HPLC on a $C_{18}$ column. The resulting peptide maps for HDSS β-actin, LDSS β-actin, and AA β-actin were nearly identical (data not shown). Detailed comparisons of the protein containing HPLC fractions (1–50) for HDSS, LDSS, and AA β-actins by fast atom bombardment mass spectrometry (FAB-MS) yielded virtually identical spectra (data not shown). Of the 38 potential peptides generated by tryptic digestion 20 could be assigned to major ions within the FAB-MS spectra. These 20 tryptic peptide molecular ions were identical in mass when comparing HDSS, LDSS, and control β-actin.

Figure 4A:
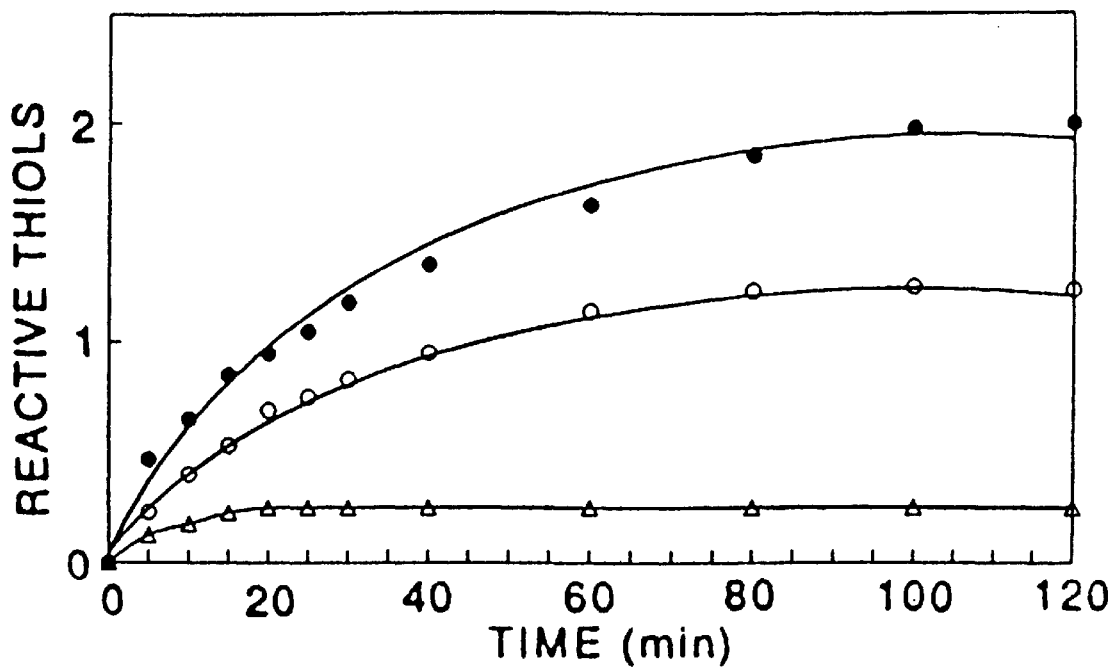
FIG. 4A. G-actin samples were not reduced. AA actin (•) had 2.0 thiols per mole β actin, LDSS actin (o) had 1.2 thiols per mole β actin, and HDSS actin (Δ) had 0.2 thiols per mole β actin.
Figure 4B:
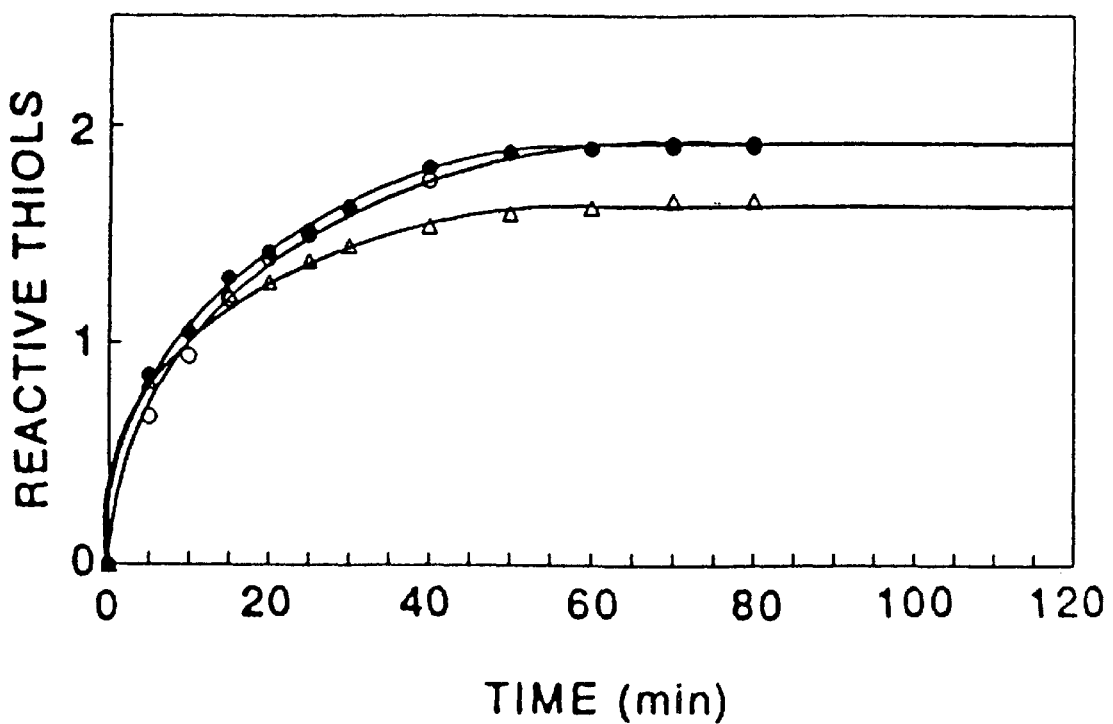
FIG. 4B. G-actin samples were reduced with a buffer containing 0.2 mM DTT, followed by removal of DTT prior to DTNB measurements of available thiols. Reduced β-actins from AA (•) and LDSS (o) erythrocytes contained 2.0 thiols per mole actin, and β-actin from HDSS (Δ) erythrocytes had 1.6 thiols per mole actin.
Figure 5A:
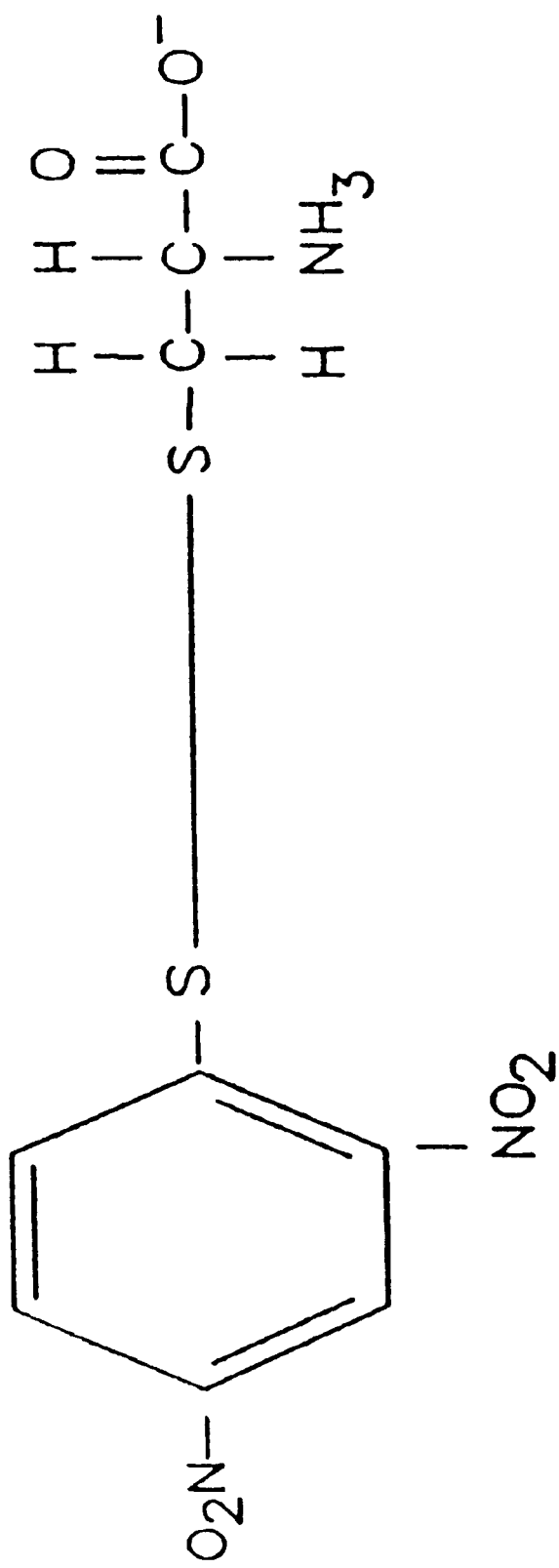
FIG. 5A–The structure of S-(2,4-Dinitrophenylthio $^{35}$S-Cysteine) or $^{35}$S-DNPTC is presented. The radioactive sulfur is shown in red.

The known functional defect in ISC β-actin with no observable structural change in the tryptic fragments generated from reduced HDSS, LDSS, and AA β-actin was problematical. The available thiols was measured in nonreduced native β-actin isolated from HDSS, LDSS, and AA erythrocytes (FIG. 4A). Thiol groups available in native β-actin were determined first with 5,5'-dithiobis-(2-nitrobenzoate) (DTNB). As shown in FIG. 4A when the β-actin samples were not incubated with reducing agent, the number of thiols per actin were 2.0 (AA), 1.2 (LDSS), and 0.2 (HDSS) (mol/mol). Whether the lack of titratable cysteine residues in HDSS β-actin was reversible upon incubation with reducing agent: dithiothreitol (DTT) was determined. The β-actin samples were reduced with buffer containing 0.2 mM DTT, and then the DTT removed prior to measurement of thiols with DTNB, and the results are shown in FIG. 4B. With reduced β-actin the number of titratable thiols became 2.0 (AA), 2.0 (LDSS), and 1.6 (HDSS). Therefore the lack of accessible cysteine residues in nonreduced HDSS β-actin was reversible with reducing agent, and therefore could not be explained by oxidation of cysteine to cysteic acid. The most reasonable explanation of these results is that a disulfide bridge is present between two of the six cysteine residues in HDSS (enriched in ISC) β-actin which is not present in control AA β-actin; an alternative explanation being that the two cysteines are blocked by some other mechanism that is reversible with DTT. The determination of exposed thiols with DTNB was performed twice with β-actin samples from four SS subjects with virtually identical results. Furthermore the same results were obtained when S-2,4, dinitrophenylthio $^{35}$S-cysteine ($^{35}$S-DNPTC) (FIG. 5A) was utilized as the thiol reactive reagent.

Next, it was important to identify the two cysteines which were available to labelling by $^{35}$S-DNPTC in AA β-actin but unavailable in nonreduced HDSS β-actin. S-(2,4-dinitrophenylthio) $^{35}$S-cysteine ($^{35}$S-DNPTC) which has been demonstrated to specifically label exposed thiols utilizing skeletal muscle actin as substrate (Fontana et al, 1968, Drewes and Faulstich, 1990) was synthesized. The advantage of this reagent is that it: (1) introduces by disulfide exchange [$^{35}$S] cysteine as a label to exposed thiols within actin, (2) these [$^{35}$S] cysteinyl-peptide bonds are not broken during trypsin digestion or reverse phase HPLC, (3) the addition of the [$^{35}$S]-cysteinyl residue does not change the elution properties of peptides perceivably in reverse phase HPLC, as preliminary experiments with the model peptides demonstrated, and (4) the release of 2,3-dinitrothiophenolate allows the efficacy of labelling to be followed by absorbance at 408 nm. The entire sequence of human β-actin is known (FIG. 5B), and it contains six cysteine residues at residues 16, 216, 256, 271, 284, and 373. (In the nomenclature of Vandekerckhove and Weber (1978) these six β-actin cysteines are numbered 17, 217, 257, 272, 285, and 374 based on alignment with the skeletal muscle actin sequence). Based on the known sequence there should be five tryptic peptides within β-actin which contain cysteine residues (shown in red in FIG. 5B). Six cysteine containing synthetic peptides shown in TABLE I were synthesized. Both KCF (372–374) and CF (373–374) were synthesized because it was not clear whether trypsin would cleave at both $R^{371}$ and $K^{372}$ under these digestion conditions. The strategy was that $^{35}$S DNPTC should label two cysteines in AA β-actin and after trypsin digestion and reverse phase HPLC should yield two radiolabelled tryptic peptides which will co-elute with two S-($^{35}$ S-cysteinyl)-synthetic peptides. Furthermore the $^{35}$S-cysteinyl-labelled tryptic and synthetic peptides eluted from reverse phase HPLC should contain predicted molecular mass ions on FAB-MS.

TABLE 1

CYSTEINE CONTAINING PEPTIDES

| Peptide Sequence | Residues | [M + H]$^+$ | S-($^{35}$S-cysteinyl)-[M + H]$^+$ |
|---|---|---|---|
| CF | | 373–374 | 269–388 |
| KCF | | 372–374 | 397–516 |
| CDVDIR | (SEQ ID NO:1) | 284–289 | 720–839 |
| DDDIAALVVDNGSGMCK | (SEQ ID NO:2) | 1–17 | 1723–1842 |
| LCYVALDFEQEMATAASSSSLEK | (SEQ ID NO:3) | 215–237 | 2494–2613 |
| CPEALFQPSFLGMESCGIHETTFNSIMK | (SEQ ID NO:4) | 256–283 | 3119–3238 |

Figure 6A:
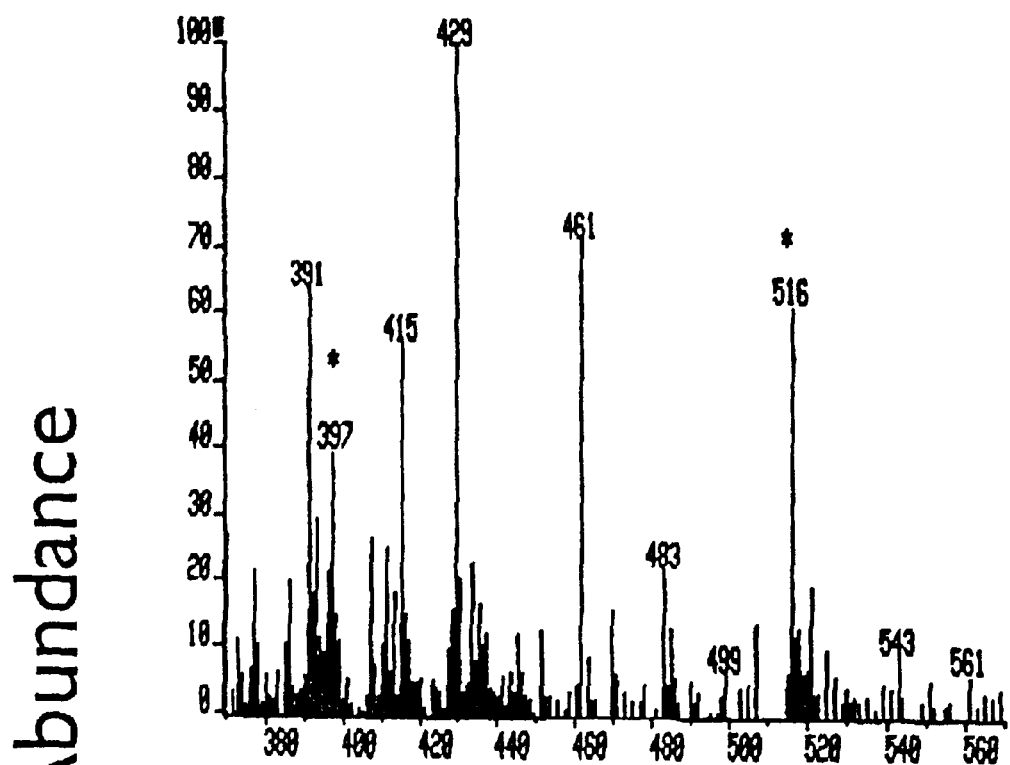
FIG. 6 shows a demonstration that cysteine$^{284}$ within CDVDIR (SEQ ID NO:1) and cysteine$^{373}$ within KCF are the reactive thiols in intact AA β-Actin.
FIG. 6E—Intact AA β-actin and synthetic peptides KCF, CDVDIR, (SEQ ID NO:1), and -DDDIAALVVDNGSGMCK (SEQ ID NO:2) were labeled with $^{35}$S-DNPTC as described below. S-($^{35}$S-cysteinyl)-β-actin was cleaved with trypsin and the resulting S-($^{35}$S-cysteinyl)-actin peptides were separated by reverse phase HPLC and 50 μl of each fraction was measured for radioactivity. S-($^{35}$S-cysteinyl)-KCF, -CDVDIR, and -DDDIAALVVDNGSGMCK were injected into the identical $C_{18}$ column and separated by reverse phase HPLC. Again 50 μl of each fraction was counted for radioactivity. The S-($^{35}$S-cysteinyl)-actin peptide peaks in fraction 17/18 and fraction 21, elute in the same position as the synthetic S-($^{35}$ S-cysteinyl)-KCF and synthetic S-($^{35}$S-cysteinyl)-CDVDIR. FAB-MS was conducted on fraction 17 from the reverse phase HPLC separation of synthetic S-($^{35}$S-cysteinyl)-KCF (FIG. 6A) and fraction 17 from S-($^{35}$S-cysteinyl)-actin peptides (FIG. 6B). The molecular ions with asterisks are KCF (397) and S-($^{35}$ S-cysteinyl)-KCF (516). FAB-MS was also conducted on fraction 21 from the reverse phase HPLC separation of synthetic S-($^{35}$S-cysteinyl)-CDVDIR (FIG. 6C) and fraction 21 from S-($^{35}$S-cysteinyl)-actin peptides (FIG. 6D). The molecular ions with asterisks are CDVDIR (720) and S-($^{35}$S-cysteinyl)-CDVDIR (839).
Figure 6B:
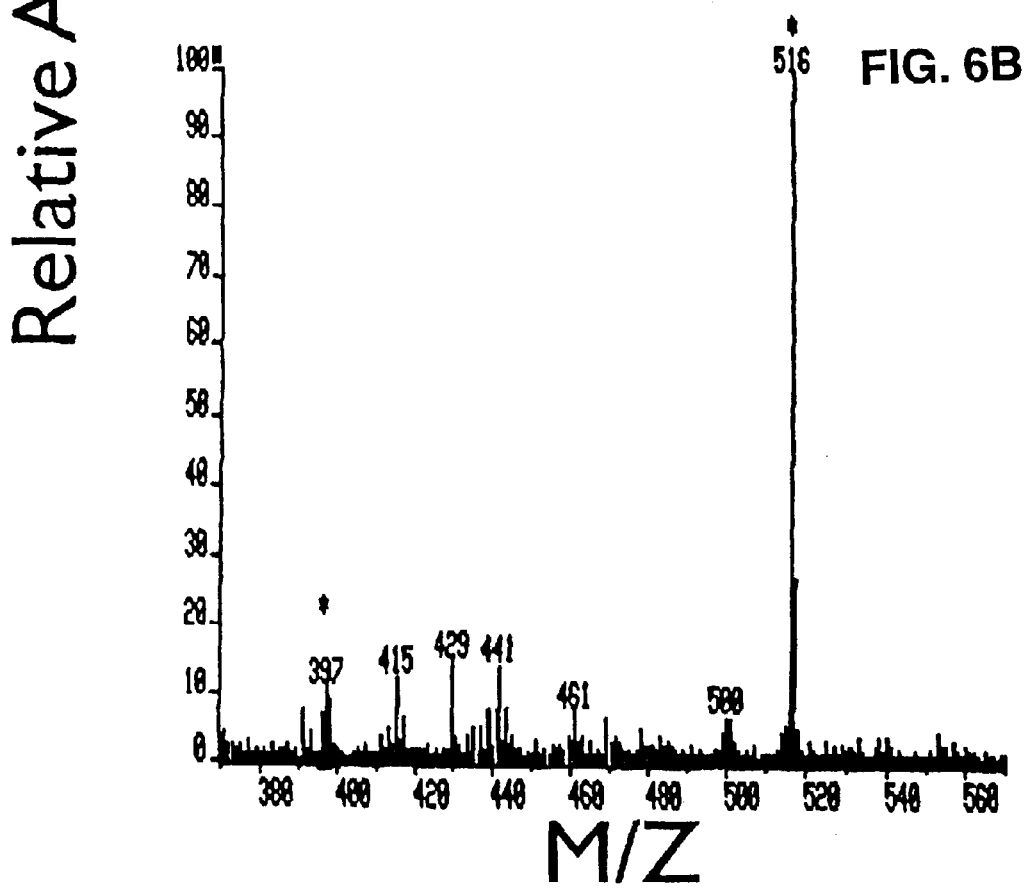
Figure 6C:
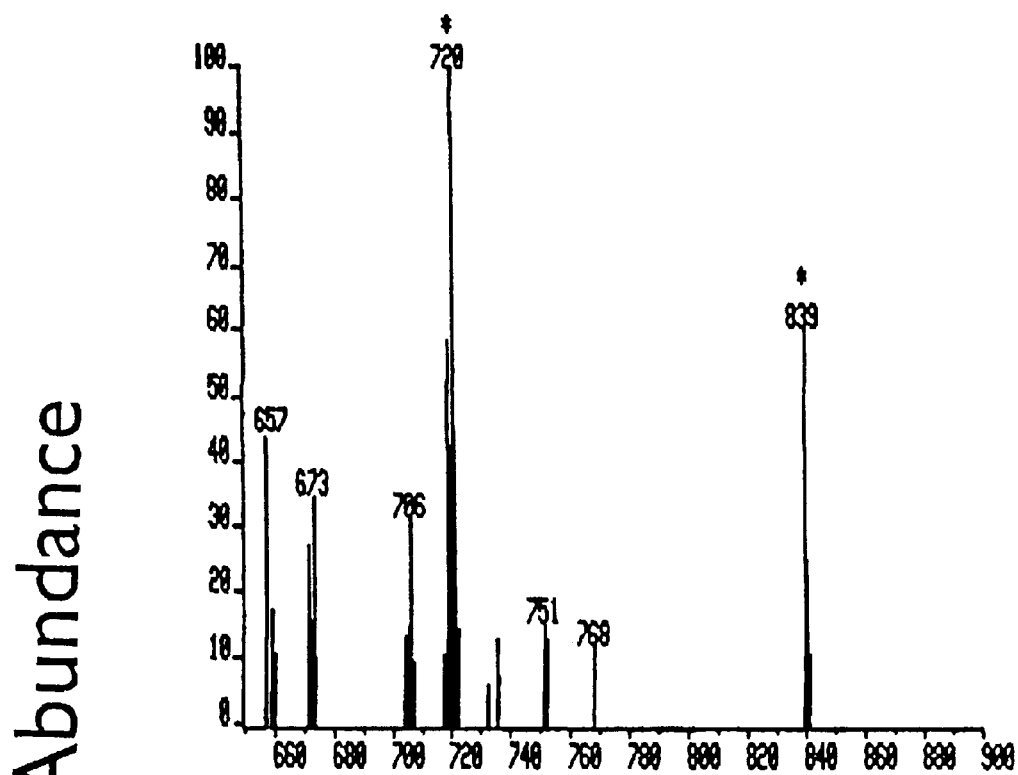
Figure 6D:
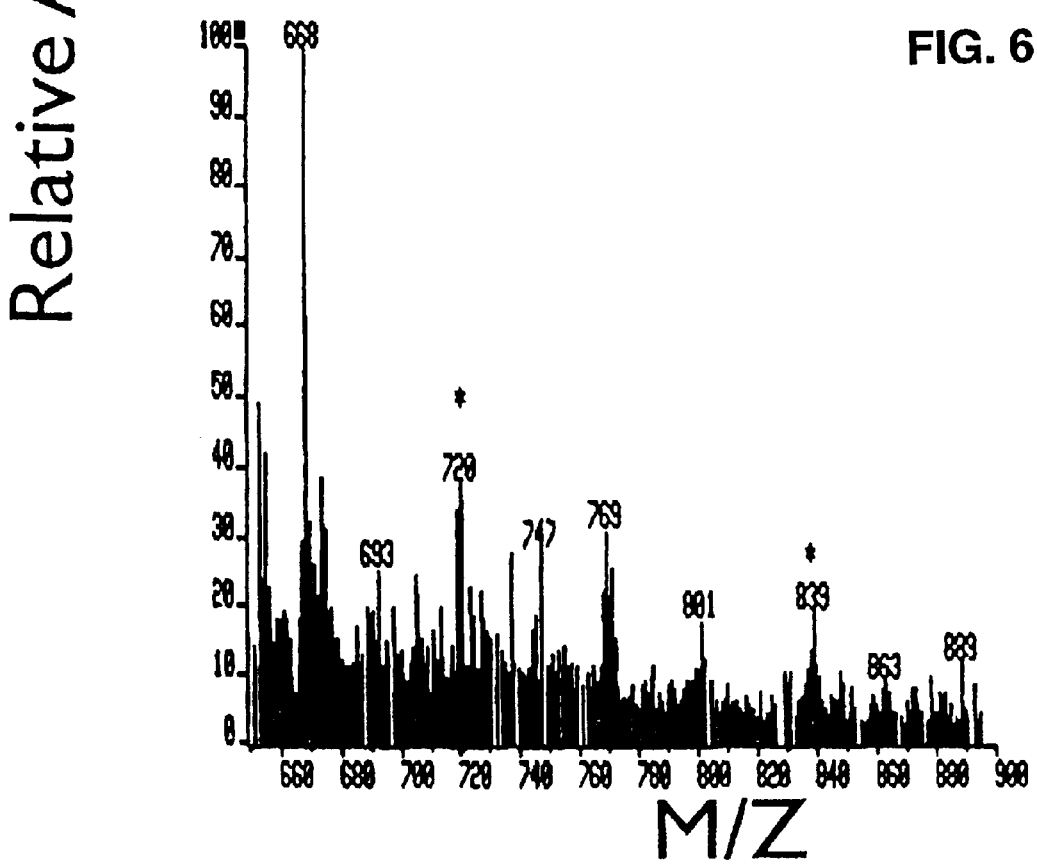
Figure 6E:
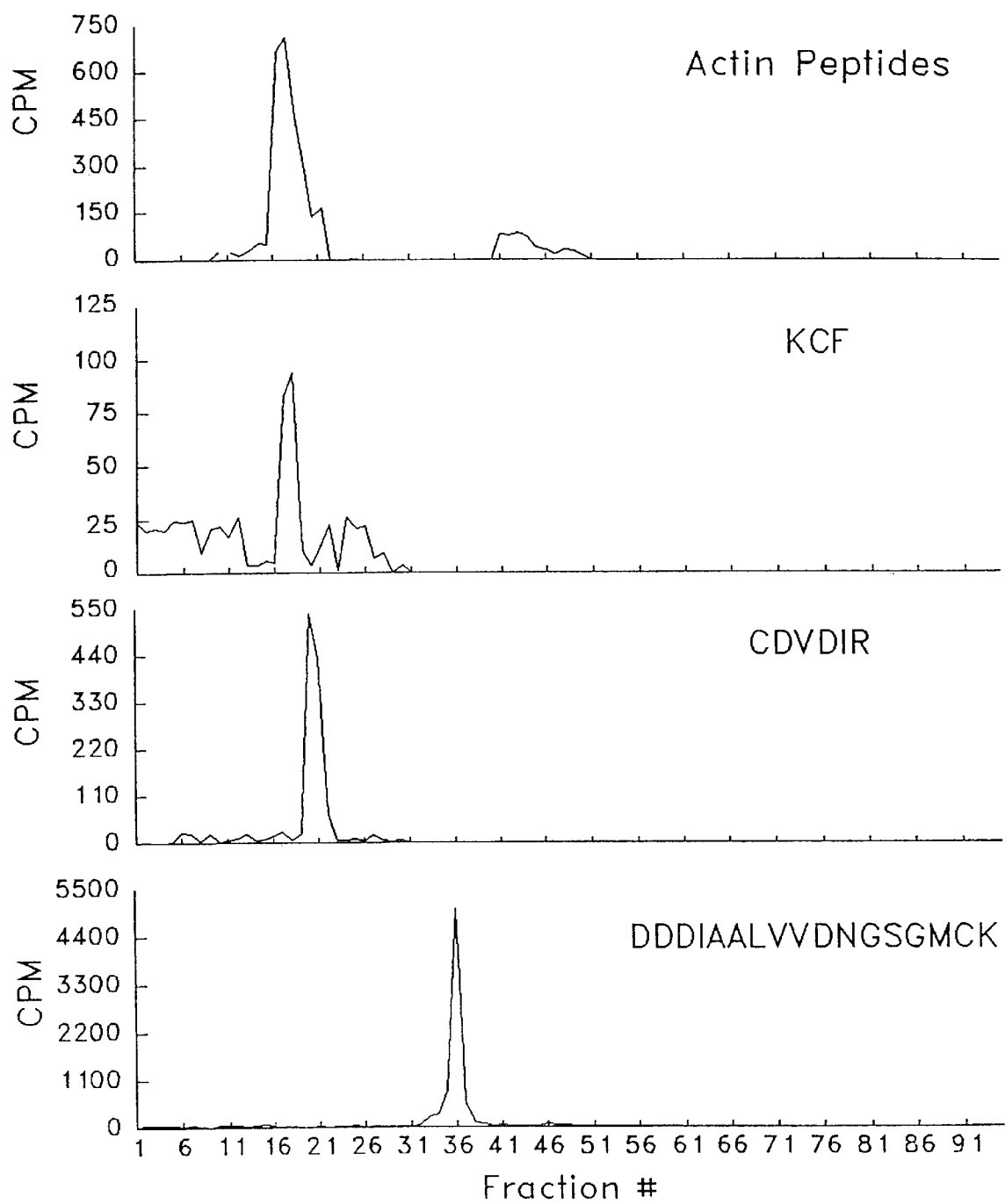

The results of the approach described above are presented in FIG. 6. AA β-actin was labelled with $^{35}$S-DNPTC, digested with trypsin, separated the tryptic fragments by reverse phase HPLC, and determined radioactivity in the fractions. Control AA β-actin had two S-($^{35}$S-cysteinyl)-tryptic peptides, eluting at fractions $^{17}/_{18}$ and 21 (FIG. 6E). The broad low peak in fractions 41–56 represents labelling of trypsin because it was observed in control samples which contained trypsin but no β-actin. HDSS actin labelled with $^{35}$S-DNPTC, digested with trypsin, and separated on reverse phase HPLC, demonstrated no labelling of tryptic peptides as expected (data not shown). Of the six cysteine containing synthetic peptides, shown in TABLE I, only residues 1–17, 284–289, 372–374, and 373–374 were soluble in the aqueous buffers. When these soluble synthetic peptides were labelled with $^{35}$S-DNPTC and injected into reverse phase HPLC S-($^{35}$S-cysteinyl)-$^{372}$KCF$^{374}$ and S-($^{35}$S-cysteinyl)-$^{373}$CF$^{374}$ eluted in fractions $^{17}/_{18}$ (S-($^{35}$S-cysteinyl)-KCF is shown in FIG. 6). S-($^{35}$S-cysteinyl)-$^{284}$CDVDIR$^{289}$ eluted at fraction 21, and S-($^{35}$S-cysteinyl)-$^{1}$DDDIAALVVDNGSGMCK$^{17}$ eluted at fraction 36. Thus, the reverse phase HPLC elution, shown in FIG. 6E, that the two tryptic peptides labelled with $^{35}$S-DNPTC in AA β-actin are probably KCF (or CF) and CDVDIR (SEQ ID NO:1). That this conclusion is correct was demonstrated by the FAB-MS spectra shown in FIGS. 6A–6D. Fraction 17 from $^{35}$S-DNPTC labelled synthetic KCF (FIG. 6A) and labelled AA β-actin tryptic peptides (FIG. 6B) yielded molecular ions of 397 and 516 on FAB-MS spectrum. The molecular ion of 397 corresponds to [M+H]$^+$ for KCF and 516 represents [M+H]$^+$ for S-($^{35}$S-cysteinyl)-KCF. The identification of the molecular ion of 516 as S-($^{35}$S-cysteinyl)-KCF was further confirmed by MS/MS tandem spectroscopy. Fraction 21 from $^{35}$S-DNPTC labelled synthetic CDVDIR (FIG. 6C) and labelled β-actin tryptic peptides (FIG. 6D) yielded molecular ions at 720 and 839 on FAB-MS spectrum. The molecular ion at 720 correspond to [M+H]$^+$ for CDVDIR and 839 represents [M+H]$^+$ for S-($^{35}$S-cysteinyl)-CDVDIR. Thus, the two cysteines which are labelled with thiol reactive reagents are $C^{284}$ and $C^{373}$ of control AA β-actin. These cysteines are not available in HDSS β-actin, unless this actin is pretreated with reducing agent.

Figure 7A:
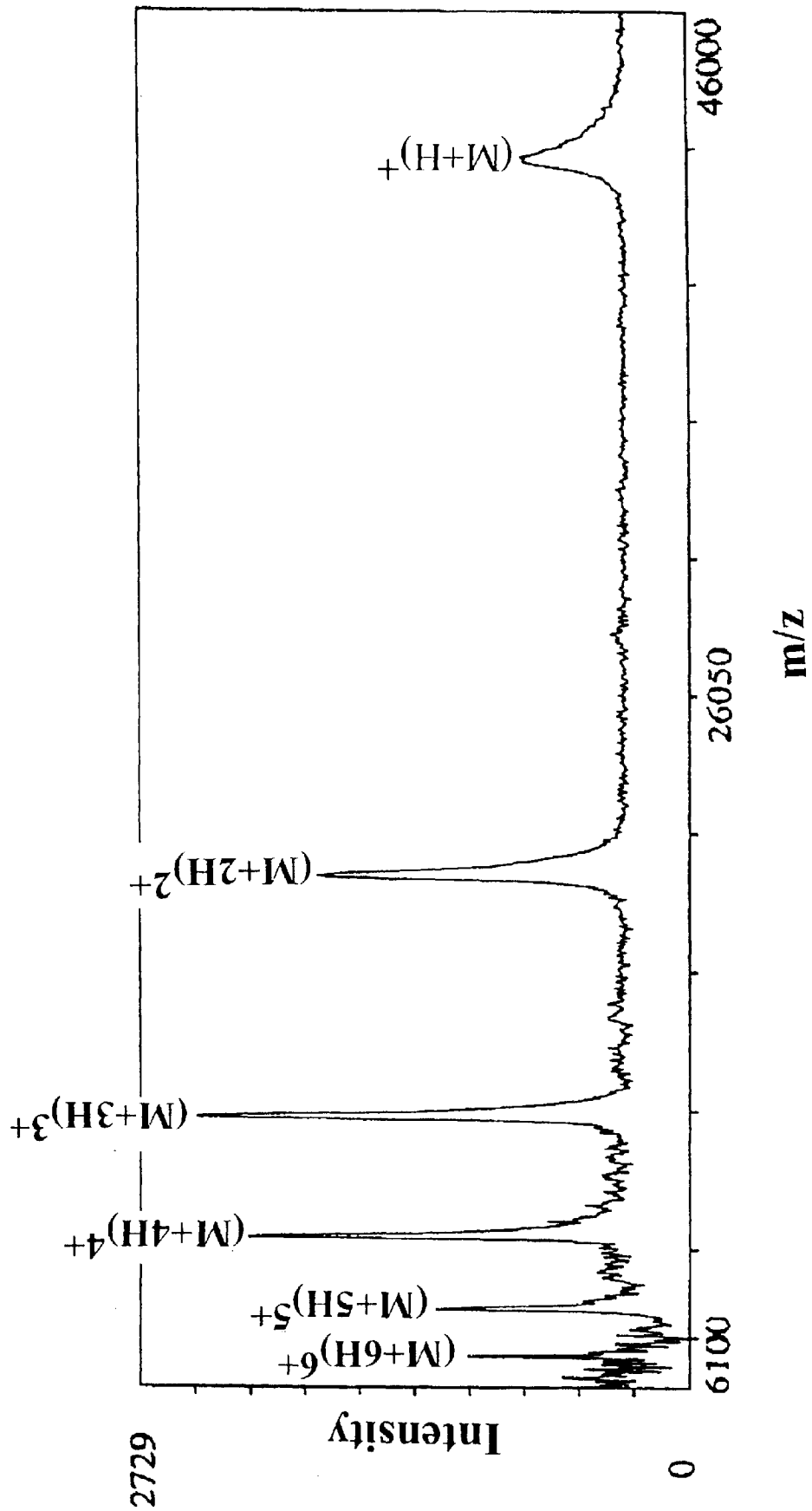
FIG. 7 shows the molecular weight determination of β-actin from MALDI-TOF spectra. MALDI-TOF mass spectra of β-actin isolated from control AA erythrocytes (FIG. 7A) and HDSS erythrocytes (FIG. 7B). The molecular weights were 41,690±100 and 41,760±100 respectively.
Figure 7B:
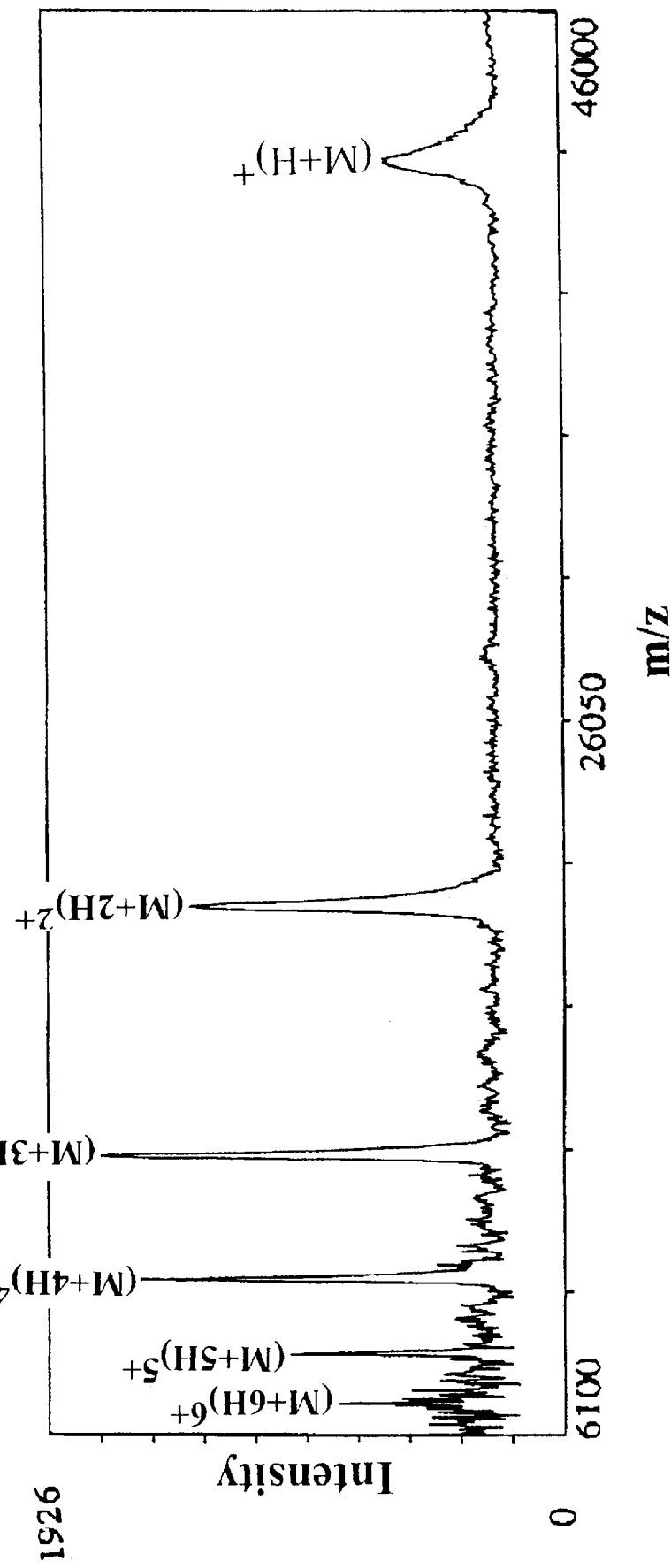

Thus, in HDSS β-actin (highly enriched in ISC β-actin) a disulfide bridge exists between cysteine$^{284}$ and cysteine$^{373}$ making these cysteines unavailable for reaction with DTNB or $^{35}$S-DNPTC. Upon reduction with DTT the disulfide bridge is broken, making HDSS β-actin like AA β-actin in having 2 accessible thiols per actin molecule. While this is the most plausible explanation, it was possible that some other posttranslational modification of ISC β-actin could cause a burying of cysteine$^{284}$ and cysteine$^{373}$. This modification would have to be reversible with reducing agent, and evaded detection in the previous FAB-MS analysis of tryptic fragments of HDSS versus AA β-actin. While this was a less likely scenario, it could be tested by matrix-assisted laser desorption ionization (MALDI) with a time of flight (TOF) instrument. The molecular weight of nonreduced AA β-actin and HDSS β-actin (FIGS. 7A and 7B respectively) was measured by MALDI-TOF mass spectroscopy. The molecular weights were identical within the accuracy of the measurement: 41, 760±100 daltons (HDSS β-actin) and 41, 690±100 daltons (AA β-actin). These results are consistent with a modification that altered the molecular weight by less than 100 daltons. Formation of a disulfide bridge, which would cause a change of only 2 mass units, certainly falls within this range. If any other modification exists it would have to change the molecular weight of the protein by less than 100 mass units. The experimentally determined molecular weights of HDSS and AA β-actin are consistent within the error of measurement with the molecular weight calculated from the known amino acid sequence (41,605.6 dal) plus $D^1$ acetylation (42 dal) and $H^{72}$ methylation (14 dal) (Nakajima-Iijima et al, 1985).

EXAMPLE 18
Reagents and Synthetic Processes

Formic acid, dithiothreitol (DTT), trypsin (TPCK treated) were purchased from Sigma Chemical Company (St. Louis, Mo.). 2,4-dinitrophenyl sulfenychloride (DNPS-CI) from Aldrich (Milwaukee, Mich.), toluene (ultrapure) from Alfa Products (Ward Hill, Mass.) and tetrahydrofurane (HPLC grade) from J. T. Baker (Phillipsburg, N.J.).

KCF and CDVIR (SEQ ID NO:1) peptides, representing tryptic fragments of actin, were produced by solid phase synthesis using FMOC chemistry on a Model 431 a peptide synthesizer (Applied Biosystems, Foster City, Calif.). The identity of the peptides were ascertained by FAB-MS after purifying them by reverse phase HPLC (System Gold, Beckman Instruments, Palo Alto, Calif.) using a standard 0.1% TFA and 80% acetonitrile with 0.1% TFA gradient.

KCF-CDVDIR disulfide bridge complex was synthesized in two steps using arylsulfenylhalide chemistry (Fontana et al., 1968a), following a described protocol (Drewes et al, 1990) with the necessary modifications for low mg batch size. Briefly, one of the peptides (KCF) was activated in the first step: KCF 4 mg (10 μmol) was dissolved in 100 μl formic acid placed in a 5 ml conical centrifuge tube. DNPS-Cl 8 mg (34 μmol) dissolved in 300 μl was added into the tube while gently shaking and occasionally sonicating. After 1 hour reaction period, 200 μl tetrahydrofurane and 600 μl toluene was added, then an additional 2 ml toulene. The reaction mixture was shaken and centrifuged for 5 minutes at 2,500 rpm. The toulene/tetrahydrofurane above the oily sediment was discarded, and the residue was dissolved in 60 μl tetrahydrofurane. Toluene 500 μl was added while shaking the vial. After centrifugation, the organic solvent-layer was discarded, and the precipitate dried in air (5.0 mg, 83% yield). Before use, the residue was dissolved in 250 μl methanol (20 μg/μl). Mass spectra were generated from 1 μl methanolic solution using glycerol matrix (MW: 594).

The second step of the synthetic procedure was the coupling of the activated peptide (DNPT-KCF) to the second peptide CDVDIR (SEQ ID NO:1): 1 mg CDVDIR (MW:566) was dissolved in a 2 ml glass vial by 50 μl 10 mM NH$_4$CO$_3$ buffer (20 μg/μl), pH =8.0. 1 μl of this solution was added onto the FAB probe tip which was holding 3–4 μl glycerol. After the mass spectra were recorded, 1–2 μl solution of the activated KCF was added onto the probe tip and carefully mixed with the CDVDIR containing matrix. The disulfide-linked KCF-CDVDIR peptide forms immediately, and the development of the yellow color signals the liberation of the dinitrothiophenolate. The entire 1 mg CDVDIR in the vial was similarly transformed by adding the proper amount of activated KCF solution (55 μl) to it. Judging from the rapid change of color, the reaction was complete within the first minute. Five minutes later, the reaction mixture was acidified with 10 μl 1% aqueous TFA (pH <2). In acidic solution, refrigerated at 4° C., the peptide was stable for months.

ISC β-actin was prepared from the high density fraction of RBC-s obtained from sickle cell anemia patients as described above. ISC actin was stored at 4° C. in a concentration of 150–200 μg/ml, and used within 48 hours of isolation.

EXAMPLE 19
Tryptic Digest and Reverse Phase HPLC: Peptide Map Generation

ISC β-actin was incubated with trypsin (50:1 actin:trypsin ratio) at pH 7.8, for 20 hr at 37° C. Digested actin was dried to a powder in a Speed-Vac instrument (Savant Instrument, Inc., Farmingdale, N.Y.), and then resuspended in half of the original volume with HPLC buffer A (0.1% aqueous TFA). The actin digest was loaded onto a ODS 5 C$_{18}$ reverse phase column (4.6 mm×15 cm) with precolumn, and eluted using the Beckman System Gold HPLC. The following program was used: 5 minutes isocratic period with buffer A, followed by a gradient of 0–100% buffer B (0.1% TFA, 80% ACN) over 90 minutes. The flow rate was 1 ml/minutes and OD$_{215}$ was monitored. Fractions were collected with a frequency of 1 minutes/fraction and dried in the Speed-Vac prior to mass spectrometry (MS).

Mass Spectrometry-FAB-MS

A VG 70-250 SEQ hybrid tandem instrument equipped with a saddle-field FAB gun and a continuous-flow fast atom bombardment (CF-FAB) probe was used for the MS analyses. The probe was modified by attaching a micro sample injector (Rheodyne model 7520; Altech Assoc., Inc., Houston, Tex.) to it on a mounting plate fastened to the handle. The original 0.5 ul sample volume of the injector was increased to about 1.8 μl by enlarging the bore of the sample channel to 0.0225". This injection volume ensured a chromatographic peek-width at half-height of about 45 s, adequate for acquiring three spectra under the flow and scanning conditions used. A fused silica capillary (3 ft×50

μm, i.d., 400 μm OD,. RESTEK) led the CF-FAB supporting fluid (10% glycerol+10% methanol+80% $H_2O$) from the injector to the probe tip. The outstanding length of the capillary above the stainless steel probe tip surface was adjusted (0.1–0.3 mm) until stable ion peaks were observed on the oscilloscope. A 2.5 cm long, 3 mm wide filter paper strip coiled around the probe tip greatly increased the spectra stability. The supporting fluid to the injector was supplied by a syringe pump (model 100D; Isco Inc., Lincoln, Nebr.), through a PEEK tubing (1/16" OD, 0.010"ID) with a rate of 4 μl/minutes that required a pump pressure of ~100 psi, and resulted in a source pressure of $3 \times 10^{-4}$ mbar ($2.5 \times 10^{-1}$ mbar at the source fore pump).

The MS source temperature was kept at 45° C., and the source potential (the ion-accelerating voltage) at 6kV. Xenon was used for the generation of the fast atom beam of 6 kV energy and 1 mA intensity. Positive ion mass spectra were recorded in the mass range of 200–1300 rate of 5 s/decade (~4 s/scan).

For the MS analysis, each peptide fraction was dissolved in 15 μl supporting fluid that contained 0.1% trifluoroacetic acid. The injector with the 1.8 μl sample chamber was loaded using 2.5 μl sample volumes, and injections were made in 10 scans intervals. The injector was carefully flushed with supporting fluid between samples (2×4 μl before loading, 2×4 μl after injection).

Tandem Mass Spectrometry

For obtaining MSMS spectra, first (sector) MS was focused to transmit to precursor (parent) ion selected from the primary mass spectrum. The ICP (Instrument Control Parameters) program module of the data system was used in this process, and it required one injection of the sample. After focusing the sector MS, the ion signals from the second (dual quadrupole) MS were observed: the transmission of the parent ion and the occurrence of the product ions were checked on the oscilloscope. The resolution, analyzer energy (pole-bias), and collision energy dials were slightly adjusted to decrease the original intensity of the precursor ion by half. The pressure reading at the ion gauge of the associated diffusion pump was $1 \times 10^{-6}$ mbar. The collision energy was between 5 and 15 V. The protonated molecular ion of Leu-Enkephalin (mz 556) was used for instrument tuning under static FAB-MS conditions, and injections of 100 ng/μl Leu-Enkephalin solution were used to verify the optimal settings for the CF-FAB experiments. The analyzer quadrupole was scanning with a speed of 10 s/spectrum in the mass range of 200–1200 D, and the MS/MS spectra were recorded in MCA (multiple channel analyzer) format: 8–10 continuum spectra at the elution-maximum of the sample were summed, then the resulting spectrum processed (smoothed, peak-detected, and mass converted) in the usual, mass vs relative abundance, bar diagram format.

Synthetic Disulfide Linked Peptide KCF-CDVIR

In order to prove the existence of the disulfide bond in ISC β-actin one has to demonstrate the presence of the correlated KCF-CDVDIR cystine-peptide in the tryptic digest. To accomplish this, the peptide was first synthesized, then its chromatographic and mass spectrometric (MS) characteristics were determined, and used these data for detection and identification.

The synthesis is based on the reaction of arylsulfenyl-chloride with cysteine, which was developed as a peptide/ protein modifying and cysteine residue protecting tool (Scoffone et al., 1968, Fontana et al., 1968 a,b). Arylsulfenyl halides such as 2-nitrophenyl-, or 2,4-dinitrosulfenylchloride react with the sulfhydryl groups of peptides and proteins in acetic or formic acid solvent producing an asymmetric disulfide compound as exemplified in FIG. 9, first reaction. The asymmetric aryl-alkyl disulfide is stable under moderately acidic conditions but rapidly decomposes in alkalic media (Fontana et al., 1968a). However, in the presence of another aliphatic sulfhydryl compound in the alkalic medium, a disulfide exchange occurs: the dinitrophenylthiophenol in the activated compound is replaced by the other aliphatic sulfhydryl compound. This reaction can be utilized to build disulfide-linked (asymmetric cystine-containing) peptides. Acetic acid and formic acid are excellent solvents for most peptides and many proteins, therefore cysteine containing peptides (such as KCF, FIG. 9, first reaction) can readily be activated by arylsulfenyl halides into a reactive intermediate (S-dinitrophenylthio-KCF). The reactive intermediate, as mentioned above, easily reacts with a second cysteine peptide in mildly alkalic medium (10 mM $NH_4HCO_3$, pH 8.0) producing the desired disulfide linked peptide (KCF-CDVDIR, FIG. 9, 2nd reaction). With the production of the S-S linked peptide, an equal amount of dinitrophenolate anion is liberated and the progress of the reaction may be followed by monitoring the development the yellow color ($_{-408}$=12,700 $mol^{-1}cm^{-1}$).

The reactions were also followed by mass spectrometry using the conventional ("static") probe with the FAB technique (FIG. 10). FIG. 10A presents KCF before activation with the dominant molecular ion being m/z 397 ($MH^+$). The activated compound DNPT-KCF is presented in FIG. 10B. Beside the dominant m/z 595 ($MH^+$), the molecular ion of the original non-derivatized KCF also appears in meaningful abundance. This ion is an MS artifact: the FAB glycerol matrix reduced part of the disulfide peptide. Similar reducing reactions, e.g., dehalogenation of drugs, and demethylation of dyes have been discussed in the FAB-MS literature (Edom et al., 1991).

The third spectrum (FIG. 10C) presents the "second" peptide CDVDIR with a dominant molecular ion at m/z 720, and the bottom panel (FIG. 10D) presents the disulfide-coupled product KCF-CDVDIR. Beside the intense molecular ion of m/z 1114, the molecular ions of both reduced components m/z 720 (CDVDIR+H) and 397(KCF+H) are exhibited. The three molecular ion peaks are important diagnostic tools in locating this cysteine-peptide in the tryptic digest.

Further helpful diagnostic data is the HPLC retention time.

Figure 11A:
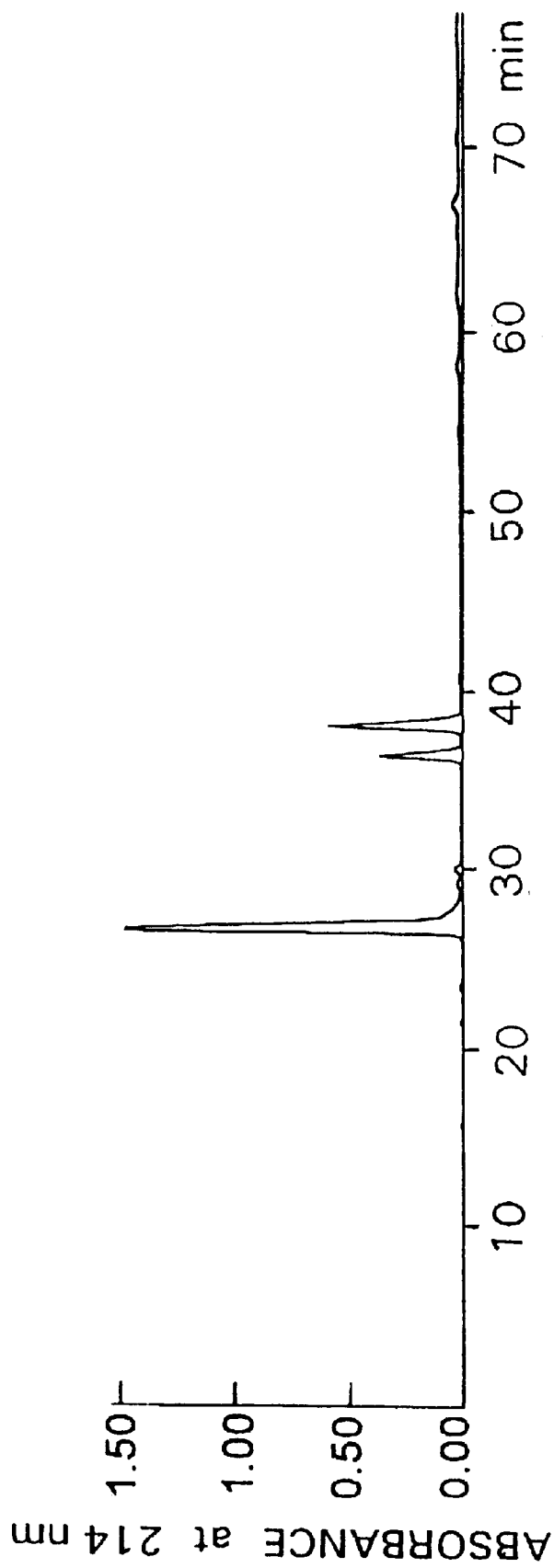
FIG. 11A shows an HPLC trace of the raw products of the coupling reaction between activated KCF and CDVDIR.

The chromatogram of the reaction product is shown in FIG. 11A. The mass spectra from the fractions collected from reverse phase HPLC were generated by the CF-FAB operation. The first peak with elution of 27 minutes from the HPLC is the desired compound KCF-CDVDIR, as the corresponding mass spectrum testifies (FIG. 3B; $MH^+$ at m/z 1114). The mass spectrum for the second peak(elution time of 37 minutes; FIG. 11C) corresponds to activated DNPT-CDVDIR, ($MH^+$ at m/z 918). The third peak (elution time of 38 minutes) is the activated peptide excess reagent DNPT-KCF (spectrum not shown here; it is identical to the one in FIG. 10B). The mechanism that generated the second eluting compound is disulfide bond exchange or "scrambling" between the product KCF-CDVDIR and the excess reagent (3rd peak) a reaction which usually takes place in alkalic medium (Fontana et al., 1968a). It is important for the stability of the product, that the pH of the solution be lowered to acidic values (pH-2–5) as soon as the coupling reaction is complete (1–5 minutes). The results of the disulfide bond exchange are seen also in the mass spectrum from the first HPLC peak (FIGS. 11A–11C), by the appearance of the symmetric cystine compounds' molecular ion m/z 791 (2KCF–2H+H). Since both molecular ions m/z 1114 and 791 appear in the same fraction, the two peptide-compounds KCF-CDVDIR and KCF-KCF must have nearly identical retention times. The KCF-CDVDIR spectrum prepared immediately after the coupling reaction (FIG. 10D) does not exhibit this impurity.

Identifying KCF-CDVDIR in the Tryptic Digest of ISC β-actin

If the coupling reaction was carefully completed, and quickly analyzed, one obtains only a single peak on the succeeding HPLC chromatography (FIG. 12A). The retention time of 27 minutes provides the window used to select promising fractions from the ISC β-actin tryptic peptide map (FIG. 12B). From the HPLC separation of the tryptic digest obtained from 250 ng (6 nmol) ISC actin, equivalent fractions were investigated by continuous-flow FAB-MS. All three diagnostic ion-peaks m/z 1114, 720 and 397 were found in the spectra presented in FIG. 12C. Although the ions of other peptides dominate the spectrum (e.g., MH of $T_{31}$: $^{316}$EITALAPSTMK$^{326}$ (SEQ ID NO:5), m/z 1162), the diagnostic ions are easily distinguishable.

The MSMS product ion spectra generated from the ISC β-actin tryptic molecular ion m/z 1114 (FIG. 12D) has convincing similarity to the MSMS spectrum prepared from the synthetic KCF-CDVDIR (FIG. 12E). The product ions present in both spectra, with definite structural meaning, are m/z 288: $Y''_2$, 502: $Y''_4$, and 1096: $B_6$, if KFC-C is considered as one residue. M/z 686 which appears in both spectra, was probably generated from m/z 720 (CDVDIR+H) by the loss of the $H_2S$ side-chain. The ion m/z 752 in the spectrum of the model compound (FIG. 12E) is probably holding both sulphur atoms from the parent molecular ion -S-S bridge. The similarity of the two spectra appears to be clear evidence of the identity of the two compounds they represent. That is, the β-actin from ISC RBC membranes does contain an S-S bridge between cysteine$^{284}$ and cysteine$^{373}$. These results are the first direct demonstration of a disulfide bridge between cysteine$^{284}$ and cysteine$^{373}$ in ISC β-actin.

Preparation Of Density Separated Red Blood Cells, Ghosts, And Core Skeletons

Density separation of blood obtained from nine homozygous SS subjects from eight independent families was performed using Percoll step gradients. Each density fraction within the Percoll layers was removed without cross contamination and then HDSS erythrocytes (70% Percoll), LDSS erythrocytes (45% Percoll), and control (AA) erythrocytes were washed two times in 50 ml PBS (10 mM NaPO$_4$, 150 mM NaCl, pH 7.6). Packed red blood cells were lysed in 30 ml of ice cold lysis buffer (5mM NaPO$_4$, 1 mM EDTA, pH 7.6) and ghosts were sedimented at 31,000×g for 15 minutes at 4° C. This procedure was repeated until the pellet became white or light pink. Freshly prepared AA, HDSS, and LDSS ghosts (50 µl of packed ghosts) were incubated in 9 volumes of high ionic strength Triton X-100 buffer (10 mM NaPO$_4$, 600 mM KCl, 1 mM ATP, 1 mM DFP, 1% Triton X-100, pH 7.6) for various times within a temperature controlled water bath. Upon completion of the extraction the samples were transferred to ice and centrifuged at $^{35,000}$×g for 45 minutes at 4° C. The pellets were resuspended to 50 µl in lysis buffer and were analyzed by SDS-PAGE.

SDS-PAGE

HDSS, LDSS, and AA ghosts (50 µg) and the core skeletons obtained from this concentration of ghost protein were analyzed by SDS-PAGE utilizing the discontinuous buffer system of Laemmli (15) and a 9% polyacrylamide separating gel. Protein was stained with coomassie brilliant blue and scanning densitometry performed with a Zeineh laser densitometer (Biomed Instruments, Inc.).

Computation and Statistical Analysis

For each temperature and various times of extraction we calculated the mean of three or more experimental values of percent of spectrin remaining in control, LDSS and HDSS core skeletons after extraction in Triton X-100 buffer. The amount of spectrin in the original ghosts (time zero) was set at 100%. First order rate constants of dissociation of spectrin was computed using the software package "Enzfitter", a non-linear regression data analysis program by Biosoft Co. The equation for the calculation was:

$$A = A_0 e^{-kt} \text{ or}$$

$$k = \frac{1}{t} \ln \frac{A_0}{A}$$

where $A_0$ is amount of protein at time zero, A is amount of protein at time t and k is the first order rate constant of dissociation. The statistical analysis was performed using a commercially available software package SAS (Statistical Analysis System).

The rate of dissociation of AA, HDSS, and LDSS core skeletons was determined at 0° C., 24° C., 30° C., 34° C., and 37° C. Red blood cell membranes were isolated from these three classifications of erythrocytes, and then extracted in high ionic strength Triton X-100 buffer for various times at fixed temperatures. For each temperature, an example is presented of the resulting SDS PAGE (FIGS. 13A, 14A, 15A, 16A and 17A) and densitometric analysis of spectrin remaining in the skeleton (FIGS. 13B, 14B, 15B, 16B and 17B). In TABLE 2, the mean±standard error, are presented for three to six independent experiments at each temperature, of the first order rate constants for spectrin's dissociation from the core skeleton.

TABLE 2

First order rate constants ($10^4$sec$^{-1}$) of dissociation of membrane skeletons at different temperatures

| Dissociation Membrane | temperature | | | |
|---|---|---|---|---|
| | 0° C. | 24° C. | 30° C. | 34° C. |
| AA | 0.035 ± 0.033 (4) | 3.78 ± 0.88 (3) | 11.15 ± 0.79 (6) | 47.50 ± 4.5 |
| LDSS | 0.035 ± 0.032 (4) | 1.75 ± 0.50 (3) | 9.72 ± 0.98 (6) | 40.50 ± 1 |
| HDSS | 0.030 ± 0.022 (4) | 0.83 ± 0.35 (3)* | 7.29 ± 0.99 (6)* | 20.67 ± 5. |
| AA + DTT | | | 11.01 ± 0.77 (3) | |
| LDSS + DTT | | | 11.05 ± 0.97 (3) | |
| HDSS + DTT | | | 9.78 ± 0.56 (3) | |

$^1$Mean ± standard error
*Denotes rate constants which are significantly different from the control (AA) values (P <0.05).

Figure 13A:
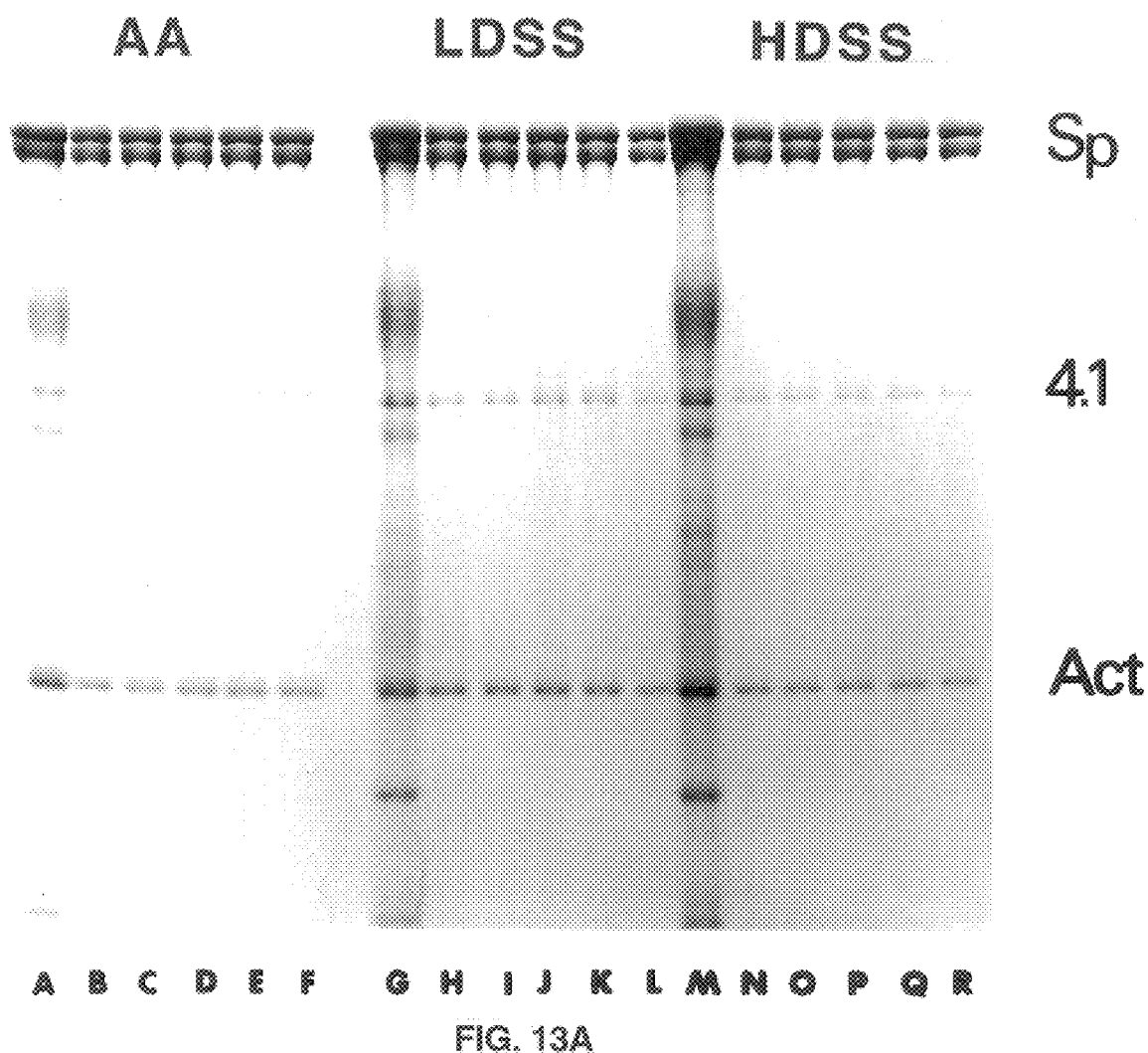
FIG. 13A—SDS PAGE of 50 μg of AA (A), LDSS (G), and HDSS (M) membrane protein; and core skeletons isolated from 50 μg of AA (B–F), LDSS (H–L), and HDSS (N–R) membranes. The skeletons were prepared by extraction in high ionic strength Triton X-100 buffer at 0° C. for 0.5 h (B, H, N), 1 h (C, I, O), 2 h (D, J, P), 3 h (E, K, Q), and 24 hr (F, L, R).
Figure 13B:
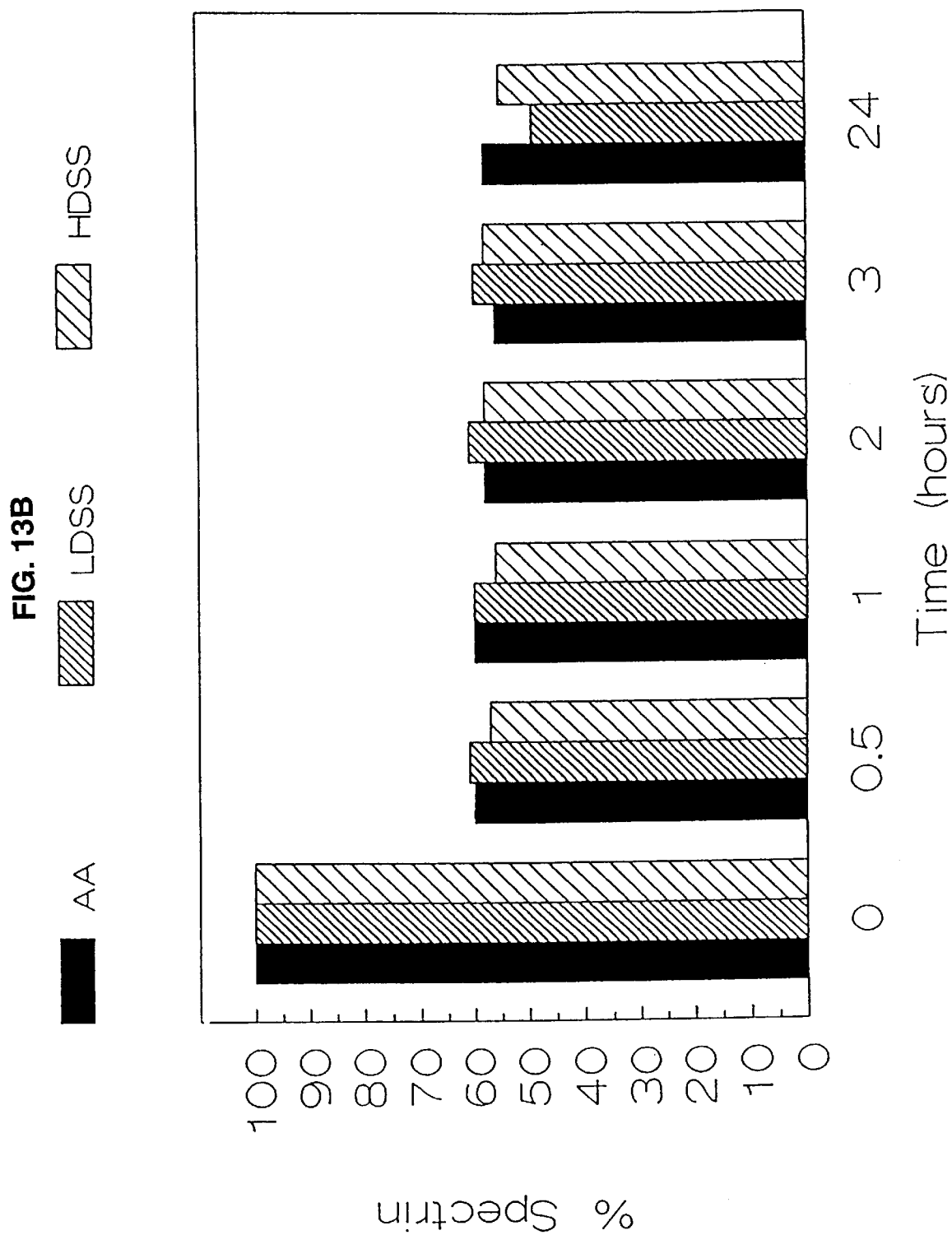
FIG. 13B—Densitometric analysis of the amount of spectrin remaining in the core skeletons at various times of extraction at 0° C. The amount of spectrin in the original ghosts (time zero) was set at 100%.
Figure 14A:
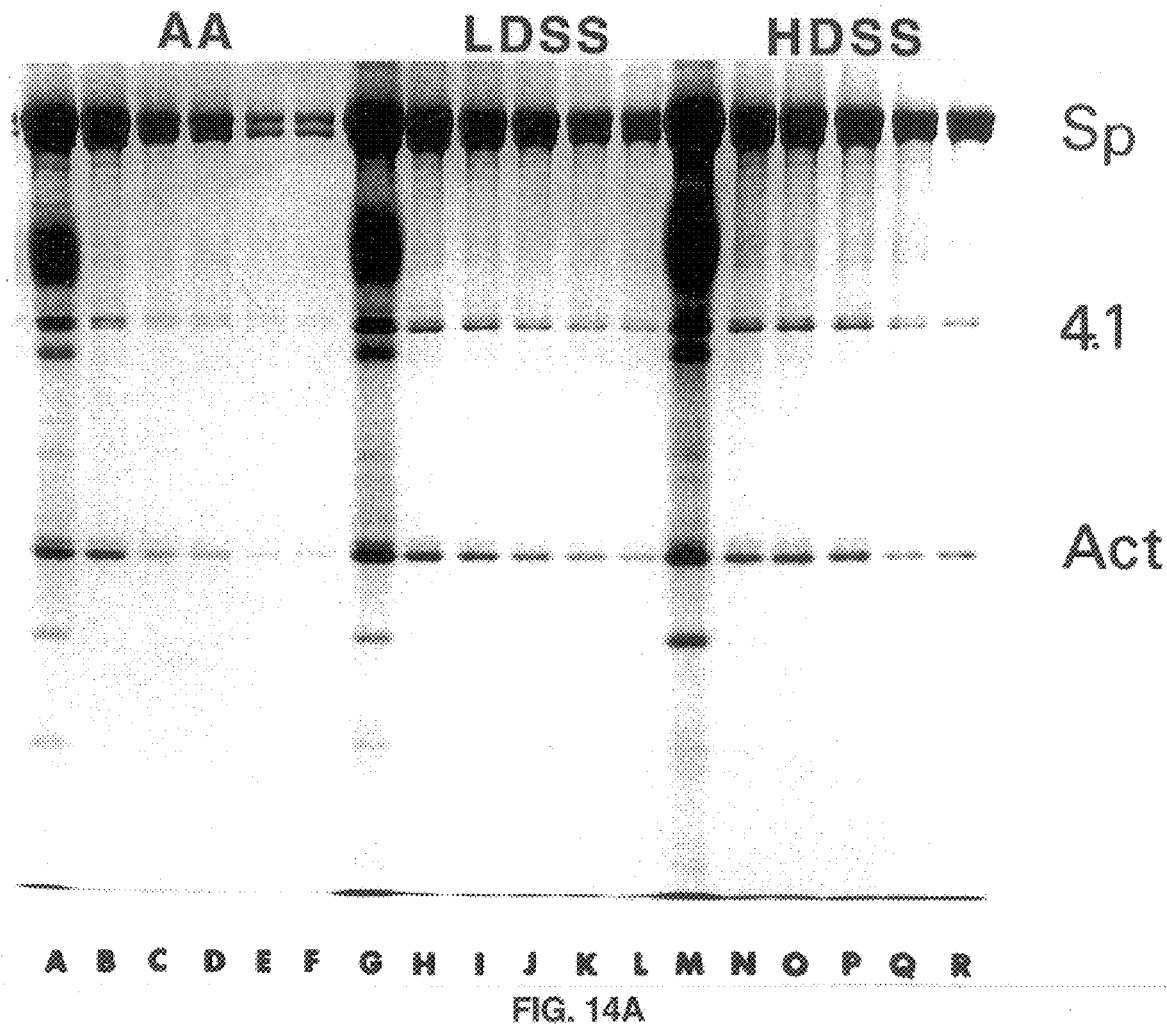
FIG. 14A—SDS-PAGE of 50 μg at AA (A), LDSS (G), and HDSS (M) membrane protein, and core skeletons isolated from 50 μg of AA (B–F), LDSS (H–L), and HI)SS (N–R) membranes. The skeleton were prepared by extraction in high ionic strength Triton X-100 buffer at 24° C. for 15 minutes (B, H, N), 30 minutes (C, I, O) 1 h (D, T, P), 2 h (E, K, Q), and 3 h (F, L, R).
Figure 15A:
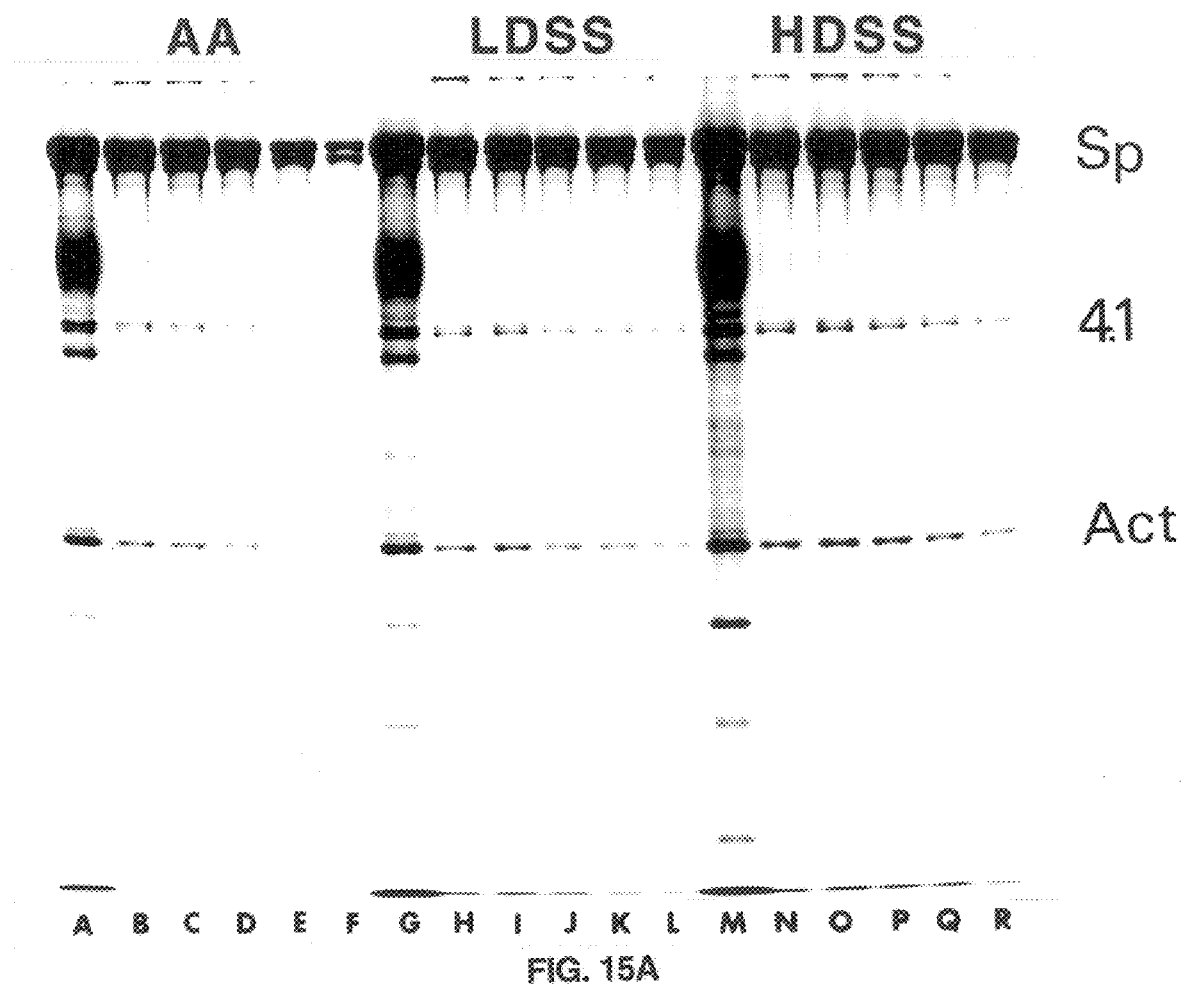
FIG. 15A—SDS-PAGE of 50 μg AA (A), LDSS (G), and HDSS (M) membrane proteins, and core skeletons isolated from 50 μg of AA (B–F), LDSS (H–L) and HDSS (N–R) membranes. The skeletons were prepared by extraction in high ionic strength Triton X-100 buffer at 30° C. for 5 minutes (B, H, N), 10 minutes (C, I, O) 15 minutes (D, T, P), 20 minutes (E, K, Q), and 25 minutes (F, L, R).
Figure 15B:
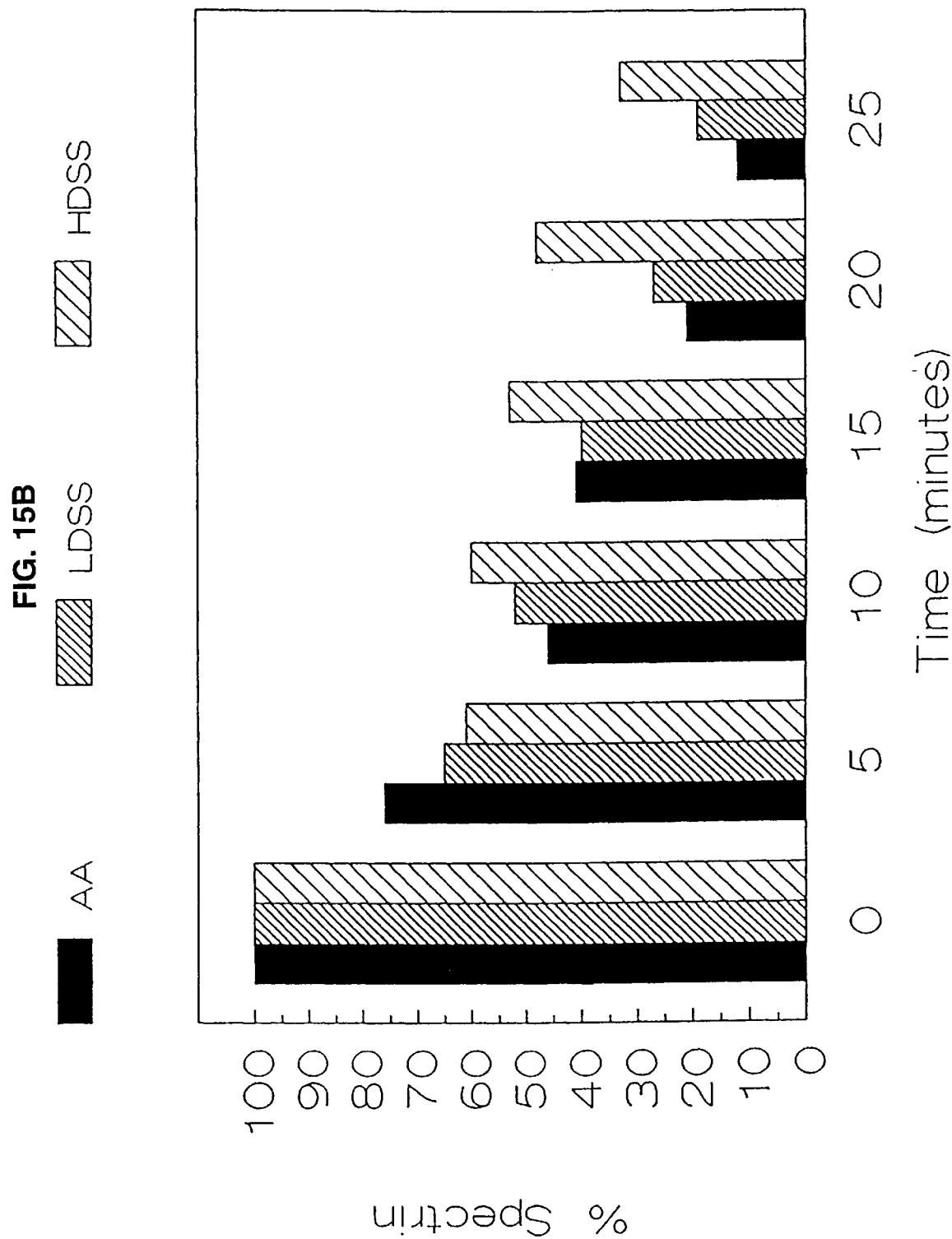
FIG. 15B—Densitometric analysis of the amount of spectrin remaining in the core skeletons at various times of extraction at 30° C. The amount of spectrin in the original ghosts (time zero) was set at 100%.
Figure 16A:
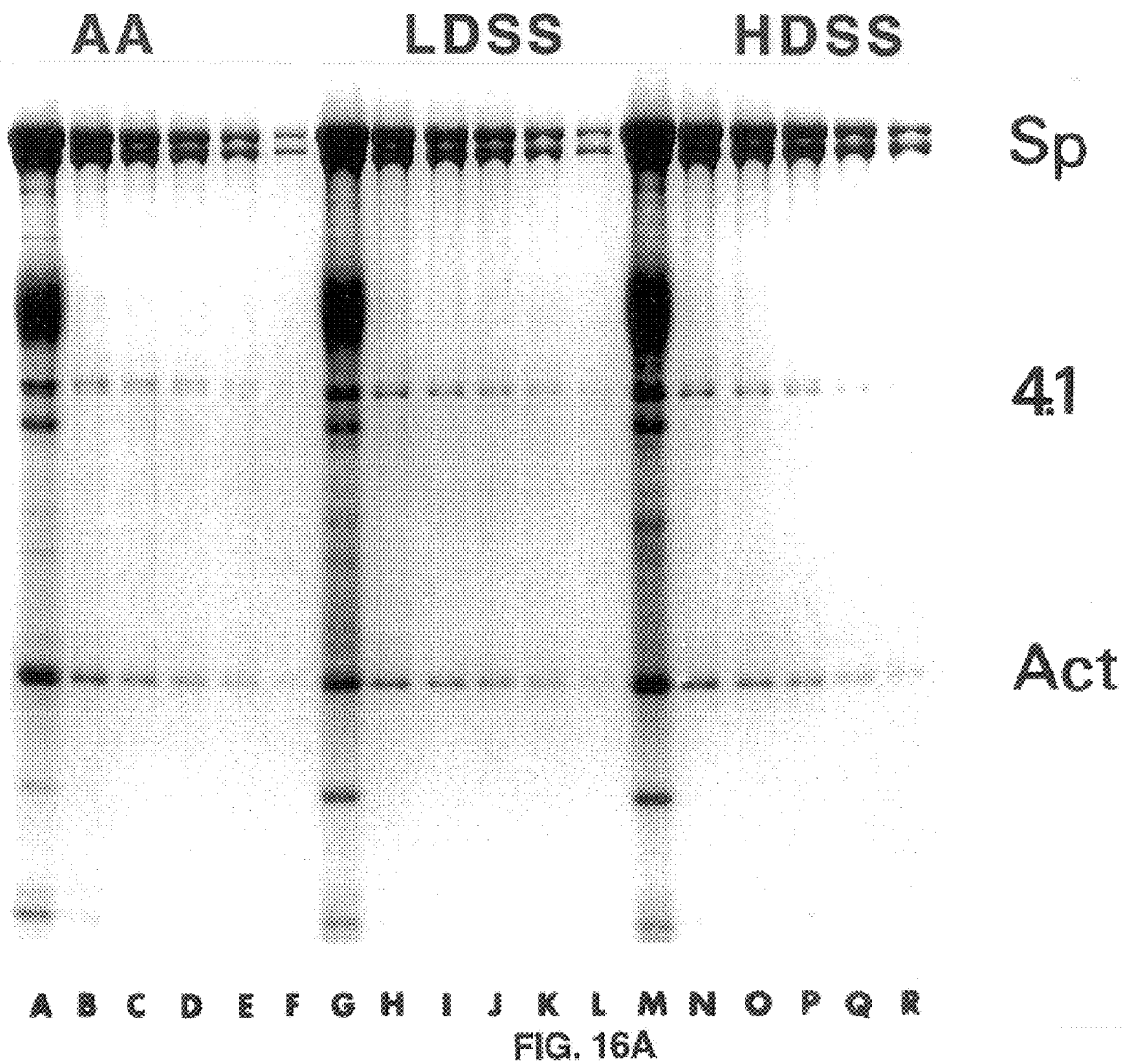
FIG. 16A—SDS-PAGE of 50 μg AA (A), LDSS (G), and HDSS (M) membrane proteins, and core skeletons isolated from 50 μg of AA (B–F), LDSS (H–L) and HDSS (N–R) membranes. The skeletons were prepared by extraction in high ionic strength Triton X-100 buffer at 34° C. for 1 minutes (B, H, N), 2 minutes (C, I, O) 4 minutes (D, T, P), 6 minutes (E, K, Q), and 8 minutes (F, L, R).
Figure 17A:
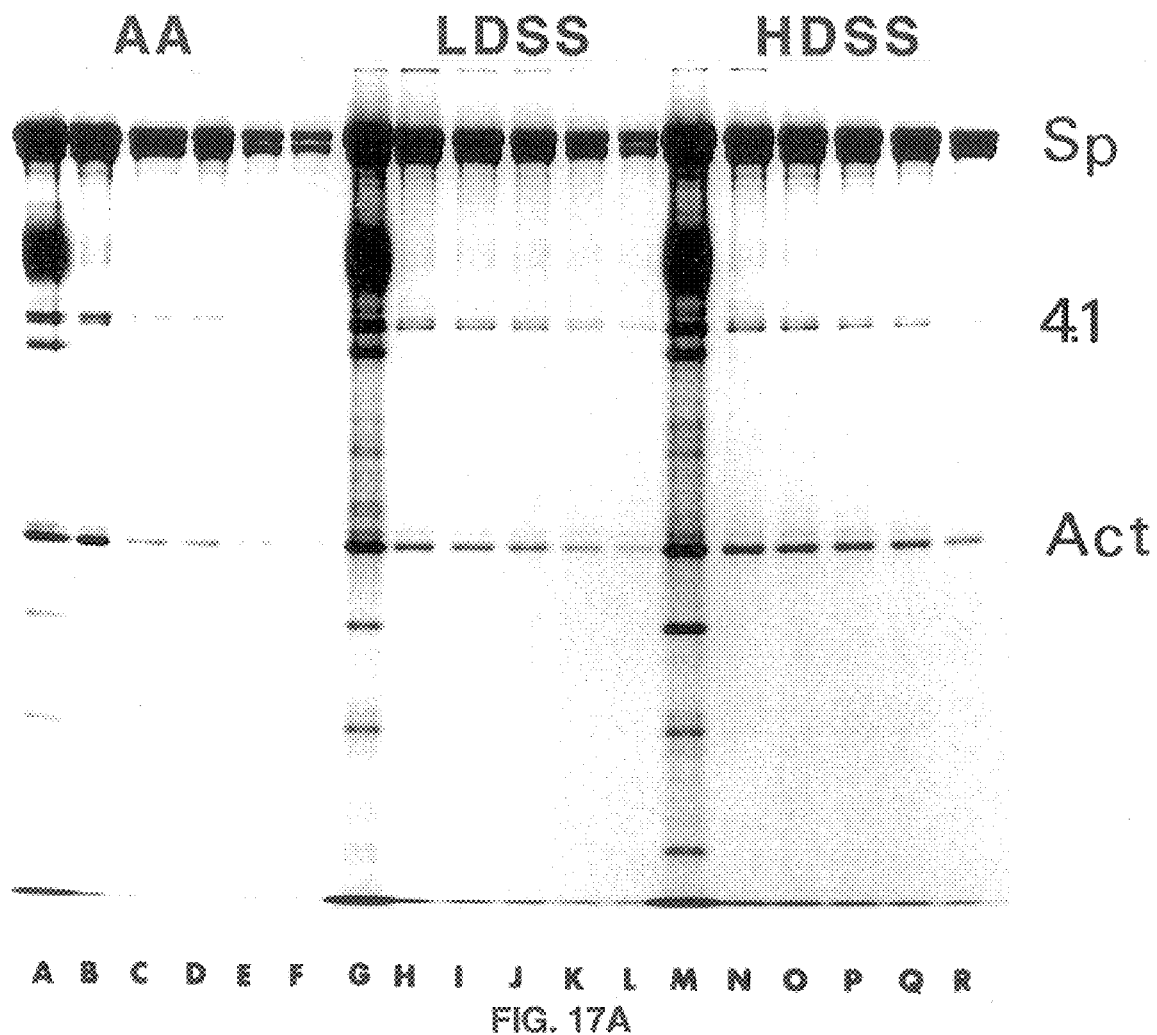
FIG. 17 shows the core membrane skeleton dissociation at 37° C. 17A—SDS-PAGE of 50 μg AA (A), LDSS (G), and HDSS (M) membrane proteins, and core skeletons isolated from 50 μg of AA (B–F), LDSS (H–1) and HDSs (N–R) membranes. The skeletons were prepared by extraction in high ionic strength Triton X-100 buffer at 37° C. for 1 minutes (B, H, N), 2 minutes (C, I, O) 2.5 minutes (D, T, P), 3 minutes (E, K, Q) and 3.5 minutes (F, L, R).
FIG. 17B—Densitometric analysis of the amount of spectrin remaining in the core skeletons at various times of extraction at 37° C. The amount of spectrin in the original ghosts (time zero) was set at 100%.
Figure 17B:
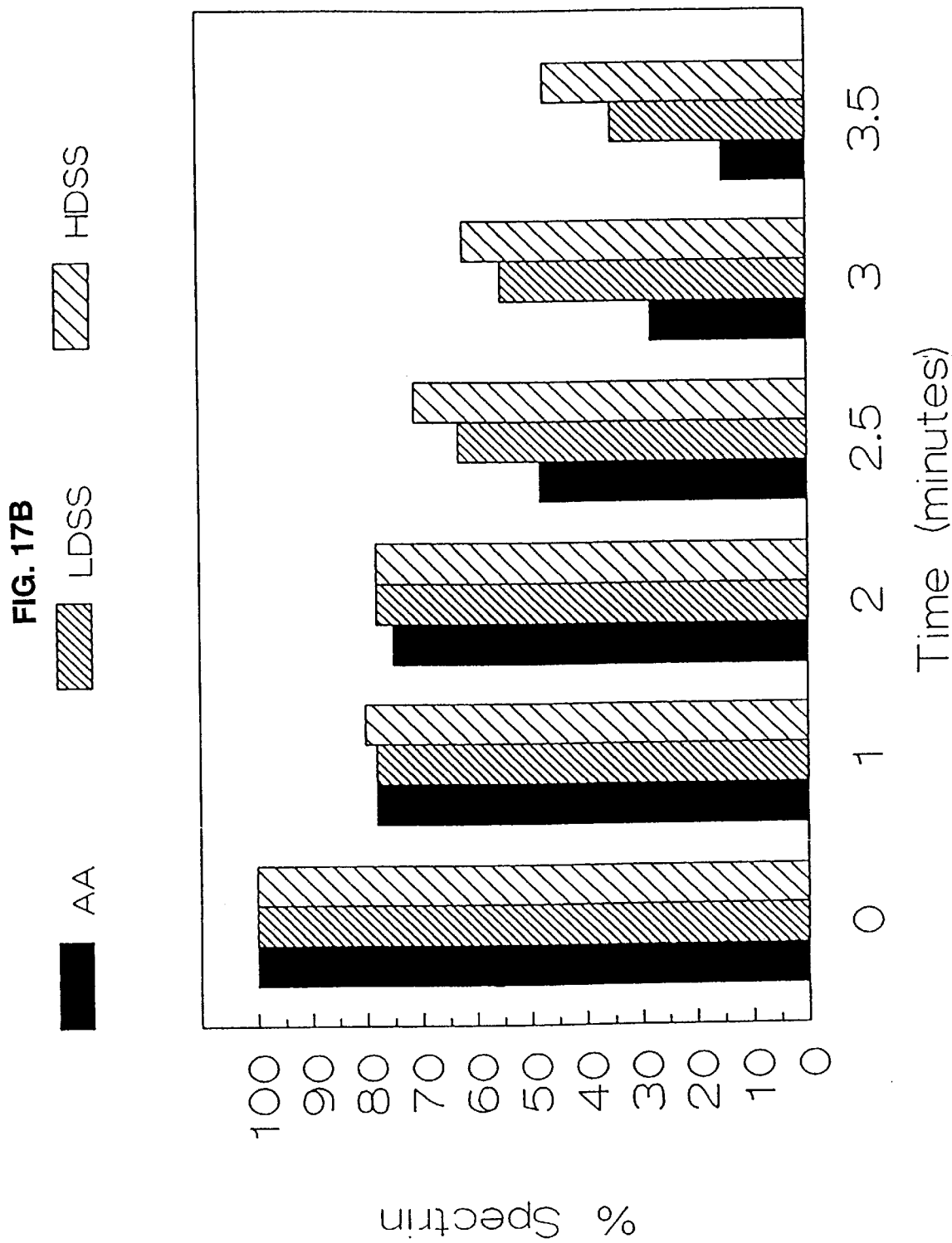

At 0° C. extraction of AA, LDSS, and HDSS erythrocytes in high ionic strength Triton X-100 buffer led to core skeletons containing primarily spectrin, protein 4.1, and actin (FIG. 13A). The densitometric analysis of the SDS-PAGE shown in FIG. 13A, is presented in FIG. 13B. In three independent experiments on blood obtained from three SS subjects and controls, 60–80% of spectrin remains associated with the core skeletons up to 24 hours of extraction. The first order rate constants, at 0° C., for the dissociation of spectrin were the same for AA, LDSS, and HDSS core skeletons within the error of the measurement ($0.030$–$0.035 \times 10^{-4}$ sec$^{-1}$) (Table 2).

At 24° C., over a 3 hours time course, greater dissociation of AA core skeletons than HDSS core skeletons was observed (FIGS. 14A and 14B); with intermediate values for LDSS skeleton. The first order rate constants were $3.78 \pm 0.33 \times 10^{-4}$ sec$^{-1}$ (AA), $1.75 \pm 0.50 \times 10^{-4}$ sec$^{-1}$ (LDSS), and $0.83 \pm 0.35 \times 10^{-4}$ sec$^{-1}$ (HDSS) for spectrin dissociation from the core skeleton. Therefore the rate of dissociation is 4–5 times slower for the HDSS skeleton as compared to the AA skeleton at 24° C., and the differences are statistically significant ($P<0.05$) (Table 2).

At 30° C. (FIGS. 15A and 15B) the first order rate constants for spectrin dissociation from the core skeleton are $11.15 \pm 0.79 \times 10^{-4}$ sec$^{-1}$ (AA), $9.72 \pm 0.98 \times 10^{-4}$ sec$^{-1}$ (LDSS), and $17.29 \pm 0.99 \times 10^{-4}$ sec$^{-1}$ (HDSS). At 30° C. the rate of dissociation was _35% slower for HDSS, versus AA, core skeletons. Again the differences between the dissociation rate constants for HDSS and AA membrane skeleton are significant ($P<0.05$) (Table 2).

Extraction at 34° C. (FIG. 16A and 16B) yielded first order rate constants (Table 2) of $47.50 \pm 7.50 \times 10^{-4}$ sec$^{-1}$ (AA), $40.50 \pm 7.50 \times 10^{-4}$ sec$^{-1}$ (LDSS), and $20.67 \pm 5.00 \times 10^{4}$ sec$^{-1}$ (HDSS). At 34° C. the rate of dissociation was again 56% slower for HDSS, versus AA, core skeletons, and was statistically significant ($P<0.05$) (Table 2).

When extraction was performed at 37° C. (FIG. 17A and 17B) the first order rate constants were $71.33 \pm 12.33 \times 10^{-4}$ sec$^{-1}$ (AA), $56.17 \pm 10.67 \times 10^{-4}$ sec$^{-1}$ (LDSS), and $40.17 \pm 6.83 \times 10^{-4}$ sec$^{-1}$ (HDSS) for spectrin dissociation (Table 2). Once again the rate of dissociation was 44% times slower for the HDSS core skeletons, as compared to the AA core skeletons. The differences in rate constant for HDSS and AA core skeletons was significant ($P<0.05$) (Table 2).

With the first order rate constants for spectrin dissociation from the core skeletons well defined, the effects of the reducing agent DTT on the rate of dissociation was shown. Ghosts were prepared in 1 mM DTT in the lysis buffer, and then carried out the high ionic strength Triton X-100 extraction 5 mM DTT at 30° C. While DTT had no statistically significant effect upon the rate of dissociation of spectrin from AA and LDSS core skeletons (Table 2), it increased the first order rate constant for HDSS core skeleton to a value, $9.78 \pm 0.56 \times 10^{4}$ sec$^{-1}$, which was no longer statistically distinct from the AA rate constants (see Table 2).

Based on functional assays, it was demonstrated that a modification of β-actin is the major determinant of the slow dissociation of the ISC membrane skeleton. Thus, the slower dissociation of the ISC core skeleton is probably responsible for the slow remodelling of the ISC skeleton and hence its persistently sickled shape upon release from the lipid bilayer. Other accessory membrane skeletal proteins, as well as cytoplasmic factors, may also contribute to the inability of the ISC to change shape in vivo.

Furthermore the present invention demonstrates that a posttranslational modification differentiates ISC (or HDSS) β-actin from control β-actin; which is probably a disulfide bridge between cysteine$^{284}$ and cysteine$^{373}$. This latter conclusion is supported by the following observations: (1) The amount of available thiols is approximately 2 mol/mol (AA β-actin) and 0 mol/mol (HDSS β-actin) for nonreduced samples, but becomes 2 mol/mol (AA) and close to 2 mol/mol (HDSS) when β-actin is reduced with DTT. (2) No difference between reduced HDSS and AA β-actin tryptic peptides could be detected by HPLC-FAB-MS. (3) The molecular weights of nonreduced HDSS and AA β-actins are identical ($41,760 \pm 100$ daltons versus $41,690 \pm 100$ daltons) or within 100 mass units of each other. (4) Cysteine$^{284}$ and cysteine$^{373}$ can be labelled by $^{32}$S-DNPTC in the intact AA β-actin molecule but not in the HDSS (or ISC) β-actin molecule; and (5) MALDI mass spectrometric peptide mapping experiments using V8-protease, endoproteinase Lys-C and endoproteinase Asp-N did not show any unknown modification in HDSS actin compared to AA actin within the observed part of the sequence ($\approx 90\%$).

Although β-actin is a major determinant of the ISC skeleton locking mechanism, as determined by the in vitro ternary complex dissociation assay, spectrin also may play a role. The possibility that spectrin reorganization may be involved in the permanent deformation of the ISC membrane skeleton is intriguing. The present invention showing that a modification of β-actin contributes to slower dissociation of ISC versus AA core skeletons at 37° C., suggests that the temperature dependence of actin polymerization and depolymerization at 37° C. and 13° C. must also be considered. Also, the present invention examines why the ISC skeleton remains sickled upon release from the membrane but does not address whether the persistently sickled skeleton was imprinted by an abnormal membrane or vice versa.

It is of great interest to determine the effect of the predicted cysteine$^{284}$-cysteine$^{373}$ intramolecular disulfide bond (or alternative block of these cysteines) upon ISC M-actin structure and its interactions with spectrin and other actin monomers. The present invention shows that the structural modification of ISC β actin would lead to a higher affinity noncovalent interaction with spectrin, other actin monomers, or both. Lux and John (1978) have demonstrated that ISC ghosts could be converted to a round echinocytic shape, after a lag period, by a 20 minute incubation in 600 mM NaCl at 37° C. When ISC core skeletons were incubated in the high ionic strength triton X-100 buffer in a 37° C. water bath (instead of the 37° C. water jacked air/$CO_2$ incubator used herein) that 20 minutes is sufficient time to obtain extensive dissociation. (This is due to the fact that the samples reach the designated temperature (37° C.) more rapidly in the water bath than in an air/$CO_2$ incubator). Therefore the lag period observed in the conversion of ISC ghosts to rounded echinocyte ghosts at 37° C. (Lux and John, 1978) was undoubtedly due to the time required to dissociate the locked ISC skeletons. In the 37° C. water bath one still sees the slower rate of ISC versus control core skeleton dissociation, but both have faster kinetics than observed in the 37° C. air/$CO_2$ incubator. The current observations point to the need of a careful evaluation of the ISC versus control actin-actin and actin-spectrin interactions. Comparisons of ISC versus control actin polymerization rates and the ability of f-actin to bind spectrin_protein 4.1 allow determination whether the modification of cysteines affects actin/actin or actin/spectrin interactions.

Figure 8:
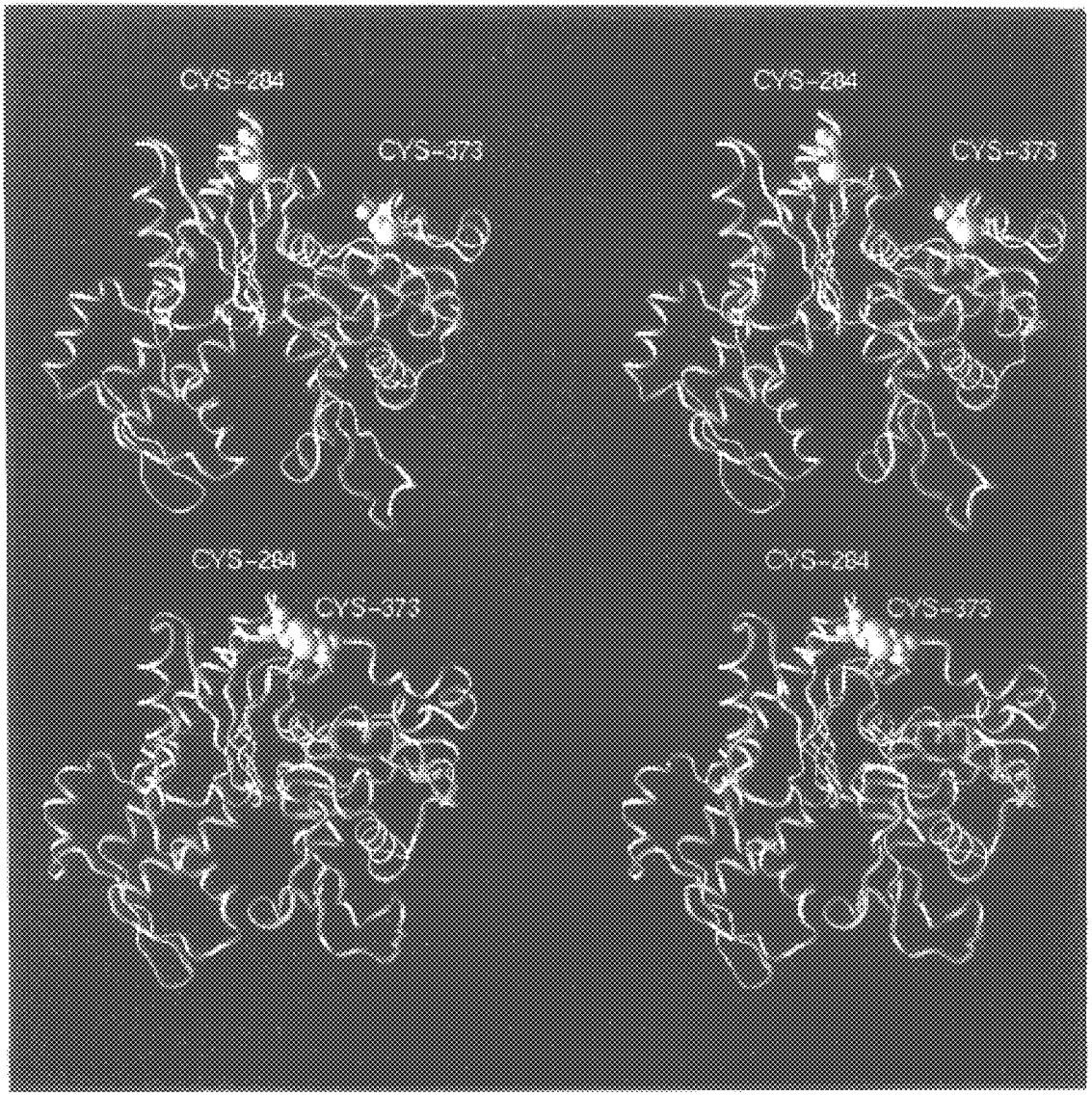
FIG. 8 shows the computer modeling of ISC β-Actin. Stereo view of the beta actin crystal structure backbone (top) with the profilin chaperon portion removed. In the crystal structure, the CYS 373 and 284 side chain sulfur atoms are 21.63 angstroms apart. The second model (bottom) represents beta-actin with the disulfide bridge formed between residues CYS 373 and CYS 284.

Atomic structural models of γ-actin from X-ray crystallography of the actin/DNAse I complex (Kabsch et al, 1990) and bovine β-actin/profilin complex (Schutt et al, 1993) are available. From these models cysteine$^{373}$ in β-actin resides within subdomain I, a region of actin involved in the binding of various actin binding proteins. The β-actin model (Schutt et al, 1993) would place cysteine$^{284}$ in subdomain III, with a separation of 21.63 Angstroms between the two sulfur atoms. This indicates that a substantial conformational change in ISC β-actin would be required to allow disulfide bridge formation to occur between cysteine$^{284}$ and cysteine$^{373}$ (or alternatively that these cysteines are blocked by some other DTT-dependent mechanism which has gone undetected by mass spectroscopy analysis). The inherent assumption in the existing X-ray crystallography analysis of γ-actin (Kabsch et al, 1990, Schutt et al, 1993) is that binding of DNAse or profillin does not alter the structure of actin. But differences in actin structure determined for the actin/DNAse and actin/profillin crystalline structure may indicate that this assumption is not valid. Furthermore, protein structure in solution is dynamic. Extensive computer modeling of the β-actin structure indicates that the $C^{284}$–$C^{373}$ disulfide bond can be formed in solution. FIG. 8 is a stereo view of the backbone of the actin crystal structure and the protein model of the formed $C^{284}$–$C^{373}$ disulfide bond.

From viewing the figure, one can observe only minor shifts in the tertiary structural domain which, for the most part, occur in the proximity of the ATP binding region (RMS deviation of all backbone atoms=2.6 angstroms). It is reasonable that these minor structural changes may not have occurred if an ATP-actin complex structure was used for the molecular modeling simulations. Thus, the carboxy terminal portion of actin (residues 372–374) undergoes a conformational change when its chaperon protein dissociates which orients the $C^{373}$ side chain toward the solvent and predisposes both $C^{373}$ and $C^{284}$ residues to disulfide bond formation. X-ray analysis of β-actin from ISCs and control AA erythrocytes can confirm the distances between cysteine$^{284}$ and cysteine$^{373}$ in control red blood cell β-actin, determine whether the conformational change required for disulfide bridge formation occurs in ISC β-actin, and understand the relationship between the structural changes in β-actin and the functional changes leading towards the "locked" ISC skeleton.

Finally, reduced glutathione levels are diminished about 20% in SS red blood cells as compared to high reticulocyte controls, and is lower in ISCs than in RSCs (Lachant et al, 1983, Wetterstroem et al, 1984). The diminished levels of reduced glutathione are related to decreased glutathione reductase activity, increased glutathione peroxidase activity, and inhibition of the pentose phosphate shunt in SS erythrocytes (Lachant et al, 1983). Therefore ISCs have increased activated oxygen species, but decreased levels of reduced glutathione to protect the cell from oxidant damage. The diminished levels of this intracellular reducing agent, probably led to the cysteine oxidation in ISC β-actin. The membrane permeable reducing agent dithiothreitol blocks the formation of ISCs by in vitro deoxygenation-reoxygenation cycling and converts ISCs isolated from the blood of sickle cell patients to RSCs. Safe membrane permeable reducing agents blocking ISC formation in vivo would be a therapeutic intervention to diminish the number of sickle cell crisis episodes and organ damage related to sickle cell anemia.

The present invention demonstrates that a disulfide bridge does indeed exist between cysteine$^{284}$ and cysteine$^{373}$ of ISC β-actin. This result is consistent with modeling of ISC β-actin based on the atomic structural model from X-ray crystallography of the bovine β-actin/profillin complex (Schutt et al, 1993). Computer modeling suggested that the carboxy terminal portion of actin (residues, 372–374) undergoes a conformational change when its chaperon protein dissociates which orients the $C^{373}$ side chain toward the solvent and predisposes both $C^{373}$ and $C^{284}$ residues to disulfide bond formation. The fact that the previous measurement of available thiols in ISC β-actin gave a value of 0.2 moles/mole actin, verses 2 moles of thiol/mole actin in the control, suggested that at least 90% of the ISC β-actin would contain the disulfide bridge. The present invention the first definitive proof by the identification of the KCF-CDVDIR cysteine linked peptide in the tryptic digest of ISC β-actin.

The discovery of the disulfide linked KCF-CDVDIR peptide was based on the ability to prepare the synthetic peptide. Several facts about the chemistry of aromatic sulfenyl halides are worth noting and should be helpful to those with ordinary skill in this art working to prepare cysteine linked synthetic peptides. First, nitro- and dinitrosulfenyl-chloride react not only with thiol groups but also with indole moieties (Scoffone et al., 1968) Thus not only cysteine but also tryptophan can be modified. This latter reaction quantitatively (and irreversibly) transforms the indole moieties into 2-(2', 4'-dinitrophenyl)-thioindole derivatives. Azobenzenesulfenyl bromide, however, reacts solely with the sulfhydryl groups (Fontana et al., 1968b) but is far more expensive that the dinitrosulfenyl-chloride. Since the peptides did not contain tryptophan, the specificity of DNS-Cl was adequate. Secondly, the aromatic sulfenyl halides are fairly hydrolysis resistant compounds, and therefore the activation step does not require absolute conditions. In fact, the reaction may be carried out in 50% aqueous acetic acid solution (Scoffone et al., 1968). Thirdly, according to the Fontana method, the reaction mixture is poured in ether at the end of the activation reaction, and the precipitate is filtered. Because of the small amounts of peptide with which the reaction was started (4 mg KCF), the ether was replaced with a mixture of tetrahydrofurane and toluene (1:10), and the filtration by centrifugation. These modifications allowed the reaction to be carried out in one single centrifuge glass at ambient temperature, with an excellent overall yield (80%). Therefore, the disulfide bridge between cysteine$^{284}$ and cysteine$^{373}$ in ISC β-actin is critical in ISC formation, and is target of for therapies designed to block ISC formation in sickle cell subjects.

The present invention demonstrates that DTT causes an increased rate of dissociation of the HDSS core skeleton, while having little effect upon the rate of LDSS and control (AA) core skeletons. This is consistent with the suggestion that reversible thiol oxidation is the cause of the slow dissociation of the HDSS membrane skeleton, and therefore the slow remodelling of the ISC and the USDs.

The present invention demonstrated that, at all temperatures tested between 24° C. and 37° C., spectrin dissociates more slowly from HDSS core skeletons than from AA or LDSS core skeletons. These studies were carried out under more rigorous temperature control (water bath) than the air/$CO_2$ incubator. The conclusion remains that HDSS skeletons dissociate more slowly, than AA and LDSS core skeletons and this may explain the slow remodelling of the ISC membrane skeleton.

The assay for membrane skeleton dissociation in high ionic strength Triton X-100 buffer is of value in the testing of drugs to hasten the dissociation rate of HDSS, or ISC, core skeletons in vitro. A disulfide bridge between cysteine 284 and cysteine 373 in β-actin is the major cause of the slow dissociation of the ISC membrane skeleton suggesting that membrane permeable reducing agents are of value. Dithiothreitol (DTT) can block the formation of ISCs in vitro, and can convert ISCs formed in vivo back to RSCs.

The present invention demonstrated that DTT can hasten the dissociation of the HDSS or ISC core skeleton; demonstrating the value of this assay in testing the efficacy of various drugs on membrane skeletal interactions. The carefully defined rate parameters, described in the herein allows the use of this assay to test various nontoxic reducing agents and antioxidants to help determine the most promising therapeutic agents for blocking ISC formation in patients with sickle cell anemia.

Blocking the Formation of Irreversibly Sickled Cells with N-acetyl Cysteine

Irreversibly sickled cells are the major contributors to vasoocclusion and organ damage in sickle cell disease. The slow dissociation of the irreversibly sickled cell membrane skeleton and the inability of the irreversibly sickled cell to remodel back to a biconcave shape are due to the formation of a disulfide bridge between cysteins 284 and 373 of β-actin as described in detail above. This disulfide bridge is not found in the β-actin of normal red blood cells. Identification of non-toxic, and thus clinically useful, membrane permeable reducing agents that inhibit irreversibly sickled cell occurrence would lower irreversibly sickled cells in the circulation and thereby reduce the clinical severity of sickle cell anemia.

Irreversibly sickled cells and reversibly sickled cells were isolated from the blood of patients with sickle cell anemia using a five layer step Percoll gradient. The reversibly sickled cells were subjected to deoxygenation-reoxygenation cycling to generate irreversibly sickled cells in vitro at final concentrations of 0, 100 $\mu$M, 250 $\mu$M, 500 $\mu$M, 10 mM, and 20 mM N-acetyl cysteine in incubation buffer for 16 hours at 37° C. The results from these experiments show that it is possible to inhibit irreversibly sickled cell formation in vitro using clinically relevant doses (500 $\mu$M to 20 mM) of N-acetyl cysteine. In the in vitro experiments, there was a statistically significant decrease (p<0.05) in irreversibly sickled cells at concentrations above 500 $\mu$M. The irreversibly sickled cells formed in vivo were incubated in N-acetyl cysteine at final concentrations of 0, 100 $\mu$M, 250 $\mu$M, 500 $\mu$M, 10 mM and 20 mM in incubation buffer at 37° C. for 16 hours. These experiments did not indicate a significant conversion of irreversibly sickled cells back to the biconcave red blood cells when compared to controls without N-acetyl cysteine. Therefore, at the concentrations tested, N-acetyl cysteine blocked the formation of ISCs but could not convert irreversibly sickled cells formed in vivo back to the biconcave shape.

Preparation of Light Density and High Density RBC

The ability of two reducing agents, dithiothreitol and n-acetyl cysteine to block ISC formation in vitro and to convert ISCs back to biconcave cells was demonstrated. Blood (20–30 ml) was obtained by venipuncture from homozygous SS subjects in vacutainer tubes containing 143 USP units of lithium heparin. Fresh blood (5 ml/gradient) was placed over a discontinuous Percoll density gradient containing 8 ml each of 25%, 45%, 55% and, 65% Percoll in 18% Renogratin M-60 (Squibb) in 20 mM Hepes, 10 mM $MgCl_2$, 10 mM glucose, pH 7.4. The blood is sedimented at 907×g for 45 minutes at 4° C. and the light density cells (45% layer) and high density cells (65% layer) were removed without cross contamination. The low density and high density cells were washed 2× in PBS (10 mM $NaPO_4$, 150 mM NaCl, pH 7.6) and sedimented at 2520×g for 5 minutes. A 2% suspension of high and low density cells was prepared in incubation buffer (20 mM Hepes, 130 mM NaCl, 5 mM Kcl, 1 mM $MgCl_2$, 30 mM glucose, 2 mM $naPO_4$, 2 mM $CaCl_2$, 1 mM adenosine, 1 mM inosine, 0.5% BSA and 100 units Penicillin G, 100 $\mu$g Streptomycin, 0.25 $\mu$g Amphotericin B.

In Vitro Formation of ISCs by Cyclic Oxygenation-Deoxygenation Inhibition by DTT and N-Acetyl Cysteine The 2% solution of light density cells in 10 ml of incubation-buffer plus 0–5 mM DTT or 1–20 mM n-acetyl cysteine was placed in 50 ml volumetric flasks. The samples were incubated at 37° C., in a shaker water bath, with cycling of 15 minutes $N_2$ followed by 5 minutes air for a total time of 16 hours. After 16 hours, the samples were flushed with O2 for 20 minutes and aliquots were fixed with 1% glutaraldehyde. Blood smears were prepared and a minimum of 500 rbcs counted to determine % ISCs. Cells with a length/width ratio of $\geq 2$ were counted as ISCs. To demonstrate reversion of preformed ISCs to biconcave cells, the 2% solution of high density cells in 10 ml of incubation buffer plus 0 to 5 mM DTT or 1 to 20 mM n-acetyl cysteine was placed into a loosely stoppered 50 ml volumetric flask. The samples were incubated at 30° C. or 37° C. for 16 hours, and then an aliquot is removed and brought to 1% glutaraldehyde. A blood smear was prepared and the precentage of ISCs determined as described above.

Dithiothreital inhibits the in vitro formation of ISCs at 37° C. at all concentrations tested from 1.0 mM to 5.0 mM DTT. At 5 mM DTT there was a 31.7% inhibition of ISCs formed by cyclic oxygenation-deoxygenation (Table 3). DTT also can convert preformed ISCs, found in the high density fraction of sickle cell patient blood, back to biconcave cells (Table 4). For example, 1.0 mM DTT caused a 46% reduction in ISCs over a 16 hour period at 37° C.

TABLE 3

| In Vitro Formed ISCs Dithiothreitol | Percent ISCs | Percent Decrease |
|---|---|---|
| Control | 8.3 ± 3.5 | |
| 0.0 mM | 42.6 ± 3.5 | |
| 1.0 mM | 32.2* ± 0.9 | 23.4* ± 4.7 |
| 2.5 mM | 30.7* ± 2.5 | 27.8* ± 2.0 |
| 5.0 mM | 29.7* ± 4.8 | 31.7* ± 5.7 |

Table 3: Percent ISCs formed during cyclic oxygenation/deoxygenation of dithiothreitol treated light density (45% Percoll layer) sickle cells at 37° C. The control represents the sickle cells without cycling and dithiothreitol treatment. The values represent the mean and standard error of 4 experiments. The asterick (*) indicates a significant difference form 0.0 mM dithiothreitol concentrations (p <0.05).

TABLE 4

| Conversion of Preformed ISCs | | | |
|---|---|---|---|
| DTT | Temperature | Percent ISCs | Percent Decrease |
| 0.0 mM | 37° C. | 52.1 | — |
| 0.5 mM | 37° C. | 33.8 | 35 |
| 1.0 mM | 37° C. | 28.0 | 46 |
| 0.0 mM | 30° C. | 50.4 ± 8.8(4) | — |
| 0.5 mM | 30° C. | 43.0 | 12.6 |
| 1.0 mM | 30° C. | 34.3 ± 2.3(2) | 30 ± 5(2) |
| 2.5 mM | 30° C. | 30.5 ± 2.9(3) | 34 ± 12(3) |
| 5.0 mM | 30° C. | 29.2 ± 5.8(4) | 41 ± 5(4) |

Table 4: Percent decresed in ISCs after treating high density (65% and higher Percoll layer) sickle cells with 0 mM to 5 mM DTT at 37° C. and 30° C. The values represent the mean and standard deviation with the number of experiments in parentheses.

N-acetyl cysteine also inhibits the in vitro formation of ISCs at concentrations of 250 mM to 20 mM n-acetyl cysteine. N-acetyl cysteine at 20 mM caused a 36.7% decrease in the levels of ISCs produced by cyclic oxygenation-deoxygenation (Table 5). However, n-acetyl cysteine does not cause a statistically significant conversion of preformed ISCs back to biconcave cells (Table 6).

TABLE 5

In Vitro Formed ISCs

| N-acetyl Cysteine | Percent ISCs | Percent Decrease |
|---|---|---|
| Control | 8.95 ± 3.60(8) | — |
| 0 mM | 59.04 ± 5.95(8) | 0.00(8) |
| 0.1 mM | 50.80 ± 15.06(4) | 19.84 ± 11.77(4) |
| 0.25 mM | 49.72 ± 11.51(4)* | 15.53 ± 1.56(4)* |
| 0.50 mM | 49.84 ± 5.54(8)* | 16.25 ± 4.13(8)* |
| 10.0 mM | 46.82 ± 2.92(4)* | 21.695.27(4)* |
| 20.0 mM | 37.954.98(4)* | 36.66 ± 8.09(4)* |

TABLE 6

Conversion of Preformed ISCs

| N-acetyl Cysteine | Percent ISCs | Percent Decrease |
|---|---|---|
| Control | 69.32 ± 4.31(6) | — |
| 0 mM | 58.85 ± 4.69(6) | 0.00(6) |
| 0.1 mM | 58.91 ± 8.88(3) | 7.74 ± 0.88(3) |
| 0.25 mM | 55.08 ± 6.93(3) | 8.25 ± 2.48(3) |
| 0.50 mM | 60.75 ± 4.27(6) | 4.19 ± 3.06(6) |
| 10.0 mM | 56.21 ± 2.12(3) | 9.85 ± 2.70(3) |
| 20.0 mM | 54.31 ± 4.50(3) | 9.85 ± 2.70(3) |

Reducing agents such as DTT and n-acetyl cysteine block ISC formation in vitro. N-acetyl cysteine is an FDA approved drug which can be reducing ISCs in the blood stream of patients with sickle cell anemia. Reduction of ISCs should lead to fewer painful sickle cell crises and a lessening of tissue and organ damage.

References

Ballas, et al., (1988). Blood 72, 1216–1223.
Ballas, et al., (1992). Blood, 79, 2154–2163.
Beavis, et al., (1989). Rapid Commun. Mass Spect. 3, 233–237.
Beavis, R. C. and Chait, B. T. (1990). Anal. Chem. 62, 1836–1840.
Bennett, V., and Stenbuck, P. J. (1979). J. Biol. Chem. 254, 2533–2541.
Bennett, V., and Stenbuck, P. J. (1980). J. Biol. Chem. 255, 6424–6432.
Brenner, S. L., and Korn, E. (1979). J. Biol. Chem. 254, 8620–8627.
Byers, et al., 1985. Proc. Natl. Acad. Sci. USA 82: 6151–6157.
Cohen, et al., 1980. Cell 21:875–883.
Drewes, G., and H. Faulstich. 1990. Anal. Biochem. 188:109–113.
Ellman, G. L. 1958. Arch. Biochem. Biophys. 74:443–450.
Fabry, et al.,1984. Blood 64:559–565.
Fabry, et al., 1992. Blood 79:1602–1611.
Fontana, et al., 1968. Biochemistry 7:980–986.
Fowler, V. M., and V. Bennett. 1984. J. Biol. Chem. 259:5978–5989.
Fowler, V., and D. L. Taylor. 1980. J. Cell Biol. 85:361–376.
Francis, et al., 1991. Blood 77:1405–1414.
Gardner, K., and V. Bennett. 1987. Nature 328:359–362.
Goodman, et al., 1981. Proc. Nat'l Acad. Sci. USA 78:7570–7574.
Goodman, et al., 1988. CRC Crit. Rev. Biochem. 23:171–234.
Hargreaves, et al., 1980. J. Biol. Chem. 255:11965–11972.

Hebbel, R. P. 1990. Sem. Hematol. 27:51–69.
Hebbel, R. P. 1991. Blood 77:214–237.
Hebbel, et al., 1982. J. Clin. Invest. 70:1253–1259.
Hebbel, et al., 1988. Proc. Natl. Acad. Sci. USA 85:237–242.
Joiner, C. H. 1993. Am. J. Physiol. 264:C251–C270.
Kabsch, et al., 1990. Nature 347:37–44.
Karinch, et al., 1990. J. Biol. Chem. 265:11833–11840.
Kaul, et al., 1986. Blood 68:1162–1169.
Kaul, et al., 1989. Proc. Natl. Acad. Sci. USA 86:3356–3362.
Kaul, et al., 1983. J. Clin. Invest. 72:22–31.
Kuross, et al., 1988. Blood 71:876–882.
Lachant, et al., 1983. Am. J. Hematol. 15:1–13.
Laemmli, U. K. 1970. Nature 227:680–685.
Lande, et al., 1988. Blood 72:2056–2059.
Liu, et al., 1987. J. Cell Biol. 104:527–536.
Liu, et al., 1993. Blood 81:522–528.
Lux, S. E., and K. M. John. 1978. In Biochemical and Clinical Aspects of Hemoglobin Abnormalities. W. Caughey, ed. NY, N.Y. Acad Press. 335–352.
Lux, et al., 1976. J. Clin. Invest. 58:955–963.
Maple, et al., 1990. Chem. Design Automat. News 5(9):5–10.
Mische, et al., 1987. J. Cell Biol. 105:2837–2845.
Montgomery, D. C. 1991. Design and analysis of experiments. New York, N.Y., John Wiley & Sons.
Mueller, et al. 1981. In Erythrocyte Membranes 2: Recent Clinical and Experimental Advances. W. C. Kruckeberg, ed. NY, N.Y. A Liss Inc. 95–112.
Nakajima-Iijima, et al., 1985. PNAS USA 82:6133–6137.
Platt, et al., 1985. J. Clin. Invest. 75:266–271.
Powers, D. R. 1990. Hemoglobin 14: 573–598.
Rank, et al. 1985 J. Clin. Invest. 75:1531–1537.
Sahr, et al., 1990. J. Biol. Chem. 265:4434–4443.
Schutt, et al., 1993. Nature 365:810–816.
Schwartz, et al., 1987 J. Biol. Chem. 262:15666–15672.
Sheetz, M. P. 1979. Biochim. Biophys. Acta. 551:122–134.
Shen, et al., 1986. J. Cell. Biol. 102:997–1006.
Shiffer, et al.,1984. Proc. Natl. Acad. Sci. USA 81:4404–4408.
Shotton, et al., 1979. J. Mol. Biol. 131:303–329.
Siegel, D. L., and D. Branton. 1985. J. Cell Biol. 100: 775–785.
Tyler, et al., 1979. Proc. Natl. Acad. Sci. USA 76:5192–5196.
Ungewickell, et al., 1979. Nature 280:811–814.
Vandekerckhove, J. and K. Weber. 1978 J. Mol. Biol. 126:783–802.
Wallin, et al., 1984. Proc. Natl. Acad. Sci. USA 81:4095–4099.
Wetterstroem, et al., 1984. J. Lab Clin. Med. 103:589–596.
Winkelmann, et al., 1990. J. Biol. Chem. 265:11827–11832.
Yu, et al., 1973 J. Supramol. Struct. 1:233–248.
Yu, J., and S. R. Goodman. 1979. PNAS USA 76:2340–2344.
1. Shartava et al., J Cell Biol 128:805, 1995.
2. Hebbel R P: Sem Hematol 27:51, 1990
3. Hebbel R P: Blood 77:214, 1991
4. Powers D R: Hemoglobin 14:573, 1990
5. Francis et al., Blood 77:1405, 1991
6. Joiner C H: Am J Physiol 264:C251, 1993
7. Fabry et al., Blood 79:1602, 1984
8. Kaul et al., J Clin Invest 72:22, 1983
9. Kaul et al., Blood 68:1162, 1986
10. Kaul et al., Proc Natl Acad Sci USA 86:3356, 1989
11. Ballas et al., Blood 72, 1216, 1988
12. Lande et al., Blood 72:2056, 1988
13. Ballas et al., Blood 79:2154, 1992
14. Lux et al., J Clin Invest 58:995, 1976
15. Laemmli, U. K. 1970. Nature (Lond.) 227:680–685.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating sickle cell anemia in an individual in need of said treatment, comprising the step of:

administering to said individual a therapeutically effective dose of a reducing agent.

2. The method of claim 1, wherein said reducing agent is selected from the group consisting of N-acetyl cysteine, dithiothreitol, cysteamine, dimercaprol and succimer.

3. The method of claim 1, wherein said reducing agent is n-acetyl cysteine and is administered in a dose of from about 70 mg/kg to about 140 mg/kg.

* * * * *